US008883846B2

(12) United States Patent
Wulff et al.

(10) Patent No.: US 8,883,846 B2
(45) Date of Patent: Nov. 11, 2014

(54) SYNTHESIS OF BICYCLIC COMPOUNDS AND METHOD FOR THEIR USE AS THERAPEUTIC AGENTS

(75) Inventors: Jeremy E. Wulff, Victoria (CA); Michael G. Brant, Victoria (CA); Jeremy W. Mason, Sarnia (CA); Caleb M. Bromba, Fort St. John (CA); Martin J. Boulanger, Victoria (CA)

(73) Assignee: UVic Industry Partnerships Inc., Victoria, British Columbia (CA)

( * ) Notice: Subject to any disclaimer, the term of this patent is extended or adjusted under 35 U.S.C. 154(b) by 33 days.

(21) Appl. No.: 13/586,687

(22) Filed: Aug. 15, 2012

(65) Prior Publication Data

US 2013/0210904 A1 Aug. 15, 2013

Related U.S. Application Data

(63) Continuation-in-part of application No. PCT/CA2011/000174, filed on Feb. 14, 2011.

(60) Provisional application No. 61/304,738, filed on Feb. 15, 2010, provisional application No. 61/591,630, filed on Jan. 27, 2012.

(51) Int. Cl.

| | |
|---|---|
| *A61K 31/381* | (2006.01) |
| *C07D 333/78* | (2006.01) |
| *C07C 279/16* | (2006.01) |
| *C07C 279/22* | (2006.01) |
| *C07C 67/08* | (2006.01) |
| *C07C 215/44* | (2006.01) |
| *C07C 35/31* | (2006.01) |
| *C07C 211/41* | (2006.01) |
| *C07C 67/29* | (2006.01) |
| *C07C 29/56* | (2006.01) |
| *C07C 233/52* | (2006.01) |

(52) U.S. Cl.
CPC ............ *C07C 279/16* (2013.01); *C07C 279/22* (2013.01); *C07C 67/08* (2013.01); *C07C 215/44* (2013.01); *C07C 35/31* (2013.01); *C07C 2102/22* (2013.01); *C07C 211/41* (2013.01); *C07C 67/29* (2013.01); *C07C 29/56* (2013.01); *C07D 333/78* (2013.01); *C07C 233/52* (2013.01)
USPC ........................................................ 514/443

(58) Field of Classification Search
CPC .............................. C07C 29/56; C07D 333/78
USPC ............................................ 514/443; 549/53
See application file for complete search history.

(56) References Cited

PUBLICATIONS

Brant et al, "Tandem Vinylogous 1,2-Addition/Anionic Oxy-Cope Reaction Leading from Butadiene Sulfone to an Orthogonally Functionalized Bicycle," *Journal of Organic Chemistry* 75:6312-6315, 2010.

Bromba et al., "The de-guanidinylated derivative of peramivir remains a potent inhibitor of influenza neuraminidase," *Bioorganic & Medicinal Chemistry Letters* 21:7137-7141, 2011.

International Search Reported from International Application No. PCT/CA2011/000174 dated Jun. 2, 2011.

*Primary Examiner* — Taofiq A Solola

(74) *Attorney, Agent, or Firm* — Klarquist Sparkman, LLP

(57) ABSTRACT

Disclosed embodiments concern the synthesis and use of therapeutic compounds that for treating emerging flu strains and minimizing resistance to such strains. Methods for making the disclosed compounds concern using a base-mediated addition/cyclization sequence followed by functional group manipulation to develop functionalized compounds that can target neuraminidase, which makes them ideal candidates for treating influenza. Pharmaceutical compositions comprising the therapeutic compounds and biologically-acceptable materials are also described. Methods of inhibiting neuraminidase in subjects that are suspected of containing neuraminidase are also described. The use of metabolites of the disclosed compounds can also be used in diagnostic assays for therapeutic dosing of the disclosed compounds.

18 Claims, 12 Drawing Sheets

SYNTHESIS OF BICYCLIC COMPOUNDS AND METHOD FOR THEIR USE AS THERAPEUTIC AGENTS

CROSS REFERENCE TO RELATED APPLICATION

This is a continuation-in-part under 35 U.S.C. §120 of International Application No. PCT/CA2011/000174, filed on Feb. 14, 2011, which claims the benefit of the earlier filing date of U.S. Provisional Application No. 61/304,738, filed on Feb. 15, 2010, and this application further claims the benefit of the earlier filing date of U.S. Provisional Application No. 61/591,630, filed on Jan. 27, 2012. Each of these prior applications is incorporated herein by reference in its entirety.

FIELD

The present invention relates to a method for making and using chemical compounds, structural analogues and derivatives thereof, for the treatment, prevention, or amelioration of diseases, particularly diseases with sialidase virulence factors.

BACKGROUND

Neuraminidase (also known as sialidase, acylneuraminyl hydrolase) is an enzyme common among animals and a number of microorganisms. It is a glycohydrolase that cleaves terminal alpha-ketosidically linked sialic acids from glycoproteins, glycolipids and oligosaccharides. Many of the microorganisms containing neuraminidase are pathogenic to man and other animals including fowl, horses, swine and seals. These pathogenic viruses include influenza.

Influenza is typically transmitted through aerosols as a result of coughing and sneezing by those infected. The virus can also be contracted by exposure to bird droppings, saliva, nasal secretions, feces and blood. The 80-120 nm viral particles consist of an outer envelope and a central core containing the RNA genome, along with various packaging proteins. The influenza genome is not a single piece of RNA, but instead is contained on 8 separate strands of negative-sense RNA, which together encode the 11 genes necessary for viral replication: hemagglutinin, neuraminidase, nucleoprotein, M1, M2, NS1, NS2(NEP), PA, PB1, PB1-F2 and PB2.

Hemagglutinin and neuraminidase are glycoproteins that exist on the outside of the viral particle. During the infection of host cells, the hemagglutinin protein binds to sialic acid residues on the surface of epithelial cells located in the nose, throat, and lungs. The hemagglutinin is subsequently cleaved by host proteases, triggering importation of the viral particle into the host cell by endocytosis. Once inside the cell, the M2 ion channel transports protons from the acidic endosomal fluid into the core of the virus. This drop in internal pH triggers disassembly of the core and release of the viral RNA.

The negative-sense RNA is then transported into the host cell's nucleus, where it is transcribed to the corresponding positive-sense RNA before being exported to the cytoplasm and translated into viral proteins. These are assembled with negative-sense RNA into viral progeny that remain attached to the host cell via hemagglutinin-sialic acid interactions. Finally, the neuraminidase enzyme cleaves sialic acid from the host cell, allowing the newly formed viral particles to infect neighbouring cells.

Because of the absence of RNA proofreading enzymes, RNA transcription results in an error about once every 10,000 nucleotides. Since this is roughly the length of the total RNA present in the influenza genome, evolution is very rapid. Moreover, the separation of the genome into eight separate lengths of RNA permits shuffling of genetic sequences between viruses, if more than one strain of influenza infects a single cell. Together, these mechanisms of "antigenic drift" and "antigenic shift" lead to rapid evasion of established drug or vaccine protocols.

While the influenza virus mostly resides in the lungs, recent evidence that the swine flu strain of H1N1 can penetrate to the gut in animal models raises concerns that drugs with low systemic availability (e.g. zanamivir) will promote reservoirs of the virus elsewhere in the body. These systemic viral reservoirs would be exposed to relatively low doses of the drug over time, providing ideal conditions to evolve further resistance.

Treatment of influenza infections relies on two classes of molecules. The first class includes the molecules amantadine and rimantadine, and works by blocking the M2 proton channel. However, resistance to amantadine and rimantadine is now widespread.

The second class of drugs targets viral neuraminidase (also called sialidase). Zanamivir (Relenza™) was developed in 1989 as a structural mimic of the boat-shaped sialic acid-hydrolysis transition structure, and proved effective in limiting viral replication. However, the large number of heteroatoms within zanamivir's structure limits its oral bioavailability. As a result, it must be administered by inhalation, and has therefore seen somewhat limited clinical use.

Oseltamivir (Tamiflu™) is a second-generation neuraminidase inhibitor developed by Gilead Sciences with substantially improved oral bioavailability. This molecule (marketed by Roche) dominates the influenza market, with sales of about $1 billion per year. Oseltamivir is a prodrug, which is hydrolyzed in the liver to form the biologically active carboxylate. The drug is made in a lengthy synthesis from (−)-shikimic acid, a natural product isolated from the Chinese star anise. Frequent global shortfalls in shikimic acid production threaten Roche's ability to provide large quantities of oseltamivir in response to influenza pandemics. Several alternative syntheses by prominent synthetic groups have appeared in the literature over the past few years, but so far none have been commercialized.

In an attempt to access neuraminidase inhibitors with a core structure distinct from oseltamivir, BioCryst pharmaceuticals developed the substituted cyclopentane peramivir (BCX-1812). This structure, containing a β-hydroxy acid function, is ten-fold more potent than oseltamivir possibly due in part to the interaction of the hydroxyl group with the aspartic acid residue (Asp151) present in the active site to recognize the α-hydroxyl group in sialic acid. Although originally intended as an oral antiviral agent, peramivir displayed poor bioavailability in early trials, and is now being studied in formulations suitable for intravenous and intramuscular injection. Other anti-influenza drugs are also in development, but these likewise suffer various disadvantages.

Because mutations in a key enzyme like neuraminidase are often toxic to the organism, resistance to oseltamivir or zanamivir was once thought to be less problematic than resistance to amantadine. Indeed, data prior to the 2007/2008 flu season showed resistance levels of ~1%, with somewhat higher levels in children. Resistance increased dramatically in 2007, however, with oseltamivir-resistant H1N1 strains detected in the United States (10.9%), Canada (26%), Europe (25%) and Hong Kong (12%). Even more alarming, data from the first half of the 2008/2009 flu season (prior to the emergence of the swine flu H1N1 strain) showed that nearly all circulating cases of H1N1 influenza A were resistant to oseltamivir.

Both oseltamivir and peramivir were designed on the principle that the polar sidechain of sialic acid (and thus zanamivir) could be replaced by a large, lipophilic alkyl group. While this led to very active inhibitors (oseltamivir is effective at around 1 nM; peramivir is roughly ten-fold more potent), it provides an obvious mechanism for drug resistance. Indeed, influenza strains containing group 1 neuraminidases (N1, N4, N5, N8) are susceptible to a second-shell mutation wherein histidine-274 of the enzyme is mutated to a tyrosine. This mutation results in the reorganization of a nearby glutamic acid residue (Glu276) such that it projects into the active site of the enzyme, where it suffers unfavourable interactions with the lipophilic alkyl group. The H274Y mutation is responsible for the majority of drug resistance described above, conferring resistance to both oseltamivir and peramivir. While strains of influenza expressing these variants remain susceptible to zanamivir (the polar sidechain engages in hydrogen-bonding with Glu276), the lack of oral bioavailability for this drug makes it a less desirable therapeutic.

Moreover, other neuraminidase mutations confer resistance to zanamivir. In addition to several zanamivir-resistant mutants generated in vitro (influenza A N2: E119G/D/A, R292K; influenza A N9: E119G, R292K; influenza B: E119G/D), a recent sampling of Australian and South East Asian influenza A H1N1 viruses revealed a novel mutation (Q136K) which caused a 300-fold reduction in zanamivir susceptibility, as well as a 70-fold reduction in peramivir susceptibility. An earlier zanamivir-resistant strain of influenza B (containing the R152K mutation) was isolated from an immunocompromised patient undergoing prolonged zanamivir treatment.

To effectively combat emerging flu strains and minimize the potential for resistance, novel therapeutic platforms that are effective against the H274Y variant and are sufficiently "plastic" to overcome new polymorphisms are essential.

SUMMARY

Disclosed embodiments concern compounds of the formula:

With reference to this general formula, V, $V_a$, $V_b$, and $V_c$ independently are selected from $CR^{11}R^{12}$, $C(R^{11})_2$, $CR^{12}R^{13}$, $C(R^{13})_2$, $SO_2$, SO, S, O, $NR^{11}$, CO, and Se;

W is nitrogen, $CR^{10}$, or $CR^{11}$;

$R^{10}$ is H, alkyl or $(CH_2)OH$;

$R^{11}$ is H, alkyl, branched alkyl, cyclic alkyl, aryl, a heteroatom-containing moiety, and any combination thereof. The heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof. The heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino;

if $V_a$ comprises $CR^{11}R^{12}$, $C(R^{11})_2$, $CR^{12}R^{13}$, or $C(R^{13})_2$, then $V_a$ and $V_b$ together can comprise a lactone or a lactam;

if $V_c$ comprises $CR^{11}R^{12}$, $C(R^{11})_2$, $CR^{12}R^{13}$, or $C(R^{13})_2$ and has at least two substituents selected from $R^{11}$, $R^{12}$, or $R^{13}$, or any combination thereof, then the two substituents together can form a cyclic alkyl group;

n=0, 1 or 2; and m 0, 1 or 2.

Particular embodiments concern compounds having a formula:

With reference to this general formula, V is $CR^{11}R^{12}$, $C(R^{11})_2$, $SO_2$, SO, S, O, $NR^{11}$, CO, and Se; particularly, V is $CHR^{12}$, $SO_2$, SO, S, or CO;

$R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof;

$R^2$ is H, OH, $(CH_2)_nZH$, where Z=O, S, Se, or $NR^{11}$;

or where $R^1$ and $R^2$ together represent =O;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)NHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, alkenyl, alkynyl, aryl or heteroaryl;

or where $R^5$ and $R^1$ together form a lactam or lactone;

$R^6$ is H, alkyl or $(CH_2)_nOH$;

$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH_2)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, heterocyclic, amino or guanidino, and Z=O, S, Se, or $NR^{11}$;

or where $R^7$ and $R^8$ together represent a cyclic alkyl group;

$R^9$ is H, alkyl, branched alkyl, cyclic alkyl, alkenyl, alkynyl, aryl, heteroaryl, $O(R^{11})_m$, $S(R^{11})_m$, $N(R^{11})_m(H)_{(2-m)}$, $(CH_2)_nZH$, $(CH_2)_nZR^{11}$, $(CH_2)_nZ(CO)R^{11}$, $(CH_2)_nZ(SO_2)$ $R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

n=0, 1 or 2; and
m=0, 1 or 2.

Other embodiments concern compounds having a formula:

With reference to this general formula, V is $CR^{11}R^{12}$, $C(R^{11})_2$, $SO_2$, SO, S, O, $NR^{11}$, CO, and Se; particularly, V is $CHR^{12}$, $SO_2$, SO, S, or CO;

$R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof;

$R^2$ is H, OH, $(CH_2)_nZH$, where Z=O, S, Se, or $NR^{11}$;

or where $R^1$ and $R^2$ together represent =O;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, alkenyl, alkynyl, aryl or heteroaryl;

or where $R^5$ and $R^1$ together form a lactam or lactone;

$R^6$ is H, alkyl or $(CH_2)_nOH$;

$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_m[CH(ZH)]_nCH_2Y$, where Y is aryl, heteroaryl, alkyl or cyclic alkyl, heterocyclic, amino or guanidino, and Z=O, S, Se, or $NR^{11}$;

or where $R^7$ and $R^8$ together represent a cyclic alkyl group;

$R^9$ is H, alkyl, branched alkyl, cyclic alkyl, alkenyl, alkynyl, aryl, heteroaryl, $O(R^{11})_m$, $S(R^{11})_m$, $N(R^{11})_m(H)_{(2-m)}$, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

n=0, 1 or 2; and
m 0, 1 or 2.

Certain disclosed compounds further satisfy the following general formulae, where V is selected from $CHR^{12}$, $SO_2$, SO, S, or CO, where $R^{12}$ is selected from H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$; and the remaining substituents are as stated above.

Certain disclosed embodiments also relate to derivatives accessible from those above, for example by the method of Sellstedt and Almqvist, including those represented by the following formula:

Each V independently is selected from $SO_2$, SO, S, O, $NR^{11}$, CO, Se, and any combination thereof;

$R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof;

$R^2$ is OH, H, $(CH_2)_nZH$, where Z=O, S, Se, or $NR^{11}$; or where $R^1$ and $R^2$ together represent =O;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, alkenyl, alkynyl, aryl or heteroaryl;

or where $R^5$ and $R^1$ together form a lactam or lactone;

$R^6$ is H, alkyl or $(CH_2)_nOH$;

$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_n[CH(ZH)]_nCH_2Y$, where Y is aryl, heteroaryl, alkyl or cyclic alkyl, heterocyclic, amino or guanidino, and Z=O, S, Se, or $NR^{11}$;

or where $R^7$ and $R^8$ together represent a cyclic alkyl group;

$R^9$ is H, alkyl, branched alkyl, cyclic alkyl, alkenyl, alkynyl, aryl, heteroaryl, $O(R^{11})_m$, $S(R^{11})_m$, $N(R^{11})_m(H)_{(2-m)}$, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

n=0, 1 or 2; and
m=0, 1 or 2.

In particular embodiments, disclosed compounds have the following formulae, where the substituents are as stated above:

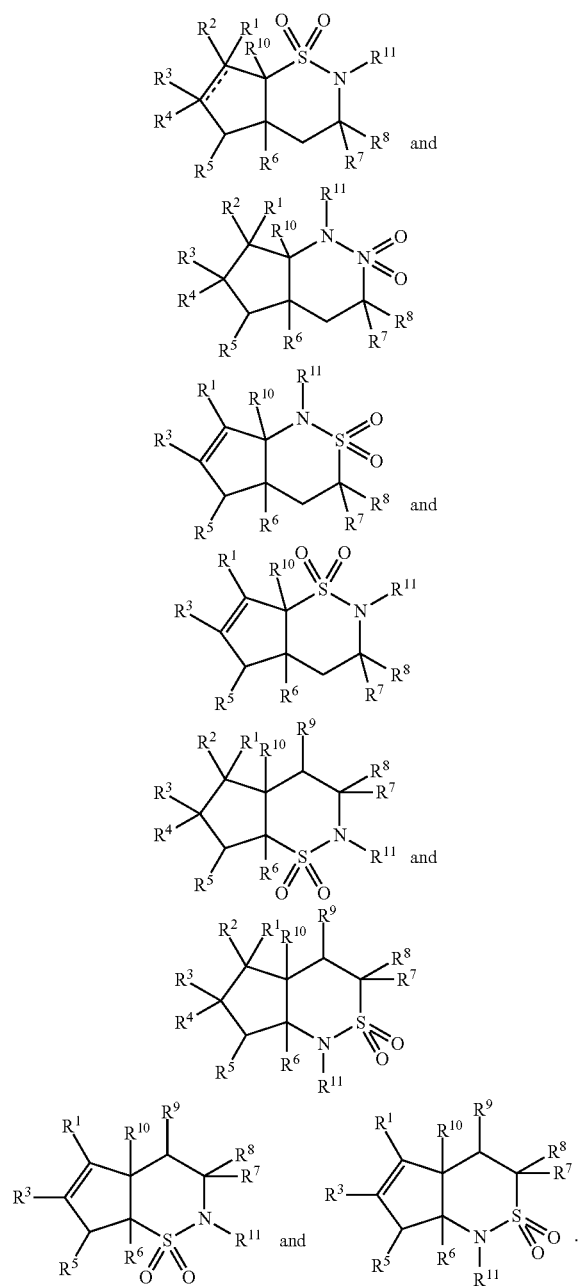

Any of the disclosed embodiments may be formulated as a pharmaceutically acceptable salt, prodrug, hydrate, or solvate.

Certain disclosed embodiments also relate to compositions for inhibiting influenza virus neuraminidase comprising a pharmaceutically acceptable carrier and an amount of a compound, as defined above, for effective inhibition of viral neuraminidase.

A further aspect of the disclosed embodiments concerns compositions for inhibiting bacterial sialidase virulence factors, including, but not limited to the *S. pneumonia* sialidases NanA, NanB, and NanC, wherein a compound as defined above is combined with a pharmaceutically acceptable carrier. These may include physiologically acceptable powders, liquids, salves, creams and ointments as a delivery method.

A further aspect of the disclosed embodiments concerns compositions leading to the inhibition of both viral neuraminidase and bacterial sialidase(s), leading to treatments for influenza-associated bacterial infections.

A further aspect of the disclosed embodiments relates to the administration of any of these compounds for the purposes of prophylaxis against influenza.

Certain disclosed embodiments also concern using the following chemical reactions, or reactions similar thereto as would be understood by a person of ordinary skill in the art, for preparing neuraminidase/sialidase inhibitors:

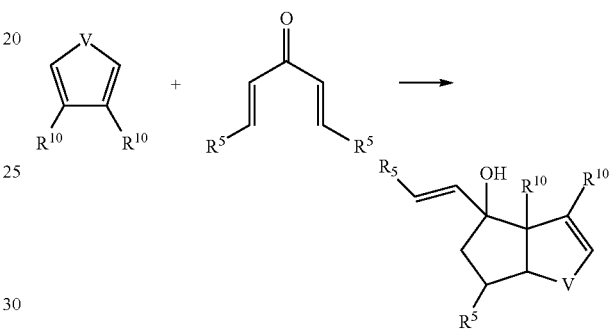

With reference to this scheme and the general formulae:

V is $SO_2$, SO, S, or CO;

$R^5$ represents a functional group known by those skilled in the art to be convertible to $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, alkenyl, alkynyl, branched alkyl, cyclic alkyl, aryl or heteroaryl;

$R^{10}$ is H, alkyl or a protected form of $(CH_2)_nOH$;

$R^{11}$ is H, alkyl, branched alkyl, cyclic alkyl, aryl or a heteroatom-containing moiety;

n=0, 1 or 2; and
m=0, 1 or 2.

A further aspect of disclosed embodiments relates to the use of chemical reactions similar to the following, for the purposes of the preparation of neuraminidase/sialidase inhibitors:

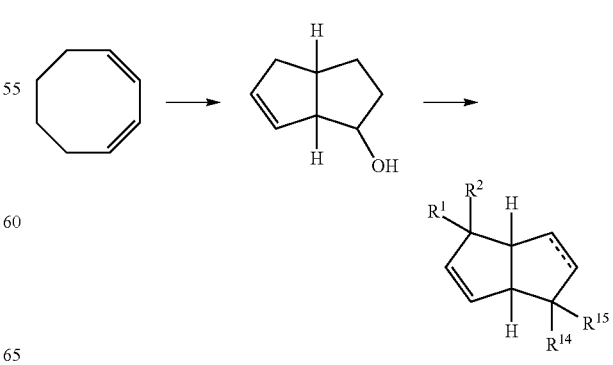

With reference to this scheme and the general formulae:

$R^{14}$ and $R^{15}$ independently are H, OH, a suitably protected derivative thereof, and any combination thereof;

or where $R^{14}$ and $R^{15}$ together represent =O.

A further aspect of the disclosed embodiments relates to intermediates represented by the following formulae for the preparation of neuraminidase/sialidase inhibitors:

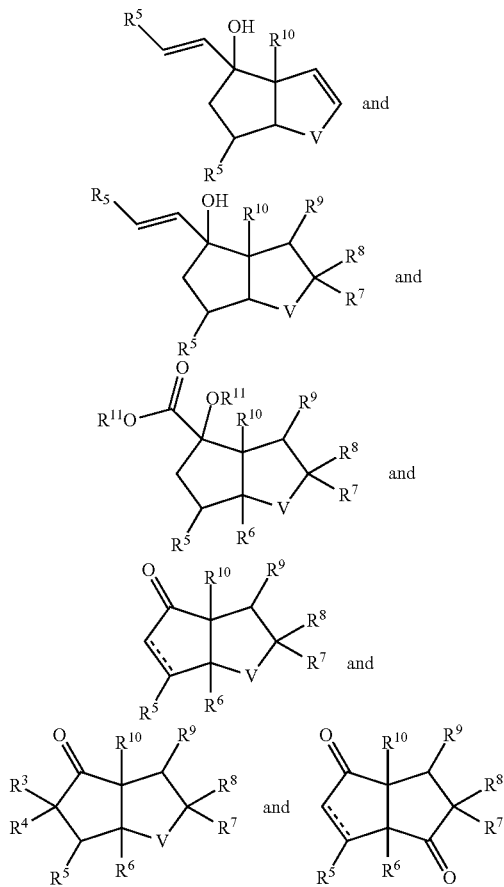

With reference to this scheme and the general formulae, V is $CHR^{12}$, $SO_2$, SO, S, or CO;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, aryl or heteroaryl;

$R^6$ is H, alkyl or $(CH_2)_nOH$;

$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, heterocyclic, amino or guanidino, and Z=O, S, Se, or $NR^{11}$;

or where $R^7$ and $R^8$ together represent a cyclic alkyl group;

$R^9$ is H, alkyl, branched alkyl, cyclic alkyl, aryl, heteroaryl, $O(R^{11})_m$, $S(R^{11})_m$, or $N(R^{11})_m(H)_{(2-m)}$;

$R^{10}$ is H, alkyl or $(CH_2)_nOH$;

$R^{11}$ is H, alkyl, branched alkyl, cyclic alkyl, aryl or a heteroatom-containing moiety;

$R^{12}$ is H, $(CH_2)_nZH$, $(CH_2)ZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

n=0, 1 or 2; and m=0, 1 or 2.

Disclosed embodiments also concern alternative ring systems accessible from those described above, using ring expansions or ring contractions (or other transformations) to arrive at larger or smaller bicyclic ring systems. These include, but are not limited to, structures represented by the following formula:

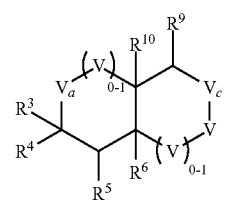

With reference to this general formula, V, $V_a$, and $V_c$ independently are selected from $CR^{11}R^{12}$, $C(R^{11})_2$, $C(R^{13})_2$, $SO_2$, SO, S, O, $NR^{11}$, CO, and Se;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)NHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, alkenyl, alkynyl, aryl or heteroaryl;

or where $V_a$ is $CR^{11}R^{12}$, $C(R^{11})_2$, or $C(R^{13})_2$, then $R^5$ and any one of $R^{11}$, $R^{12}$, or $R^{13}$ together form a lactam or lactone;

$R^6$ is H, alkyl or $(CH_2)_nOH$;

where $V_c$ is $CR^{11}R^{12}$, $C(R^{11})_2$, $C(R^{13})_2$, then any one of $R^{11}$, $R^{12}$, or $R^{13}$ together can form a cyclic alkyl;

$R^9$ is H, alkyl, branched alkyl, cyclic alkyl, aryl, heteroaryl, $O(R^{11})_m$, $S(R^{11})_m$, or $N(R^{11})_m(H)_{(2-m)}$;

$R^{10}$ is H, alkyl or $(CH_2)OH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof. The heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfonyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino;

n=0, 1 or 2; and m=0, 1 or 2.

Particular embodiments of the disclosed compounds have the following general formulae:

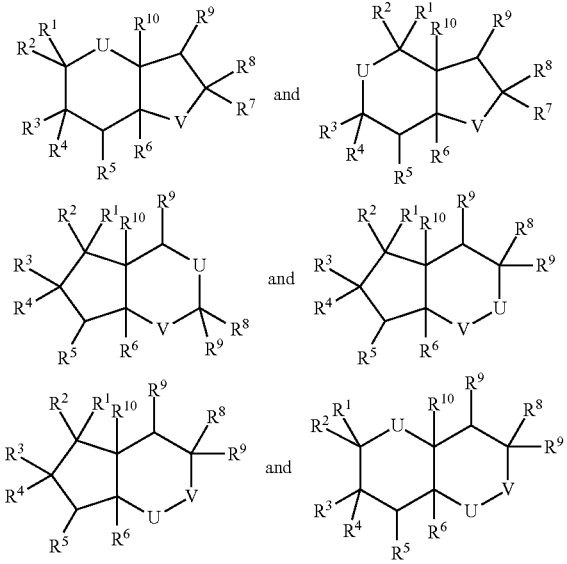

With reference to these general formulae,
V is $CHR^{12}$, $SO_2$, SO, S, or CO;
U is O, $NR^{11}$, $CHR^{11}$, or S;
$R^1$ is $CO_2H$, $(CH_2)CO_2H$, $(CH_2)_nOH$, tetrazolyl, $SO_2H$, $SO_3H$, $PO_3H_2$, or esters, amides, anhydrides or other protected forms thereof;
$R^2$ is OH, H, $(CH_2)_nZH$, where Z=O, S, Se, or $NR^{11}$;
or where $R^1$ and $R^2$ together represent =O;
$R^3$ and $R^4$ independently are H, alkyl, branched alkyl, aryl or heteroaryl;
or $R^3$ and $R^4$ together represent a cyclic alkyl group or =O;
$R^5$ is $NH_2$, $(CH_2)N(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)_nZ(R^{11})$, $(CH_2)_nZH$, where Z=O, S, Se, or $NR^{11}$; guanidino, substituted guanidino, alkyl, branched alkyl, cyclic alkyl, alkenyl, alkynyl, aryl or heteroaryl;
or where $R^5$ and $R^1$ together form a lactam or lactone;
$R^6$ is H, alkyl or $(CH_2)_nOH$;
$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, heterocyclic, amino or guanidino, and Z=O, S, Se, or $NR^{11}$;
or where $R^7$ and $R^8$ together represent a cyclic alkyl group;
$R^9$ is H, alkyl, branched alkyl, cyclic alkyl, aryl, heteroaryl, $O(R^{11}) S(R^{11})_m$, or $N(R^{11})_m(H)_{(2-m)}$;
$R^{19}$ is H, alkyl or $(CH_2)_nOH$;
$R^{11}$ is H, alkyl, branched alkyl, cyclic alkyl, aryl, heteroaryl, $(CH_2)_nY$, $(CH)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, amino or guanidino, and Z=O, S, Se, or $NR^{11}$;
$R^{12}$ is H, $(CH_2)_nZH$, $(CH_2)ZR^{11}$, $(CH_2)_nZ(CO)R^{11}$, $(CH_2)_n Z(SO_2)R^{11}$, $(CH_2)Z(CO)NH_2$, $(CH_2)Z(CO)OR^{11}$, or $(CH_2)_nZ(CNH)NH_2$, and Z=O, S, Se, or $NR^{11}$;
n=0, 1 or 2; and
m=0, 1 or 2.

Disclosed embodiments also concern heteroatom-substituted variants of those compounds described above. These include, but are not limited to, structures represented by the following formulae:

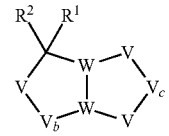

With respect to this general formula, V, $V_b$, and $V_c$ independently are selected from $CR^{11}R^{12}$, $C(R^{11})_2$, $C(R^{13})_2$, $SO_2$, SO, S, O, $NR^{11}$, CO, and Se; and W is $CHR^{10}$, $CR^{11}$, nitrogen, and any combination thereof;
$R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof;
$R^2$ is OH, H, $(CH_2)_nZH$, where Z=O, S, Se, or $NR^{11}$;
or where $R^1$ and $R^2$ together represent =O;
$R^{10}$ is H, alkyl or $(CH_2)_nOH$;
$R^{11}$ is H, alkyl, branched alkyl, cyclic alkyl, aryl, a heteroatom-containing moiety, and any combination thereof;
$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;
$R^{13}$ is H, alkyl, branched alkyl, cyclic alkyl, alkenyl, alkynyl, aryl, a heteroatom-containing moiety, and any combination thereof. The heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino;
or where $V_b$ is $CR^{11}R^{12}$, $C(R^{11})_2$, or $C(R^{13})_2$, then $R^1$ and any one of $R^{11}$, $R^{12}$, or $R^{13}$ together form a lactam or lactone;
or where $V_c$ is $CR^{11}R^{12}$, $C(R^{11})_2$, $C(R^{13})_2$, then any one of $R^{11}$, $R^{12}$, or $R^{13}$ together can form a cyclic alkyl;
n=0, 1 or 2; and
m=0, 1 or 2.

Particular embodiments have the following formulae:

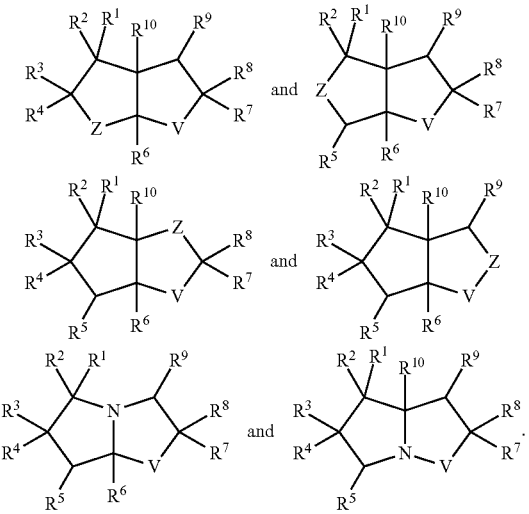

With reference to these general formulae,
V is $CHR^{12}$, $SO_2$, SO, S, or CO;

Z is O, S, Se, or $NR^{11}$;

$R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof;

$R^2$ is OH, H, $(CH_2)_nZH$, where Z=O, S, Se, or $NR^{11}$;

or where $R^1$ and $R^2$ together represent =O;

$R^3$ and $R^4$ independently are H, alkyl, branched alkyl, aryl or heteroaryl;

or $R^3$ and $R^4$ together represent a cyclic alkyl group or =O;

$R^5$ is $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, aryl or heteroaryl;

or where $R^5$ and $R^1$ together form a lactam or lactone;

$R^6$ is H, alkyl or $(CH_2)_nOH$;

$R^7$ and $R^8$ independently are H, alkyl, branched alkyl, cyclic alkyl, aryl, heteroaryl, $(CH_2)_nY$, $(CH_2)_nZY$, $(CH_2)CR^{11}Z$, $(CH_2)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, heterocyclic, amino or guanidino, and Z=O, S, Se, or $NR^{11}$;

or where $R^7$ and $R^8$ together represent a cyclic alkyl group;

$R^9$ is H, alkyl, branched alkyl, cyclic alkyl, aryl, heteroaryl, $O(R^{11})_m$, $S(R^{11})_m$, or $N(R^{11})_m(H)_{(2-m)}$;

$R^{10}$ is H, alkyl or $(CH_2)_nOH$;

$R^{11}$ is H, alkyl, branched alkyl, cyclic alkyl, aryl, heteroaryl, $(CH_2)_nY$, $(CH)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, amino or guanidino, and Z=O, S, Se, or $NR^{11}$;

$R^{12}$ is H, $(CH_2)_nZH$, $(CH_2)ZR^{11}$, $(CH_2)_nZ(CO)R^{11}$, $(CH_2)_nZ(SO_2)R^{11}$, $(CH_2)Z(CO)NH_2$, $(CH_2)Z(CO)OR^{11}$, or $(CH_2)_nZ(CNH)NH_2$, and Z=O, S, Se, or $NR^{11}$;

n=0, 1 or 2; and m=0, 1 or 2.

Exemplary compounds having structures within the scope of the disclosed embodiments are represented by the following:

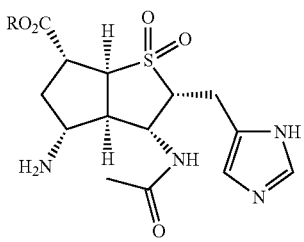

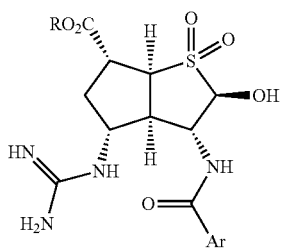

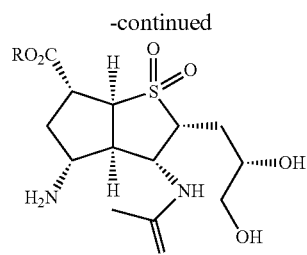

-continued

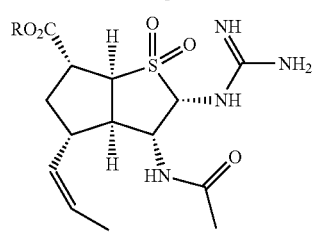

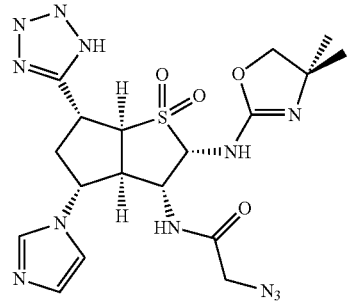

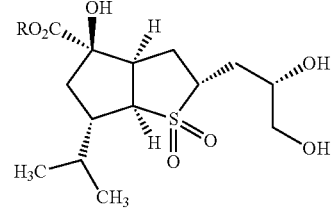

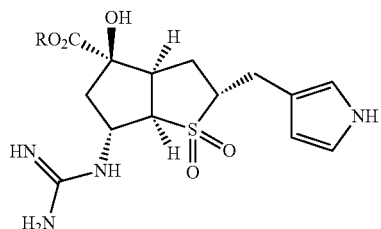

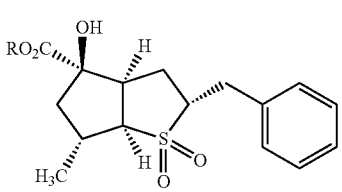

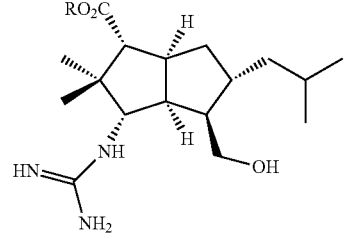

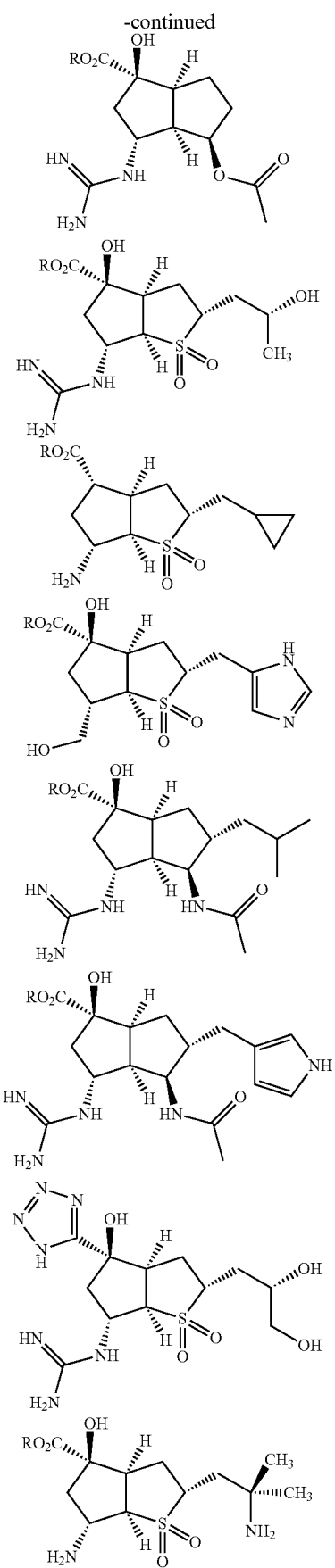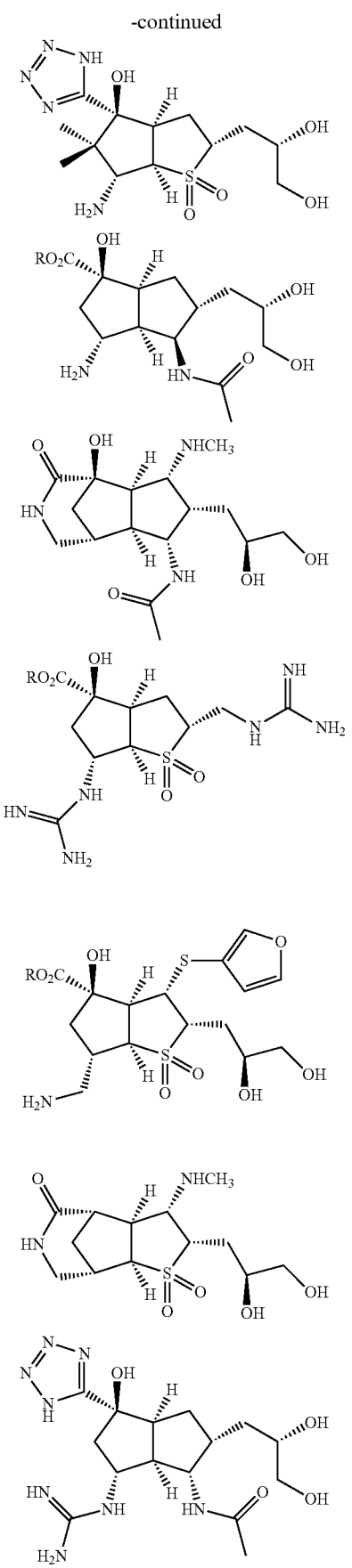

-continued

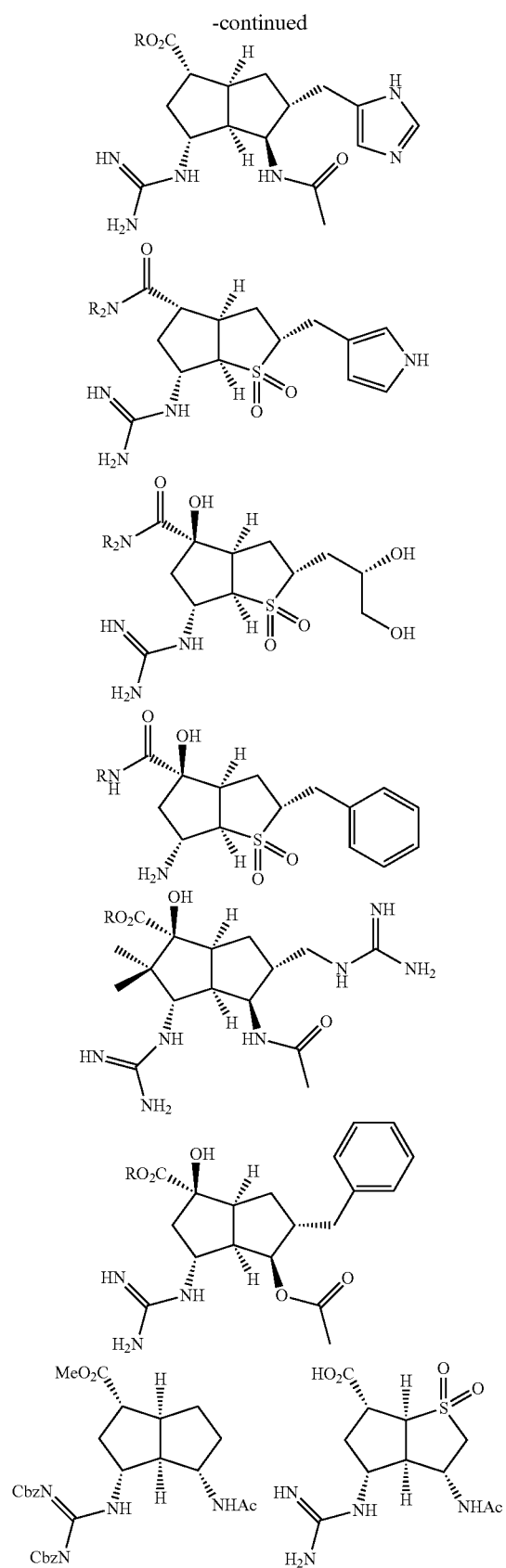

wherein R=H, alkyl, aryl, heteroaryl, or acyl; Ar=aryl or heteroaryl.

Any of the disclosed embodiments may be formulated as a pharmaceutically acceptable salt, prodrug, hydrate, or solvate.

DETAILED DESCRIPTION

I. Terms

Figure 1:
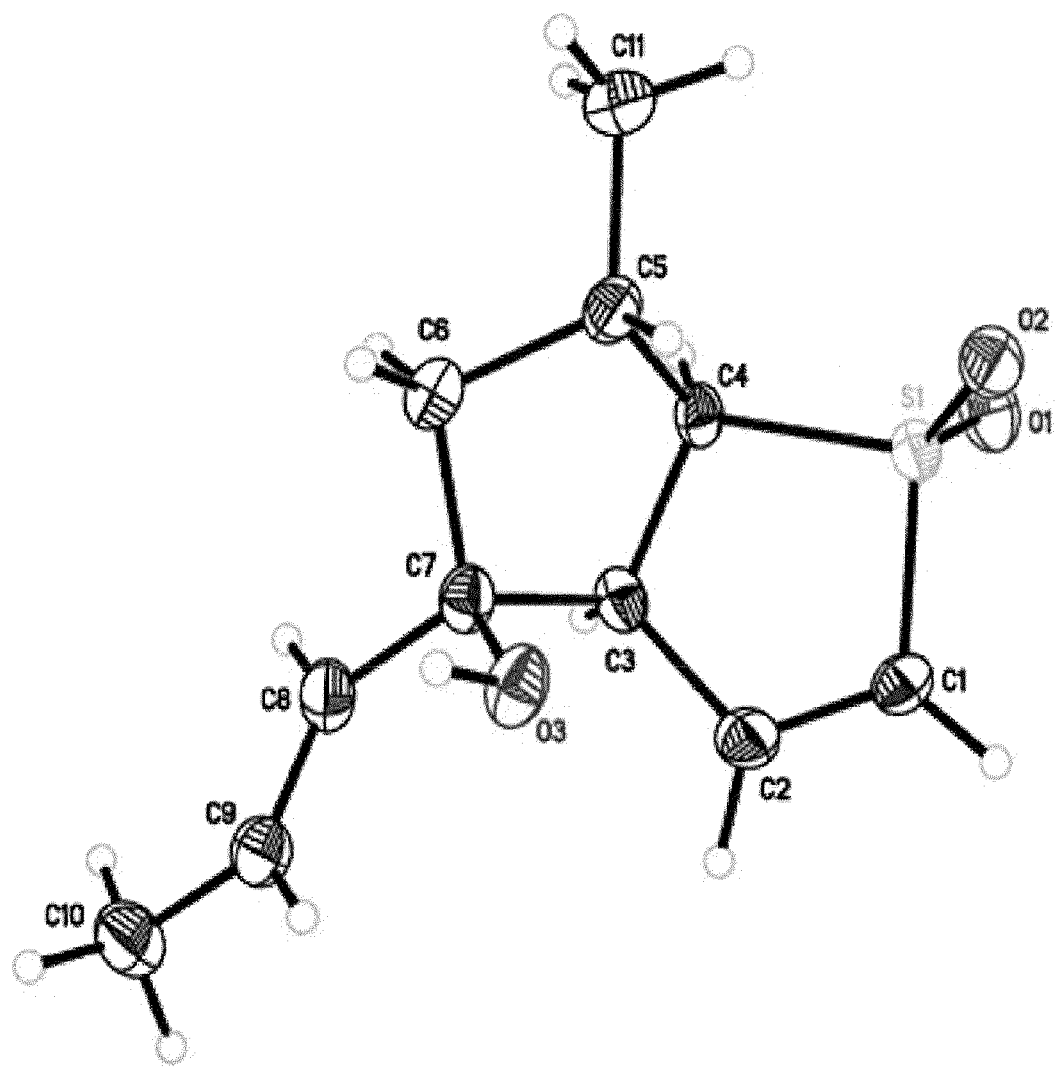
FIG. 1 is an image of the X-ray structure of bicyclic sulfone 14a from Example 2.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising the compound" includes single or plural molecules and is considered equivalent to the phrase "comprising at least one compound." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. A wavy line ("〜"), is used to indicate a bond disconnection, and a dashed line (" - - - ") is used to illustrate that a bond may or may not be formed at a particular position.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various examples of this disclosure, the following explanations of specific terms are provided:

Aldehyde: Is a carbonyl-bearing functional group having a formula

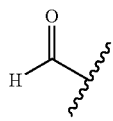

where the line drawn through the bond indicates that the functional group can be attached to any other moiety, but that such moiety simply is not indicated.

Aliphatic: A substantially hydrocarbon-based compound, or a radical thereof (e.g., $C_6H_{13}$, for a hexane radical), including alkanes, alkenes and alkynes, and further including straight- and branched-chain arrangements, and all stereo and position isomers as well.

Analog, Derivative or Mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc.

Arylalkyl: A compound, or a radical thereof ($C_7H_7$ for toluene) as a substituent bonded to another group, particularly other organic groups, containing both aliphatic and aromatic structures.

Carboxylic Acid: Refers to a carbonyl-bearing functional group having a formula

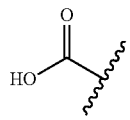

Cyclic: Designates a substantially hydrocarbon, closed-ring compound, or a radical thereof. Cyclic compounds or substituents also can include one or more sites of unsaturation, but does not include aromatic compounds. One example of such a cyclic compound is cyclopentadienone.

Dialkylidene: A compound having at least two carbon-carbon double bonds joined to the carbon atom of a carbonyl or sulfoxide group. This term also encompasses compounds having multiple conjugated carbon-carbon double bonds. Examples of dialkylidenes can have a formula

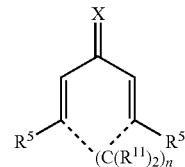

Where X is selected from oxygen and sulfur, $R^5$ can be a functional group known by those skilled in the art to be convertible to $NH_2$, guanidino, substituted guanidino, alkyl, alkenyl, alkynyl, branched alkyl, cyclic alkyl, aryl or heteroaryl, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$; where Z is O, S, Se, or $NR^{11}$; where n and m independently are 1-10; $R^{11}$ is H, alkyl, branched alkyl, cyclic alkyl, aryl or a heteroatom-containing moiety, or any combination thereof, and n is 1-10.

Diene: A diene, for purposes of the present invention, is any compound having at least two double bonds.

Ester: A carbonyl-bearing substituent having a formula

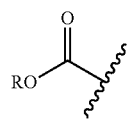

where R is virtually any group, including aliphatic, substituted aliphatic, aryl, arylalkyl, heteroaryl, etc.

Heteroaryl: Refers to an aromatic, closed-ring compound, or radical thereof as a substituent bonded to another group, particularly other organic groups, where at least one atom in the ring structure is other than carbon, and typically is oxygen, sulfur and/or nitrogen.

Heteroatom: Any atom that is not carbon or hydrogen. Examples include, but are not limited to, nitrogen, oxygen, sulfur, selenium, phosphorus, boron, chlorine, bromine, fluorine, and iodine.

Heteroatom-containing moiety: Refers to a functional group selected from, but not limited to, aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfinyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino;

Heterocyclic: Refers to a closed-ring compound, or radical thereof as a substituent bonded to another group, particularly other organic groups, where at least one atom in the ring structure is other than carbon, and typically is oxygen, sulfur and/or nitrogen.

Hydrate: A form of the disclosed compounds comprising one or more water molecules.

Ketone: A carbonyl-bearing substituent having a formula

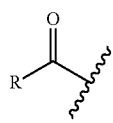

where R is virtually any group, including aliphatic, substituted aliphatic, aryl, arylalkyl, heteroaryl, etc.

Lactam: Refers to a cyclic amide formed from an amino carboxylic acid, typically having a ring size ranging from 4-membered to 8-membered. The lactam may be unsaturated or saturated and may comprise one or more heteroatoms.

Lactone: Refers to a cyclic ester formed from a hydroxy carboxylic acid, typically having a ring size ranging from 4-membered to 8-membered. The lactam may be unsaturated or saturated and may comprise one or more heteroatoms.

Lower: Refers to organic compounds having 10 or fewer carbon atoms in a chain, including all branched and stereochemical variations, particularly including methyl, ethyl, propyl, butyl, pentyl, hexyl, heptyl, octyl, nonyl, and decyl.

Inhibiting or Treating a Disease: Inhibiting the full development of a disease or condition, for example, in a subject who is at risk for a disease such as anthrax. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Mammal: This term includes both human and non-human mammals. Similarly, the term "subject" includes both human and veterinary subjects.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents. The term "pharmaceutically acceptable carrier" should be distinguished from "carrier" as described above in connection with a hapten/carrier conjugate or an antigen/carrier conjugate.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically Acceptable Salt: Typically, pharmaceutically acceptable salts are more soluble in aqueous solutions than the corresponding free acids and bases from which the salts are produced; however, salts having lower solubility than the corresponding free acids and bases from which the salts are produced may also be formed. Pharmaceutically acceptable salts are typically counterbalanced with an inorganic base, organic base, or basic amino acid if the salts are positively charged; or the salt is counterbalanced with an inorganic acid, organic acid, or acidic amino acid if they are negatively charged. Pharmaceutically acceptable salts can also be zwitterionic in form. Salts can be formed from cations. In particular disclosed embodiments, the cation may be a metal cation, such as sodium, potassium, aluminum, calcium, lithium, magnesium, zinc. The salt may also be formed from bases, such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. Other elements capable of forming salts are well-known to those skilled in the art, e.g. all elements from the main groups I to V of the Periodic Table of the Elements, as well as the elements from the subgroups I to VIII. Additionally, the pharmaceutically acceptable salt may be a form of the compound that imparts substantial crystallinity and substantially reduces hygroscopicity and solvation of the salt. Any chemical compound recited in this specification may alternatively be administered as a pharmaceutically acceptable salt thereof. "Pharmaceutically acceptable salts" are also inclusive of the free acid or base. Descriptions of suitable pharmaceutically acceptable salts can be found in *Handbook of Pharmaceutical Salts, Properties, Selection and Use*, Wiley VCH (2002), which we herein incorporate by reference.

Prodrug: Generally, a class of the disclosed compounds that may initially be in an inactive form and may be converted into an active form in the body by metabolic processes.

Solvate: A form of the disclosed compounds wherein the compound is solvated, e.g. combined with solvent molecules. The solvent can be organic or inorganic. Some examples of solvents include, but are not limited to methanol, N,N-dimethylformamide, tetrahydrofuran, dimethylsulfoxide, water, etc.

Substituted: A fundamental compound, such as an aryl or aliphatic compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a long-chain hydrocarbon may have a substituent bonded thereto, such as an aryl group, a cyclic group, a heteroaryl group or a heterocyclic group.

Therapeutically Effective Amount: A quantity of a specified agent sufficient to achieve a desired effect in a subject being treated with that agent. For example, this may be the amount of a conjugate useful in increasing resistance to, preventing, ameliorating, and/or treating infection and disease. Ideally, a therapeutically effective amount of an agent is an amount sufficient to increase resistance to, prevent, ameliorate, and/or treat infection and without causing a substantial cytotoxic effect in the subject. The effective amount of an agent useful for increasing resistance to, preventing, ameliorating, and/or treating infection and disease in a subject will be dependent on the subject being treated, the severity of the affliction, and the manner of administration of the therapeutic composition.

II. Pharmaceutical Formulations

One aspect of the composition of the disclosed compounds comprises of one or more pharmaceutically acceptable carriers. One or more of the disclosed compounds are administered by any route appropriate to the condition to be treated or sample to be tested. Examples include but are not limited to oral, rectal, nasal, topical (including buccal and sublingual), vaginal and parenteral (including subcutaneous, intramuscular, intravenous, intradermal, intrathecal and epidural).

In particular embodiments, the compounds are presented as pharmaceutical formulations. The formulations comprise at least one active ingredient, as described herein, with one or more acceptable carriers therefor and optionally other therapeutic ingredients or biologically acceptable materials as disclosed herein.

In other embodiments, acceptable carriers are defined as a compound or molecule compatible with the other ingredients of the formulation and substantially physiologically innocuous to the recipient thereof.

Biologically acceptable materials include, but are not limited to carriers, diluents, adjuvants, excipients, binders, fillers, lubricants, osmotic agents, flavoring agents, other active ingredients, and combinations thereof. Examples of carriers can include, without limitation, solvents, saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophobic carriers, fat emulsions, lipids, PEGylated phopholids, polymer matrices, biocompatible polymers, lipospheres, vesicles, particles, and liposomes, or combinations thereof. Examples of excipients include stabilizing agents, solubilizing agents, surfactants, buffers, antioxidants and preservatives, tonicity agents, bulking agents, lubricating agents, emulsifiers, suspending agents, viscosity agents, inert diluents, fillers, disintegrating agents, binding agents, wetting agents, lubricating agents, antibacterials, chelating agents, sweetners, perfuming agents, flavouring agents, coloring agents, administration aids, or combinations thereof. Examples of diluents include sodium carbonate, calcium carbonate, sodium phosphate, calcium phosphate, lactose, or combinations thereof. Examples of osmotic agents include sodium chloride, glycerol, sorbitol, xylitol, glucose, or combinations thereof. Binders can include acacia gum, starch, gelatin, sucrose, polyvinylpyrrolidone (Providone), sorbitol, or tragacanth methylcellulose, sodium carboxymethylcellulose, hydroxypropyl methylcellulose, ethylcellulose, or combinations thereof. Examples of fillers can include calcium phosphate, glycine, lactose, maize-starch, sorbitol, sucrose, or combinations thereof. Exemplary lubricants include magnesium stearate or other metallic stearates, stearic acid, polyethylene glycol, waxes, oils, silica and colloical silica, silicon fluid, talc, or combinations thereof. Flavoring agents can be peppermint, oil of wintergreen, fruit flavoring, or combinations thereof.

An effective amount of the disclosed compounds can depend at least on the nature of the condition being treated, toxicity, whether the compound is being used prophylactically (lower doses) or against an active influenza infection, the method of delivery, and the pharmaceutical formulation, and will be determined by the clinician using conventional dose escalation studies.

Expected dosage amounts are to be from greater than 0 to about 1000 mg/kg body weight per day, typically, from about greater than 0 to about 10 mg/kg body weight per day, more typically, from about greater than 0 to about 5 mg/kg body weight per day, and even more typically, from about greater than 0 to about 0.5 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

In a further aspect, the pharmaceutical formulations are for both veterinary and human use.

In a further aspect, the pharmaceutical formulations may be presented in unit dosage form and may be prepared by any methods known to a person of ordinary skill in the art of pharmacy.

III. Methods of Inhibiting Neuraminidase

Another aspect concerning the disclosed embodiments relates to methods of inhibiting the activity of neuraminidase comprising treating a sample suspected of containing neuraminidase with a compound and/or composition of the disclosed compounds. In particular disclosed embodiments, the method comprises administering an effective amount of one or more of the disclosed compounds In a further aspect, samples suspected of containing neuraminidase include natural or man-made materials. Examples include but are not limited to: living organisms; tissue or cell cultures; biological samples such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a glycoprotein or any desired biological molecule.

In a further aspect, the sample contains an organism which produces neuraminidase. Examples include but are not limited to a pathogenic organism such as a virus or bacterium.

In a further aspect, the inhibitory activity of disclosed compound extends to neuraminidase molecules, including but not limited to, neuraminidase molecule variants such as the H274Y mutant.

In a further aspect, the inhibitory activity of the compound extends to neuraminidase molecules expressed by various pathogenic strains of influenza, including but not limited to H1N1, H3N2, H5N1, H1N2, H2N2, H7N7, N9N2, H7N2, H7N3, and H10N7.

In a further aspect, the samples are in any medium including water, organic solvent, and organic solvent/water mixtures. Examples include but are not limited to living organisms, such as humans and animals and any man made materials such as cell cultures.

In a further aspect, the activity of neuraminidase after administering a disclosed compound and/or composition can be observed or monitored by any quantitative, qualitative and semi-quantitative method. This includes but is not limited to observation of the physiological properties of a living organism.

A further aspect of the disclosed embodiment relates to the use of drug conjugates containing one or more of the compounds described here, where the one or more compounds is coupled to a specific binding moiety, a signal generating moiety, or combinations thereof. In particular disclosed embodiments, the one or more compounds may be covalently or non-covalently bound to the specific binding moiety. The specific binding moiety may be selected from an antibody, protein, nucleic acid, or other macromolecules/aggregates. The signal generating moiety may be selected from an enzyme, a chromogenic compound, a fluorogenic compound, or lumogenic compound. In certain disclosed embodiments, the signal generating moiety is a nanoparticle. The disclosed compound and the specific binding moiety may coupled to each other directly or through a linker. The linker may be aliphatic or heteroaliphatic. In certain disclosed embodiments, the linker can be homofunctional or heterobifunctional.

A further aspect of the disclosed embodiment relates to the use of molecules described here present in liposomes, vesicles, micelles, dendrimers, biodegradable particle, or other delivery agents.

IV. Compound Metabolites

Another aspect associated with disclosed embodiments is directed to in vivo metabolic products of the compounds described herein.

In other embodiments, the metabolic product of the compound described herein results from oxidation, reduction, hydrolysis, amidation, and/or esterification of disclosed embodiments of the compounds, including but not limited to any product of enzymatic process of the administered compound. The products of the compound, so long as they are not otherwise found in vivo, are useful in diagnostic assays for therapeutic dosing of the disclosed compounds even if they possess no neuraminidase inhibitory activity of their own.

V. Compounds Derived from Alternative Methods

In other particular embodiments ring expansions or ring contractions (or other transformations) can be used to synthesize the disclosed compounds.

Other embodiments relate to heteroatom-substituted variants of the disclosed compounds, which are synthesized utilizing various chemical synthesis methodologies. The compounds are further considered to be additional embodiments of the disclosed compounds.

VI. Exemplary Methods for Making Disclosed Compounds

Disclosed embodiments also concern making the disclosed compounds, and compositions comprising the compounds. The compounds and/or compositions are prepared by applicable variety of organic synthetic techniques, as will be understood by a person of ordinary skill in the art based on the following discussion. These include, but are not limited to, condensations, cycloadditions or alkylations from any applicable acyclic, monocyclic or bicyclic precursors. These also include degradations from compounds of higher molecular weight.

An exemplary method for preparing disclosed compounds is provided in Scheme 1 below.

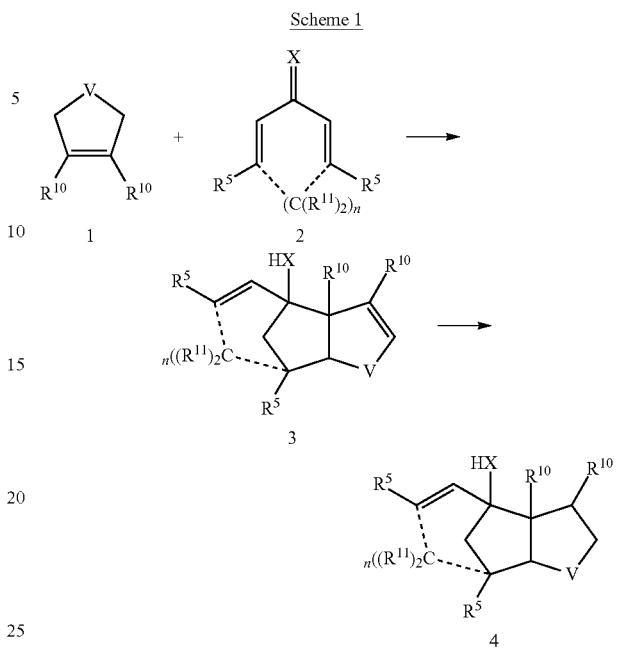

A method for making compounds having a general formula 4 is disclosed, wherein $R^5$ can be a functional group known by those skilled in the art to be convertible to $NH_2$, guanidino, substituted guanidino, carboxyl, phosphonyl, alkyl, alkenyl, alkynyl, branched alkyl, cyclic alkyl, aryl or heteroaryl, $(CH_2)_nN(R^{11})_m(H)_{(2-m)}$, $(CH_2)_nNHC(O)(R^{11})$, $(CH_2)_nNC(=NR^{11})N(R^1)_m(H)_{(2-m)}$, $(CH_2)_nNHC(O)Z(R^{11})$, $(CH_2)_nZH$; where Z is O, S, Se, or $NR^{11}$; where n and m independently are 1-10; $R^{11}$ is H, alkyl, branched alkyl, cyclic alkyl, aryl or heteroaryl; $R^{10}$ is H, alkyl or any protected form of $(CH_2)_nOH$, or is a functional group that can be converted into $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$; where Z is O, S, Se, or $NR^{11}$; V is any heteroatom, carbonyl, sulfonyl, or sulfone; and X is any heteroatom, such as oxygen or sulfur, or any combination thereof. An acidic cyclic starting material 1 is added to compound 2 using a base, wherein the addition can occur directly or in a conjugate fashion. Compound 2 is typically selected to comprise a heteroatom-containing dialkylidene compound, such as, but not limited to, a dialkylidene ketone or dialkylidene sulfoxide. After addition, a second treatment of an intermediate with base induces rearrangement and cyclization to provide bicycle 3. Bicycle 3 can be reduced to saturated bicycle 4 using a reducing agent known to a person of ordinary skill in the art to be suitable for reducing olefins.

Another exemplary method for preparing disclosed compounds is provided in Scheme 2.

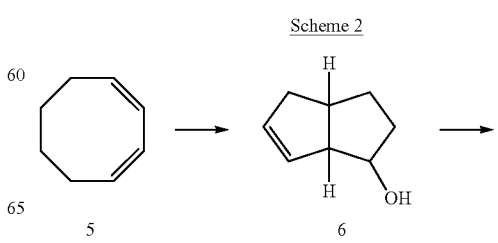

-continued

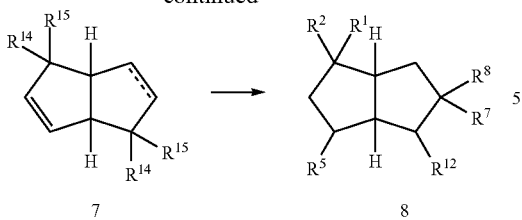

A method for making compounds having a general formula 8 is disclosed, wherein $R^{14}$ and $R^{15}$ are independently H, OH, or a suitably protected derivative thereof, or else $R^{14}$ and $R^{15}$ together represent =O, and where:

$R^1$ is $CO_2H$, $(CH_2)_nCO_2H$, $(CH_2)OH$, tetrazolyl, $SO_2H$, $SO_3H$, $PO_3H_2$, or esters, amides, anhydrides or other protected forms thereof;

$R^2$ is OH, H, $(CH_2)_nZH$, where Z=O, S, Se, or $NR^{11}$;

$R^5$ is $NH_2$, $(CH_2)_nN(R^{11})_4H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z=O, S, Se, or $NR^{11}$; guanidino, substituted guanidino, alkyl, branched alkyl, cyclic alkyl, aryl or heteroaryl;

$R^7$ and $R^8$ independently are H, alkyl, branched alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_n[CH(ZH)]_mCH_2Y$, where Y is aryl, heteroaryl, alkyl or cyclic alkyl, heterocyclic, amino or guanidino, and Z=O, S, Se, or $NR^{11}$, or where $R^7$ and $R^8$ together represent a cyclic alkyl group;

$R^{11}$ is H, alkyl, branched alkyl, cyclic alkyl, aryl, a heteroatom-containing moiety, or any combination thereof;

$R^{12}$ is H, $(CH_2)_nZH$, $(CH_2)ZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

n=0, 1 or 2;

m=0, 1 or 2;

In the method illustrated in Scheme 2, a cyclic diene, such as cyclooctadiene 5, can be oxidized using reagents known to a person of ordinary skill in the art, such as, but not limited to, peracids and peroxides. Rearrangement can be induced by treating the oxidized intermediate with a base to make bicycle 6. Both steps can be carried out using the method of Oger, Brinkmann, Bouazzaoui, Durand and Galeno, or by other means known to a person of ordinary skill in the art. Particular embodiments concern using resolution methods of individual enantiomers of compound 6, such as enzymatic resolution, or crystallographic resolution to obtain enantiomerically pure forms of compound 6. Further oxidative transformations of the kind familiar to those skilled in the art are sufficient to make 7, after which derivatization can provide functionalized bicycle 8. Methods leading to tricyclic or polycyclic analogues of 8 are also contemplated by the disclosed methods.

A particular working embodiment is illustrated in Scheme 3. This embodiment concerned a base-induced addition of diene 9 to commercially available 10, making isomeric sulfones 12 or 13, depending upon the temperature at which the reaction was quenched. In other embodiments, compound 12 can be converted to 13 by treatment with base. Bicycle 14 can be made by treating 13 with lithium hexamethyldisilazide. Reduction of 14 can be carried out using an appropriate reducing agent, such as lithium aluminium hydride or sodium bis(2-methoxyethoxy)aluminumhydride, to make bicyclic sulfone 15 in ca. 50% overall yield from 10. Alternatively, nucleophiles other than hydride can be added to generate 16 in similar overall yield.

Scheme 3

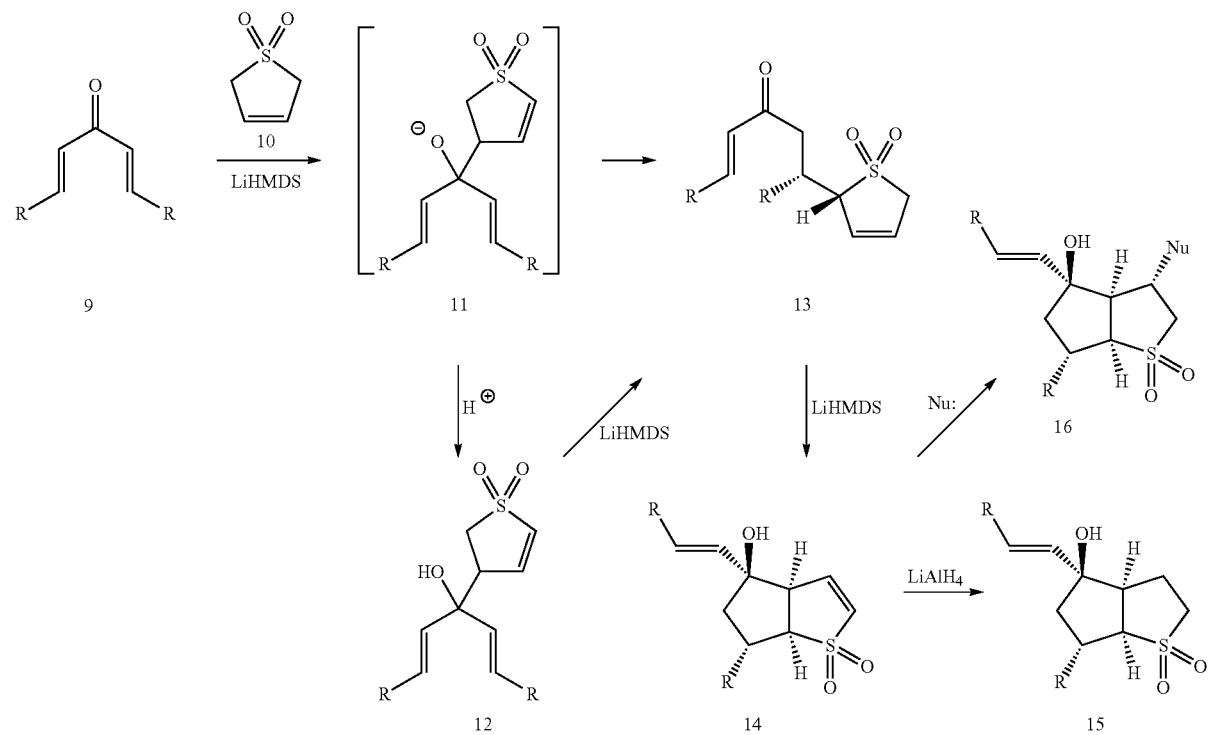

With reference to Scheme 3, a more particular process comprised treating a solution of ketone 9a (R=CH₃) and sulfone 10 with LiHMDS at −78° C. This resulted in attack from the γ-position of the sulfone anion directly to the ketone of 9a. The reaction was quenched at low temperature, and the major isolated product was the tertiary alcohol 12a. Treating 12a with a second equivalent of LiHMDS initiated an anionic oxy-Cope rearrangement, affording keto-sulfone 13a as a single diastereomer. Molecule 13a was also accessed in a single step, when a mixture of 9a, 10 and LiHMDS was warmed to room temperature prior to aqueous workup. By either preparation, sulfone 13a was prepared as a single diastereomer. Reaction of keto-sulfone 13a with more LiHMDS resulted in a second attack from the γ-position of the sulfone to the ketone, leading to the formation of alcohol 14a, again as a single diastereomer. An image of the X-ray structure of alcohol 14a is illustrated in FIG. 1. The electrophilic vinyl sulfone function was reduced with LiAlH₄, affording 15a in a 50% yield over 3 steps (average of 79% per step). As a further example, methylamine was added to vinyl sulfone 14a to provide 16a (R=CH₃; Nu=HNCH₃) in quantitative yield.

Scheme 4 illustrates another general method for making disclosed compounds.

With reference to the general method of Scheme 4, the functional groups of bicycle 4 can be manipulated through many different reaction conditions. Certain disclosed embodiments concern using an oxidative cleavage of the exocyclic olefin, followed by oxidation to make bicycle 17. With reference to bicycle 17, $R^5$ can be a functional group known by those or ordinary skill in the art to be convertible to $NH_2$, guanidino, substituted guanidino, alkyl, alkenyl, alkynyl, branched alkyl, cyclic alkyl, aryl or heteroaryl, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is O, S, Se, or $NR^{11}$; where n and m independently are 1-10; $R^{11}$ is H, alkyl, branched alkyl, cyclic alkyl, aryl, a heteroatom-containing moiety, or combinations thereof; $R^{10}$ is H, alkyl or any protected form of $(CH_2)_nOH$; V is any heteroatom, particularly oxygen or sulphur, and carbonyl, sulfonyl, or sulfone; and X is any heteroatom, such as oxygen or sulphur; and any and all combinations thereof. Another method concerns alkylation of the bicycle using alkylation conditions known to a person of ordinary skill in the art, such as a base and an appropriate alkylating reagent. After alkylation, the same oxidative cleavage and oxidation steps can be used to obtain bicycle 18. Other embodiments of the disclosed method con- Scheme 4

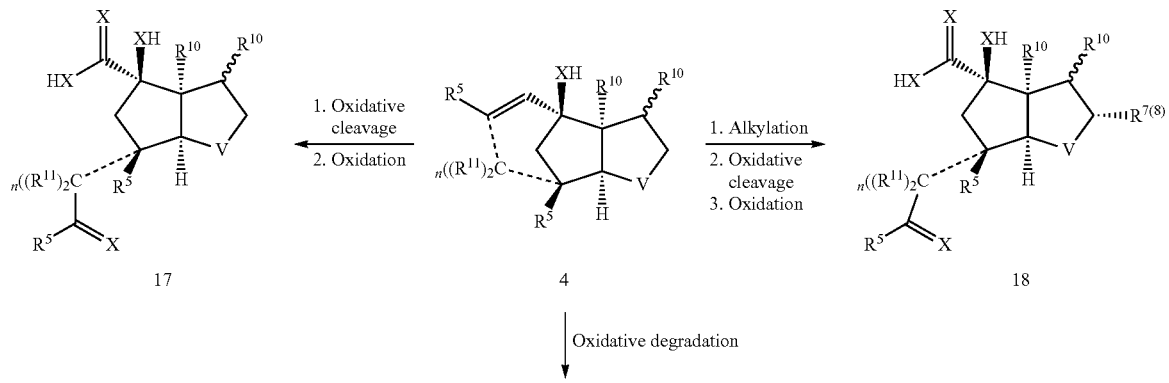

Oxidative degradation

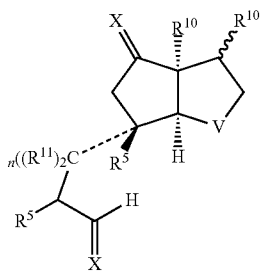

19 cern an oxidative degradation step to remove the exocylic olefin to provide bicycle 19. Any of the disclosed methods can be employed in the stated sequence, or any combination thereof.

Scheme 5 provides exemplary reaction conditions to implement the general concepts of Scheme 4.

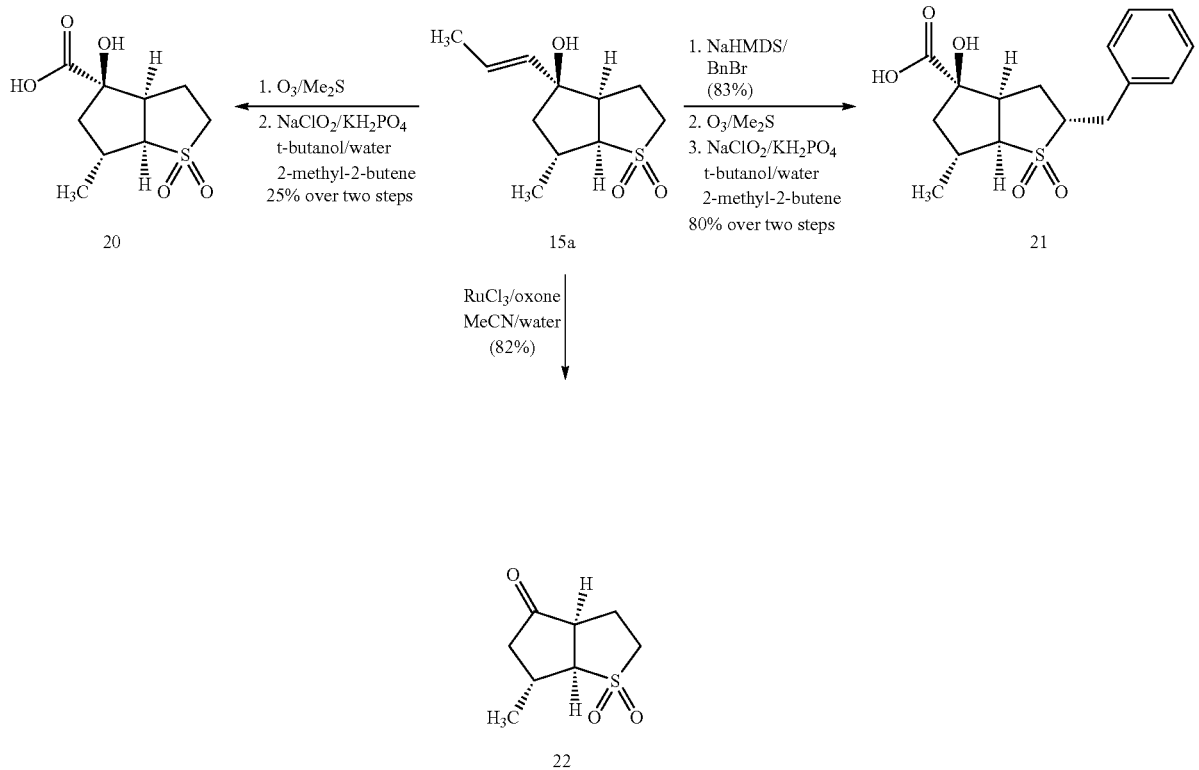

Figure 4:
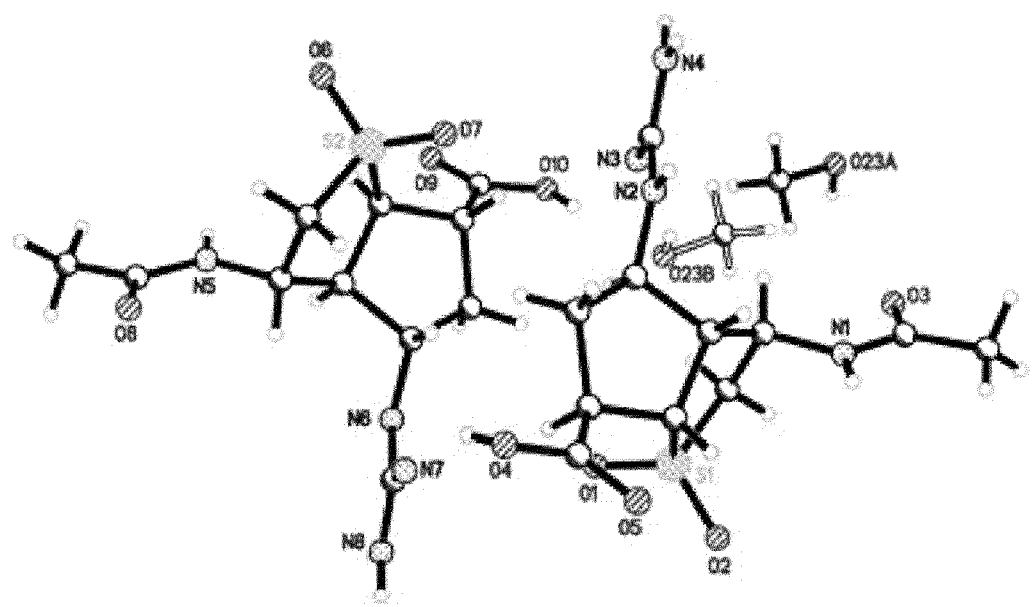
FIG. 4 is an image of the X-ray structure of guanidino acid 32 from Example 21.

Scheme 5

20, 15a, 21, 22

In particular working embodiments, sulfone 15a was converted through the steps stated above to various products. Cleavage of the exocyclic olefin was accomplished following a two-step ozonolysis/Pinnick procedure to provide 20, which exhibited dose-dependent inhibition of commercially available recombinant H1N1 neuraminidase, as indicated in Table 1, disclosed herein. Alternatively, alkylation at the position adjacent to the sulfone using benzyl bromide prior to oxidative cleavage resulted in forming 21, as a single diastereomer. In cases where the C-4 ketone is required, either as an inhibitor or a synthetic intermediate, the exocyclic olefin can by completely cleaved by treatment with $RuCl_3$ and oxone. Treating 15a with $RuCl_3$ and oxone led to the formation of ketone 22.

Further exemplary reactions are provided in Scheme 6. An image of the X-ray structure of the ethyl ester of compound 27, which was crystallized as the hydrochloride salt, is illustrated in FIG. 3.

Scheme 6

9b, 14b 33 34
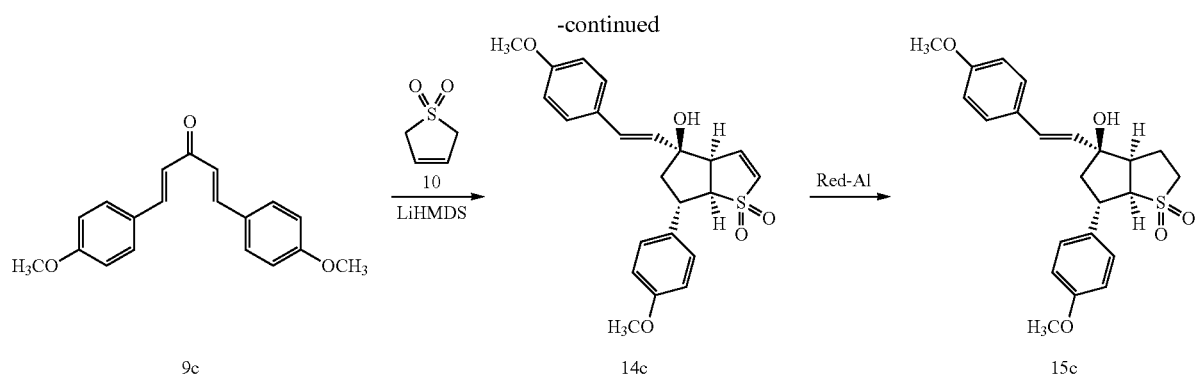
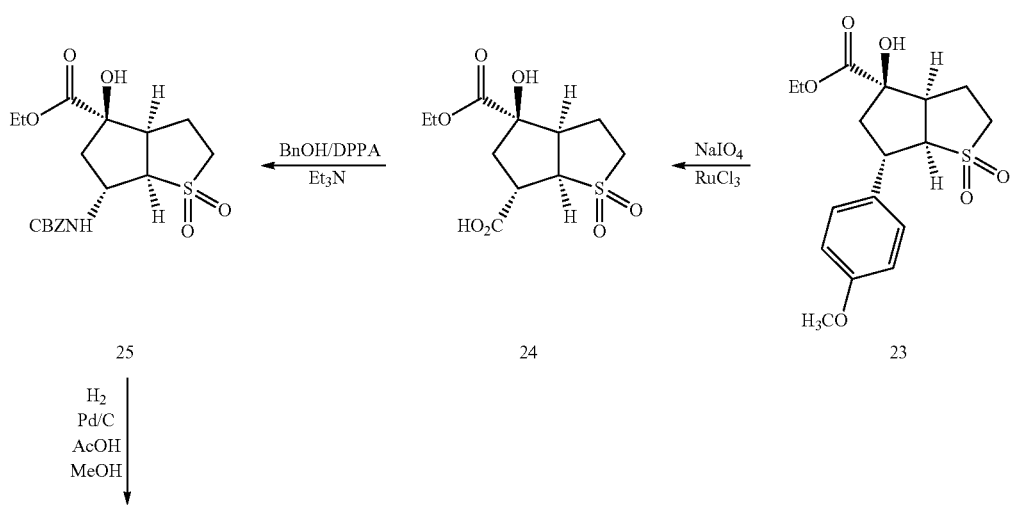
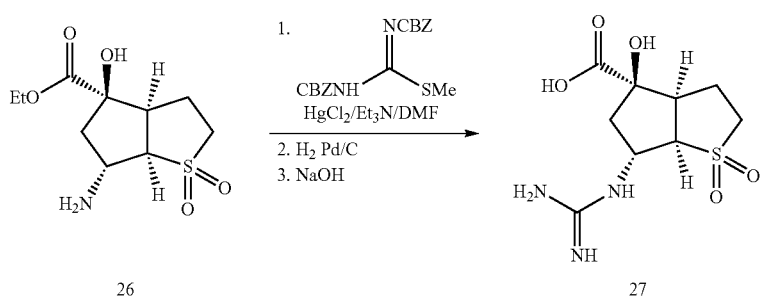
Further exemplary reactions are provided in Scheme 7. An image of the X-ray structure of compound 32 is illustrated in FIG. 4.

Scheme 7

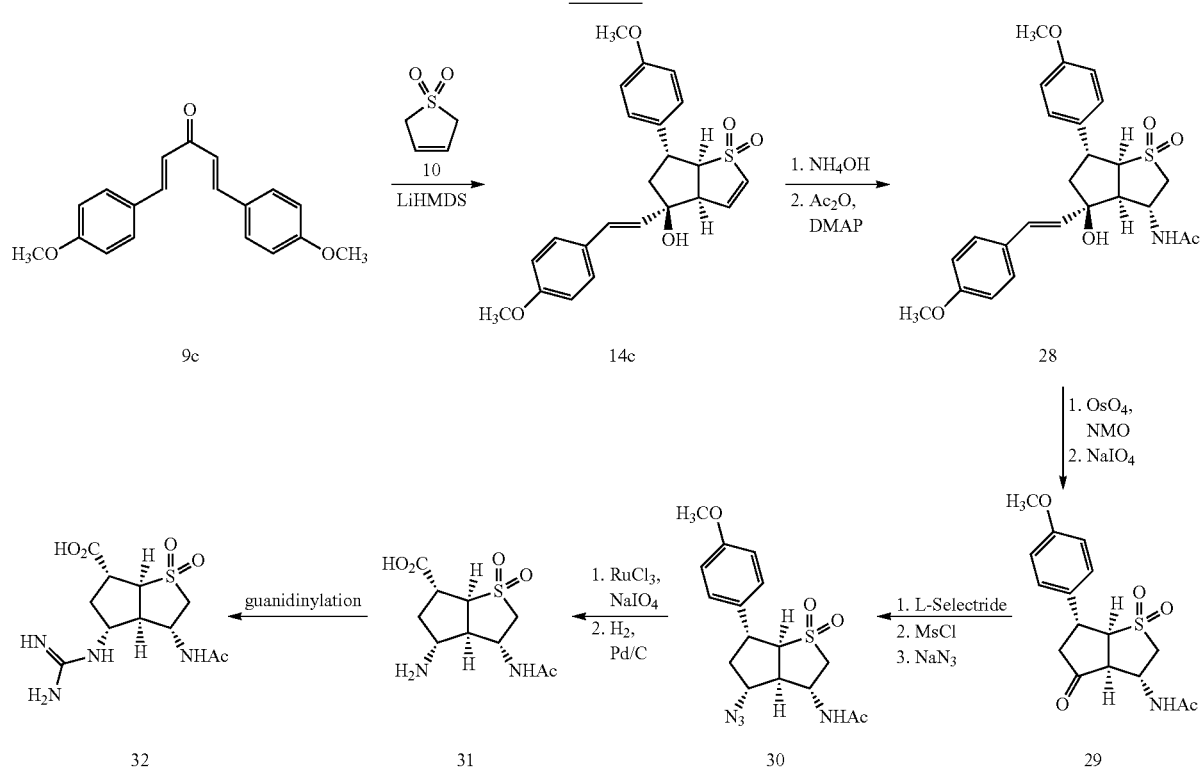

Scheme 8 illustrates another general method for making the disclosed compounds.

Scheme 8

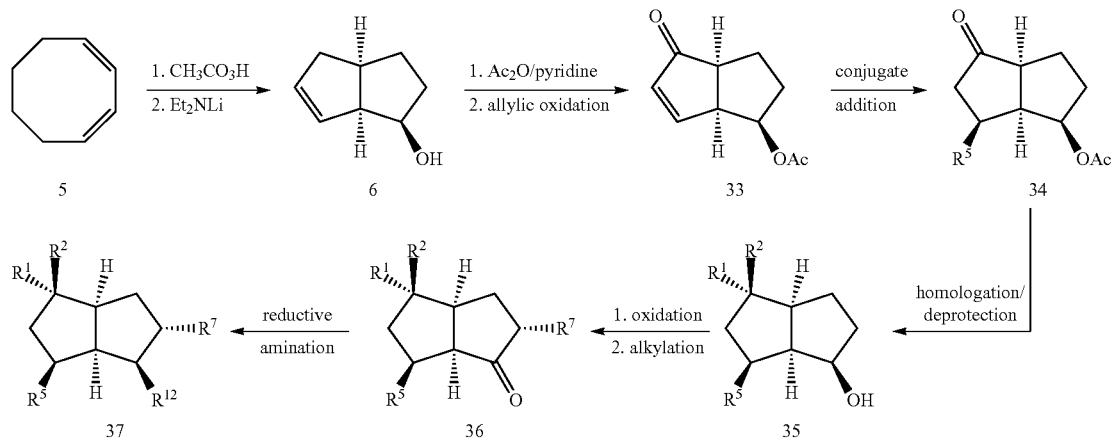

With reference to the general method of Scheme 8, oxidation and rearrangement of diene 5 using the method of Oger, Brinkmann, Bouazzaoui, Durand and Galeno can afford alcohol 6. Using a modified method to that of Bedekar et al., acetylation and allylic oxidation of 6 can provide 33. Reagents for allylic oxidation include those known to a person of ordinary skill in the art, such as, but not limited to, a metal-containing oxidant or an organic oxidant. Examples of metal-containing oxidants include, but are not limited to, chromium oxidants, manganese oxidants, rhodium oxidants, and copper oxidants. An example of an organic oxidant is selenium dioxide. Chemoselective derivatization using methodology familiar to those skilled in the art can provide access to compounds 34-37, each of which may be useful as an inhibitor of viral, or bacterial sialidases, or may be a synthetic precursor for other inhibitors. Those skilled in the art will recognize that some or all of the intermediates shown in Scheme 7 may require additional deprotection steps or other manipulations prior to their use as inhibitors.

With reference to this general formulae in Scheme 8, $R^1$ is $CO_2H$, $(CH_2)_nCO_2H$, $(CH_2)_nOH$, tetrazolyl, $SO_2H$, $SO_3H$, $PO_3H_2$, or esters, amides, anhydrides or other protected forms thereof; R² is H, OH, (CH₂)ₙZH, or protected forms thereof, where Z=O, S, Se, or NR¹¹; R⁵ is NH₂, (CH₂)ₙN(R¹¹)ₘ(H)₍₂₋ₘ₎, (CH₂)NHC(O)(R¹¹), (CH₂)ₙNC(=NR¹¹)N(R¹¹)ₘ(H)₍₂₋ₘ₎, (CH₂)ₙNHC(O)Z(R¹¹), (CH₂)ₙZH, or protected forms thereof, where Z=O, S, Se, or NR¹¹; guanidino, substituted guanidino, alkyl, branched alkyl, cyclic alkyl, alkenyl, alkynyl, aryl or heteroaryl; R⁷ is alkyl, branched alkyl, cyclic alkyl, aryl, heteroaryl, (CH₂)ₙY, (CH₂)ₙZY, (CH₂)ₙCR¹¹Z, (CH₂)₂ZH, [CH₂]ₙ[CH(ZH)]ₙCH₂ZH, [CH₂]ₙ[CH(ZH)]ₘCH₂Y, where Y is aryl, heteroaryl, alkyl or cyclic alkyl, heterocyclic, amino or guanidino, and Z=O, S, Se, or NR¹¹; R¹¹ is H, alkyl, branched alkyl, cyclic alkyl, aryl or heteroaryl; R¹² is H, (CH₂)ₙZH, (CH₂)ZR¹¹, (CH₂)ₙZ(CO)R¹¹, (CH₂)ₙZ(SO₂)R¹¹, (CH₂)Z(CO)NH₂, (CH₂)Z(CO)OR¹¹, or (CH₂)ₙZ(CNH)NH₂, and Z=O, S, Se, or NR¹¹; n=0, 1 or 2; and m=0, 1 or 2.

Scheme 9 illustrates an alternative means of accessing similarly-functionalized compounds to those indicated in Scheme 8.

In this example, intermediate 6 was only partially oxidized to allylic alcohol 38. Following protecting group exchange, the free alcohol in 39 was exchanged for an acetamide group, with inversion of stereochemistry. Hydroboration, Mitsunobu inversion with HN₃ and reduction of the intermediate azide yielded amine 42, which was subjected to guanidinylation, deprotection and oxidation to access 44, from which homologation provided neuraminidase inhibitor 45.

Exemplary methods for preparing the disclosed compounds as shown in Schemes 3, 5, 6, 7 and 9 are provided in the experimental section below. In each of the schemes provided herein it may be advantageous to separate reaction products from one another and/or starting materials. The desired products of each step or series of steps are separated and/or purified to the desired degree of homogeneity by the techniques common in the art. Examples include but are not limited to multiphase extraction, crystallization from a solvent or solvent mixture, distillation, sublimation, or chromatography.

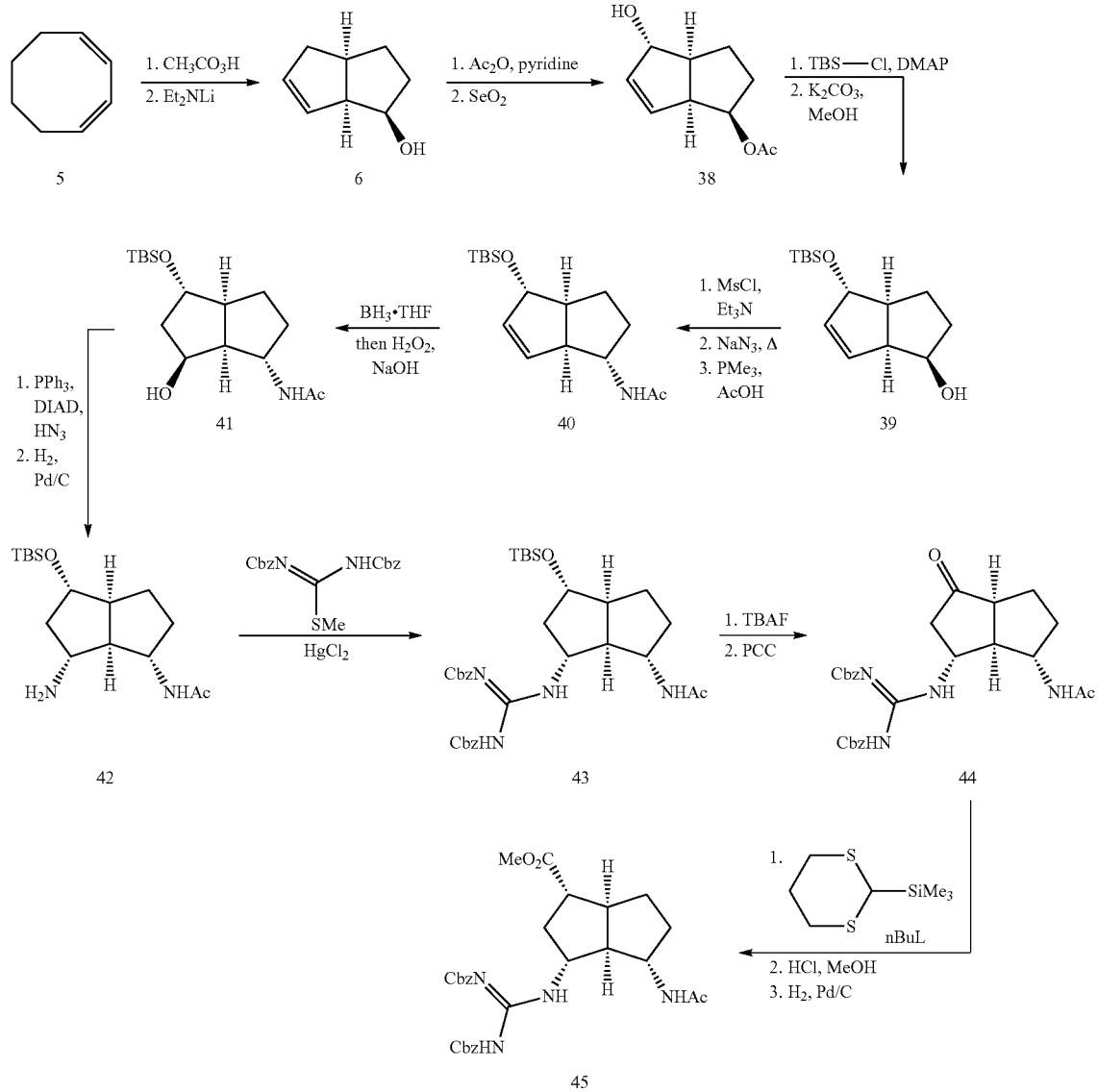

VII. Examples

The following examples are provided to illustrate certain features of working embodiments of the present invention. A person of ordinary skill in the art will appreciate that the invention is not limited to such features. All examples refer to the schemes. All compounds are numbered as found in the schemes.

Example 1

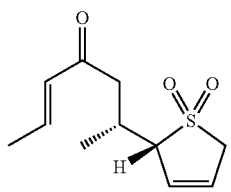

13a

As shown in Scheme 3: Hexamethyldisilazane (8.80 mL, 42.2 mmol) was dissolved in tetrahydrofuran (60 mL). The solution was cooled to −78° C., and n-butyllithium (17.8 mL, 2.20 M, 39.2 mmol) was slowly added. The solution was stirred at −78° C. for 15 min, then warmed to room temperature for 45 min. Butadiene sulfone (10) (4.20 g, 35.6 mmol) and ketone 9a (R=CH$_3$; 4.80 g, 43.6 mmol) were dissolved in tetrahydrofuran (300 mL), and the solution was cooled to −78° C. The prepared solution of LiHMDS was added via cannula. The reaction mixture was stirred for 30 min at −78° C., then removed from the cooling bath and stirred 1 hour at room temperature. The reaction was quenched by the addition of 10% aqueous HCl (50 mL), and the mixture was partially concentrated in vacuo at 30° C. The resulting yellow solution was partitioned between 10% aqueous HCl and chloroform. The organic fraction was washed with brine and dried with Na$_2$SO$_4$ then concentrated in vacuo at 30° C. to provide 7.80 g of sulfone 13a as a yellow oil. The crude product was carried to the next step with no further purification. IR (film) 1694, 1303, 1133, 971 cm$^{-1}$; $^1$H NMR (500 MHz) δ 6.89 (dq, J=16, 7 Hz, 1H), 6.12 (dq, J=16, 2 Hz, 1H) 6.11-6.00 (m, 2H), 3.78-3.63 (m, 3H), 2.92 (dd, J=16, 5 Hz, 1H), 2.74-2.65 (m, 1H), 2.55 (dd, J=16, 8 Hz, 1H), 1.89 (dd, J=7, 2 Hz, 3H), 1.14 (d, J=7 Hz, 3H); $^{13}$C NMR (125 MHz) δ 198.6 (C), 144.0 (CH), 132.1 (CH), 129.1 (CH), 124.2 (CH), 69.1 (CH), 56.6 (CH$_2$), 43.1 (CH$_2$), 29.9 (CH), 18.5 (CH$_3$), 16.8 (CH$_3$); MS (ES+) m/z 253 (4), 251 (100); HRMS calcd for C$_{11}$H$_{16}$O$_3$S (M+Na): 251.0718. Found: 251.0715.

Example 2

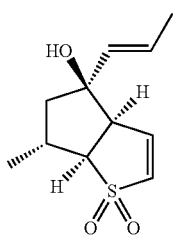

14a

As shown in Scheme 3: Hexamethyldisilazane (8.54 mL, 41.0 mmol) was dissolved in tetrahydrofuran (60 mL). The solution was cooled to −78° C., and n-butyllithium (15.1 mL, 2.50 M, 37.6 mmol) was slowly added. The solution was stirred at −78° C. for 15 minutes then warmed to room temperature for 45 minutes. Compound 13a (crude, 7.80 g, 34.2 mmol) was dissolved in tetrahydrofuran (400 mL), and the solution was cooled to −78° C. The prepared solution of LiHMDS was added via cannula. The reaction mixture was stirred for 30 minutes at −78° C. then removed from the cooling bath and stirred 5 hours at room temperature. The reaction was quenched by the addition of 10% aqueous HCl (100 mL), and the mixture was partially concentrated in vacuo. The resulting red solution was partitioned between 10% aqueous HCl and chloroform. The organic fraction was washed with brine, dried with Na$_2$SO$_4$ and concentrated in vacuo at 30° C. to provide 8.20 g of crude vinylsulfone 14a as a yellow oil. The crude product was typically carried to the next step with no further purification. Alternatively, an analytically pure sample could be obtained through flash-column chromatography (dichloromethane:ethyl acetate 10:1) followed by recrystallization from a minimum amount of ethyl acetate and diethyl ether. Mp 107-110° C.; IR (film) 3485 (br), 1282, 1132 cm$^{-1}$; $^1$H NMR (500 MHz) δ 6.52 (dd, J=7, 2 Hz, 1H), 6.49 (dd, J=7, 3 Hz, 1H), 5.79 (dq, J=15, 6 Hz, 1H), 5.58 (dq, J=15, 2 Hz, 1H), 3.53 (ddd, J=10, 3, 2 Hz, 1H), 3.19 (dd, J=10, 8 Hz, 1H), 2.97-2.85 (m, 1H), 2.02 (dd, J=13, 6 Hz, 1H), 1.71 (dd, J=6, 2 Hz, 3H), 1.70 (t, J=13 Hz, 1H), 1.24 (d, J=6 Hz, 3H); $^{13}$C NMR (125 MHz) δ 137.1 (CH), 133.7 (CH), 132.7 (CH), 125.9 (CH), 80.6 (C), 67.8 (CH), 57.8 (CH), 51.6 (CH$_2$), 33.6 (CH), 19.6 (CH$_3$), 17.8 (CH$_3$); MS (ES+) m/z 253 (4), 251 (100); HRMS calcd for C$_{11}$H$_{16}$O$_3$S (M+Na): 251.0718. Found: 251.0715.

Example 3

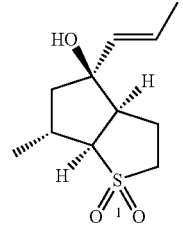

15a

As shown in Scheme 3: Compound 14a (crude, 4.50 g, 19.7 mmol) was dissolved in tetrahydrofuran (300 mL). The solution was cooled to 0° C. and LiAlH$_4$ (1.87 g, 49.3 mmol) was added in three portions over 5 minutes. The solution was warmed to room temperature and stirred for 2.5 hours. Wet sodium sulfate was added in small portions over 5 minutes until gas evolution desisted. The reaction mixture was filtered and washed with ethyl acetate and methanol. The filtrate was concentrated in vacuo to provide 4.20 g of crude sulfone 15a as yellow residue. Flash-column chromatography of a 1.10 g sample of crude material (ethyl acetate-dichloromethane: methanol 20:20:1) afforded 600 mg (50% over 3 steps) of 15a as a thick yellow oil. IR (film) 3484 (br), 1290, 1102, 972 cm$^{-1}$; $^1$H NMR (500 MHz) δ 5.72 (dq, J=15, 6 Hz, 1H), 5.44 (dq, J=15, 2 Hz, 1H), 3.28 (ddd, J=13, 13, 7 Hz, 1H), 2.93 (dd, J=10, 10 Hz, 1H), 2.87 (ddt, J=13, 7, 2 Hz, 1H), 2.82-2.76 (m, 2H), 2.11 (dd, J=13, 7 Hz, 1H), 1.97 (dddd, J=13, 13, 8, 7 Hz, 1H), 1.83 (dd, J=13, 6 Hz, 1H), 1.68 (dd, J=6, 2 Hz, 3H), 1.45

(t, J=13 Hz, 1H), 1.18 (d, J=7 Hz, 3H); ¹³C NMR (125 MHz) δ 134.4 (CH), 125.1 (CH), 82.3 (C), 69.4 (CH), 50.8 (CH₂), 50.5 (CH), 49.9 (CH₂), 35.9 (CH), 19.5 (CH₃), 19.4 (CH₂), 17.8 (CH₃); MS (ES+) m/z 253 (4), 251 (100); HRMS (ES+) calcd for $C_{11}H_{18}O_3S$ (M+Na): 253.0874. Found: 253.0869.

Example 4

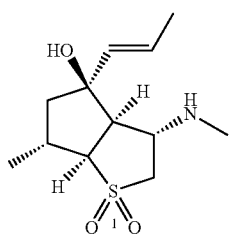

16a

Compound 14a (31 mg, 0.142 mmol) was dissolved in anhydrous ethanol (5 mL). Methylamine (200 μL, 33% in ethanol) was added. The solution was heated at 65° C. for 16 hours. The reaction mixture was concentrated in vacuo affording 36 mg (100%) of 16a as a colorless oil. IR (film) 3485, 3316, 1290, 1115, 972 cm⁻¹; ¹H NMR (500 MHz) δ 5.76 (dq, J=15, 6 Hz, 1H), 5.55 (dq, J=15, 2 Hz, 1H), 3.45 (dd, J=13, 6 Hz, 1H), 3.42 (dt, J=6, 2 Hz, 1H) 3.16-3.06 (m, 2H), 2.91-2.85 (m, 2H), 2.37 (s, 3H), 1.85 (dd, J=13, 6 Hz), 1.71 (dd, J=7, 2 Hz, 3H), 1.53 (t, J=13 Hz, 1H), 1.20 (d, J=7 Hz, 3H); ¹³C NMR (125 MHz) δ 134.3 (CH), 125.4 (CH), 81.4 (C), 69.1 (CH), 57.7 (CH), 54.9 (CH₂), 54.2 (CH), 50.0 (CH₂), 35.6 (CH), 34.0 (CH₃), 19.5 (CH₃), 17.8 (CH₃); MS (ES+) m/z 262 (4), 260 (100); HRMS calcd for $C_{12}H_{21}NO_3S$ (M+H): 260.1320. Found: 260.1315.

Example 5

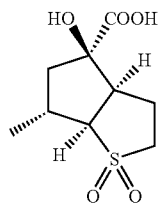

20

As shown in Scheme 5: Compound 15a (390 mg, 1.70 mmol) was dissolved in dichloromethane (70 mL). The solution was cooled to −78° C., then ozone was bubbled through until a light blue color persisted. The solution was purged with argon for 10 minutes, then dimethylsulfide (1.7 mL) was added at −78° C. The reaction mixture was warmed to room temperature and stirred for 16 hours. The reaction mixture was concentrated in vacuo, and the crude product was carried on to the next step with no further purification. The crude aldehyde was dissolved in t-butanol (15 mL) and water (7.5 mL). Potassium phosphate (1.06 g, 7.8 mmol) was added, followed by 2-methyl-2-butene (7.8 mL, 2.0 M in THF, 16 mmol). The reaction mixture was stirred for 5 minutes, then sodium chlorite (208 mg, 2.3 mmol) in water (1.5 mL) was added drop-wise. The reaction mixture was stirred for a further 80 minutes at room temperature then partitioned between ethyl acetate and 10% aqueous HCl. The aqueous layer was washed with ethyl acetate, and the combined organic fractions were dried with sodium sulfate and concentrated in vacuo. Flash column chromatography (dichloromethane: methanol:acetic acid 100:5:1) afforded 150 mg (25% over 2 steps) of 19 as a thick colorless oil. IR (film) 3473 (br), 1727, 1288, 1115 cm⁻¹; ¹H NMR (500 MHz) δ 3.52-3.45 (m, 1H), 3.26 (ddd, J=13, 10, 10 Hz, 1H), 3.07 (t, J=10 Hz, 1H), 2.93 (dt, J=13, 4 Hz, 1H), 2.88-2.75 (m, 1H), 2.13-2.09 (m, 2H), 2.06 (dd, J=13, 6 Hz, 1H), 1.87 (t, J=13 Hz, 1H), 1.25 (d, J=7 Hz, 3H); ¹³C NMR (125 MHz) δ 178.7 (C), 82.3 (C), 68.6 (CH), 50.2 (CH₂), 49.7 (CH), 47.7 (CH₂), 37.2 (CH), 20.5 (CH₂), 18.9 (CH₃); MS (ES) m/z 235 (4), 233 (100); HRMS calcd for $C_9H_{14}O_5S$ (M−H): 233.0477. Found: 233.0480.

Example 6

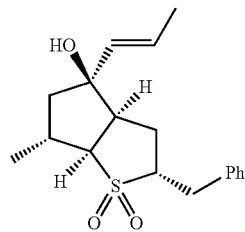 [SMILES: C/C=C/[C@@]1(O)C[C@@H](C)[C@H]2[C@@H]1C[C@H](Cc1ccccc1)S2(=O)=O]

Figure 2:
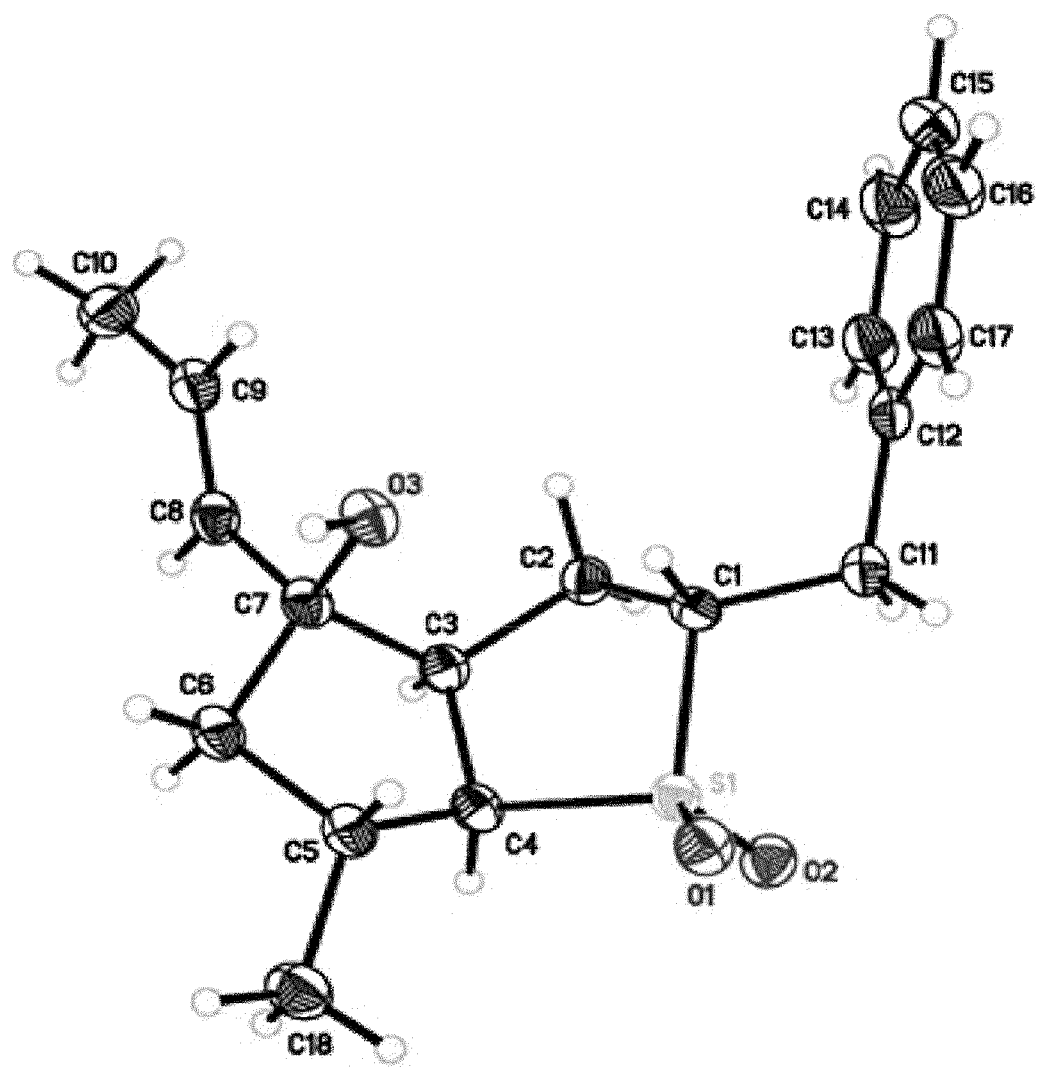
FIG. 2 is an image of the X-ray structure of the benzyl-substituted intermediate from Example 6.
Figure 3:
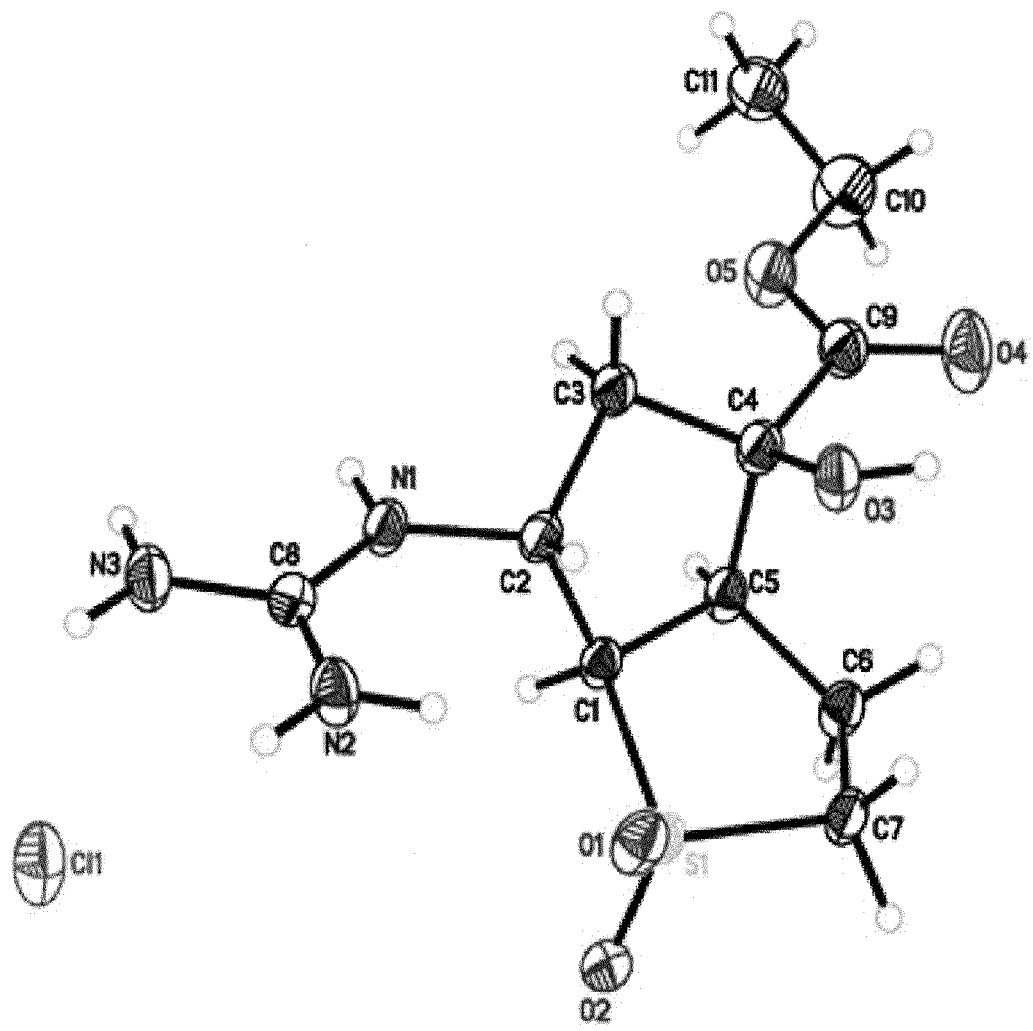
FIG. 3 is an image of the X-ray structure of the ethyl ester of compound 27 (crystallized as the hydrochloride salt) from Example 16.

As shown in Scheme 5: Compound 15a (265 mg, 1.2 mmol) was dissolved in tetrahydrofuran (15 mL). The solution was cooled to −78° C. NaHMDS (2.65 mL, 1M in THF, 2.65 mmol) was added in one portion. The solution was warmed to room temperature over 30 minutes. The reaction mixture was cooled to −78° C. whereupon benzyl bromide (175 pt, 1.5 mmol) was added. The solution was stirred for 2 hours at −78° C. then warmed to room temperature and stirred for 16 hours. The reaction mixture was partitioned between ethyl acetate and saturated aqueous NH₄Cl. The aqueous layer was washed with ethyl acetate, and the combined organic fractions were washed with brine then dried with sodium sulfate and concentrated in vacuo. Flash-column chromatography (hexanes-ethyl acetate 2:1) afforded 316 mg (83%) of the C2-benzyl sulfone as a white solid. An image of the X-ray structure of this compound is illustrated in FIG. 2. Mp 129-132° C.; IR (film) 3502 (br), 1288, 1114, 967 cm⁻¹; ¹H NMR (500 MHz) δ 7.27-7.15 (m, 5H), 5.58 (dq, J=15, 7 Hz, 1H), 5.40 (dq, J=15, 2 Hz, 1H), 3.66 (dddd, J=13, 9, 7, 6 Hz, 1H), 3.18 (dd, J=14, 5 Hz, 1H), 2.99 (dd, J=11, 9 Hz, 1H), 2.83-2.73 (m, 1H), 2.71 (dd, J=14, 9 Hz, 1H), 2.65 (dd, J=10, 9 Hz, 1H), 2.02 (dd, J=13, 7 Hz, 1H), 1.80 (d, J=1.5 Hz, 1H), 1.78 (dd, J=13, 6 Hz, 1H), 1.66 (dddd, J=13, 13, 7 Hz, 1H), 1.62 (dd, J=7, 2 Hz, 3H), 1.42 (t, J=13 Hz, 1H), 1.17 (d, J=6 Hz, 3H); ¹³C NMR (125 MHz) δ 137.6 (C), 134.3 (CH), 129.0 (CH), 128.7 (CH), 126.7 (CH), 124.8 (CH), 81.8 (C), 69.8 (CH), 60.4 (CH), 49.3 (CH₂), 47.7 (CH), 36.1 (CH), 32.4

($CH_2$), 26.0 ($CH_2$), 19.2 ($CH_3$), 17.7 ($CH_3$); MS (ES+) m/z 345 (4), 343 (100); HRMS calcd for $C_{18}H_{24}O_3S$ (M+Na): 343.1344. Found: 343.1342.

Example 7

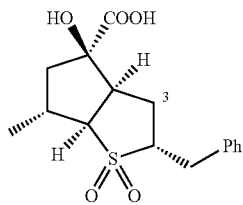
21

As shown in Scheme 5: The alkene from Example 6 (220 mg, 0.69 mmol) was dissolved in dichloromethane (60 mL). The solution was cooled to −78° C., then ozone was bubbled through until a light blue color persisted. The solution was purged with argon for 10 minutes, then dimethylsulfide (0.7 mL) was added at −78° C. The reaction mixture was warmed to room temperature and stirred for 16 hours. The reaction mixture was concentrated in vacuo, and the crude product was carried on to the next step with no further purification. The crude aldehyde was dissolved in t-butanol (15 mL) and water (7.5 mL). Potassium phosphate (554 mg, 4.1 mmol) was added followed by 2-methyl-2-butene (4.1 mL, 2.0 M in THF, 8.2 mmol). The reaction mixture was stirred for 5 minutes then sodium chlorite (111 mg, 1.2 mmol) in water (1.5 mL) was added drop-wise. The reaction mixture was stirred for 80 minutes at room temperature then partitioned between ethyl acetate and 10% HCl. The aqueous layer was washed with ethyl acetate, and the combined organic fractions were dried with sodium sulfate and concentrated in vacuo. Flash column chromatography (dichloromethane:methanol:acetic acid 100:5:1) afforded 180 mg (80% over 2-steps) of 20 as a thick oil. IR (film) 3467 (br), 1731, 1288, 1114 $cm^{-1}$; $^1$H NMR (500 MHz): δ 7.31-7.16 (m, 5H), 3.59 (m, 1H), 3.35 (dd, J=11, 8 Hz, 1H), 3.24 (dd, 1=14, 5 Hz, 1H), 3.14 (dd, J=11, 9 Hz, 1H), 2.87-2.76 (m, 1H), 2.72 (dd, J=14, 10 Hz, 1H), 2.00 (dd, J=13, 6 Hz, 1H), 1.91 (dd, J=14, 6, 1H), 1.84-1.72 (m, 2H), 1.26 (d, J=7 Hz, 3H); $^{13}$C NMR (125 MHz) δ 178.8 (C), 137.2 (C), 129.0 (CH), 128.9 (CH), 127.1 (CH), 82.1 (C), 69.9 (CH), 60.0 (CH), 47.4 ($CH_2$), 47.0 (CH), 37.7 (CH), 32.0 ($CH_2$), 26.8 ($CH_2$), 18.8 ($CH_3$); MS (ES) m/z 325 (4), 323 (100); HRMS calcd for $C_{16}H_{20}O_5S$ (M−H): 323.0953. Found: 323.0957.

Example 8

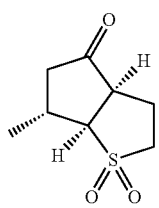
22

As shown in Scheme 5: Compound 15a (50 mg, 0.22 mmol) was dissolved in acetonitrile (5 mL) and water (3 mL). Ruthenium trichloride (2 mg, 0.01 mmol) was added followed by a mixture of Oxone (270 mg, 0.44 mmol) and sodium bicarbonate (85 mg, 1.0 mmol) in three portions over 10 min. After 1 hour the reaction mixture was partitioned between 10% aqueous sodium thiosulfate and dichloromethane. The aqueous layer was washed with dichloromethane then the combined organic extracts were dried ($Na_2SO_4$) and concentrated in vacuo. Crystallization from a minimum amount of ether and hexanes provided 42 mg (82%) of 22 as a white solid. IR (film) 1746, 1298, 1115 $cm^{-1}$; $^1$H NMR (500 MHz): δ 3.34 (dd, J=10, 5 Hz, 1H), 3.17 (td, J=10, 4 Hz, 1H), 3.10-3.02 (m, 1H), 2.83-2.70 (m, 2H), 2.62 (dd, J=18, 8 Hz, 1H), 2.38-2.28 (m, 2H), 2.16 (dd, J=18, 7 Hz, 1H), 1.29 (d, J=7 Hz, 3H) $^{13}$C NMR (125 MHz) δ 215.1 (C), 66.7 (CH), 49.7 ($CH_2$), 48.1 (CH), 45.8 ($CH_2$), 30.8 (CH), 22.1 ($CH_2$), 21.4 (CH); MS (ES+) m/z 213 (4), 211 (100), 152 (13); HRMS calcd for $C_8H_{14}O_3S$ (M+Na): 211.0405. Found: 211.0407.

Example 9

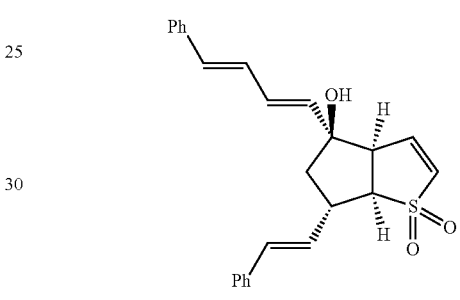
14b

As shown in Scheme 6: Hexamethyldisilazane (432 μL, 2.08 mmol) was dissolved in tetrahydrofuran (5 mL). The solution was cooled to −78° C., and n-butyllithium (1.25 mL, 1.54 M, 1.92 mmol) was slowly added. The solution was stirred at −78° C. for 15 minutes, then warmed to room temperature for 45 minutes. Butadiene sulfone (10) (188 mg, 1.60 mmol) and ketone 9b (458 mg, 1.60 mmol) were dissolved in tetrahydrofuran (20 mL), and the solution was cooled to −78° C. The prepared solution of LiHMDS was added via cannula. The reaction mixture was stirred for 40 min at −78° C., then removed from the cooling bath and stirred 1 hour at room temperature. The reaction was quenched by the addition of 10% aqueous HCl (10 mL), and the mixture was partially concentrated in vacuo at 30° C. The resulting yellow solution was partitioned between 10% aqueous HCl and dichloromethane. The organic fraction was washed with brine and dried with $Na_2SO_4$ then concentrated in vacuo at 30° C. to provide 701 mg of crude keto-sulfone as a red oil. The crude product was carried to the next step with no further purification.

Hexamethyldisilazane (362 μL, 1.74 mmol) was dissolved in tetrahydrofuran (10 mL). The solution was cooled to −78° C., and n-butyllithium (1.06 mL, 1.54 M, 1.59 mmol) was slowly added. The solution was stirred at −78° C. for 15 minutes then warmed to room temperature for 45 minutes. The crude keto-sulfone (573 mg, 1.31 mmol) was dissolved in tetrahydrofuran (20 mL), and the solution was cooled to −78° C. The prepared solution of LiHMDS was added via cannula. The reaction mixture was stirred for 30 minutes at −78° C. then removed from the cooling bath and stirred 5 hours at room temperature. The reaction was quenched by the addition of 10% aqueous HCl (10 mL), and the mixture was partially concentrated in vacuo. The resulting yellow solution was partitioned between 10% aqueous HCl and dichloromethane. The organic fraction was washed with brine, dried with Na₂SO₄ and concentrated in vacuo at 30° C. Flash-column chromatography (dichloromethane-ethyl acetate 10:1) afforded 201 mg (38% over 2 steps) of vinyl sulfone 14b as a yellow oil; IR (film) 3479 (br), 1284, 1132 cm⁻¹; ¹H NMR (500 MHz) δ 7.50-7.16 (m, 10H), 6.78 (dd, J=16, 10 Hz), 6.64-6.53 (m, 5H), 6.23 (dd, J=16, 7 Hz), 5.91 (d, J=16 Hz, 1H), 3.78 (ddt, J=13, 8, 7 Hz, 1H), 3.65 (ddd, 10, 3, 2 Hz, 1H), 3.57 (dd, J=10, 8 Hz, 1H), 2.23 (dd, J=13, 7 Hz, 1H), 2.11 (t, J=13 Hz, 1H); ¹³C NMR (125 MHz) δ 137.0 (C), 136.7 (C), 136.4 (CH), 135.0 (CH), 134.3 (CH), 133.4 (CH), 132.2 (CH), 130.7 (CH), 129.0 (CH), 128.9 (CH), 128.8 (CH), 128.2 (CH), 127.9 (CH), 127.4 (CH), 126.7 (CH), 126.6 (CH), 80.6 (C), 66.0 (CH), 57.8 (CH), 50.0 (CH₂), 41.8 (CH); MS (ES+) m/z 429 (4), 427 (100); HRMS calcd for C₂₅H₂₄O₃S (M+Na): 427.1344. Found: 427.1350.

Example 10

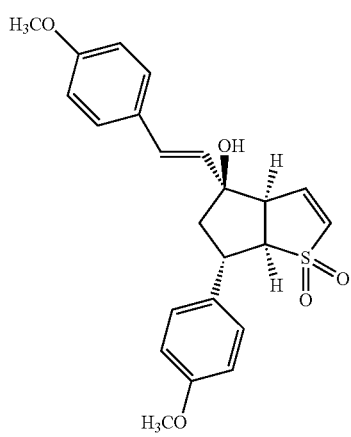

14c

As shown in Scheme 6: Butadiene sulfone (10) (4.15 g, 35.2 mmol) and ketone 9c (10.3 g, 35.2 mmol) were dissolved in tetrahydrofuran (200 mL), and the solution was cooled to −78° C. LiHMDS (42.3 mL, 1 M in THF, 42.3 mmol) was added in one portion. The reaction mixture was stirred for 1 hour at −78° C., then removed from the cooling bath and stirred 1 hour at room temperature. The reaction was quenched by the addition of 10% aqueous HCl (50 mL), and the mixture was partially concentrated in vacuo at 30° C. The resulting orange solution was partitioned between 10% aqueous HCl and dichloromethane. The organic fraction was washed with brine and dried with Na₂SO₄ then concentrated in vacuo at 30° C. to provide 14.5 g of crude keto sulfone intermediate as a light orange foam. The crude product was carried to the next step with no further purification. IR (film) 1683, 1305, 1173 cm⁻¹; ¹H NMR (CDCl₃ 300 MHz) δ 7.51 (d, J=16 Hz, 1H), 7.47 (d, J=8.7 Hz, 2H), 7.27 (d, J=8.7 Hz, 2H), 6.90 (d, J=8.7 Hz, 2H), 6.83 (d, J=8.7 Hz, 2H), 6.56 (d, 16 Hz, 1H), 6.20-6.06 (m, 2H), 4.11-4.05 (m, 1H), 4.00-3.91 (m, 1H), 3.83 (s, 3H), 3.76 (s, 3H), 3.72-3.64 (m, 1H), 3.52 (ddd, J=16, 4.5, 2.3 Hz, 1H), 3.33 (dd, J=16, 5.2 Hz, 1H), 3.14 (dd, J=16, 9.2 Hz, 1H); ¹³C NMR (CDCl₃ 75 MHz) δ 197.9 (C), 161.8 (C), 158.8 (C), 143.2 (CH), 131.3 (C), 130.2 (CH), 129.5 (CH), 128.6 (CH), 127.0 (CH), 124.6 (CH), 123.6 (CH), 114.5 (CH), 114.0 (CH), 69.1 (CH), 56.0 (CH₂), 55.4 (CH₃), 55.2 (CH₃), 42.4 (CH₂), 40.0 (CH); MS (ES+) m/z 435 (100); HRMS calcd for C₂₃H₂₄O₅S (M+H): 413.1423. Found: 413.1423.

The crude intermediate (14.5 g, 35.2 mmol) was dissolved in tetrahydrofuran (400 mL), and the solution was cooled to −78° C. LiHMDS (42.3 mL, 1 M in THF, 42.3 mmol) was added in one portion. The reaction mixture was stirred for 30 minutes at −78° C. then removed from the cooling bath and stirred 2.5 hours at room temperature. The reaction was quenched by the addition of saturated aqueous NH₄Cl and the mixture was partially concentrated in vacuo. The resulting red solution was partitioned between saturated aqueous NH₄Cl and dichloromethane. The organic fraction was washed with brine, dried with Na₂SO₄ and concentrated in vacuo at 30° C. to provide 14.5 g of crude vinyl sulfone 14c as a brick red solid. The crude product was carried to the next step with no further purification. IR (film) 3479 (br), 1250, 1132 cm⁻¹; ¹H NMR (300 CDCl₃ MHz) δ 7.35 (d, J=8.6 Hz, 2H), 7.28 (d, J=8.6 Hz, 2H), 6.89 (d, J=8.8 Hz, 2H), 6.88 (d, J=8.8 Hz, 2H), 6.74 (d, J=16 Hz, 1H), 6.66 (dd, J=6.8, 1.5 Hz, 1H), 6.59 (dd, J=6.8, 3.1 Hz, 1H), 6.23 (d, J=16 Hz, 1H), 4.25-4.13 (m, 1H), 3.82 (s, 3H), 3.80 (s, 3H), 3.77 (ddd, J=9.7, 3.1, 2.5 Hz, 1H), 3.72 (dd, J=9.7, 7.4 Hz, 1H), 2.42 (d, J=9.8 Hz, 2H); ¹³C NMR (CDCl₃ 75 MHz) δ 159.8 (C), 158.8 (C), 136.3 (CH), 133.3 (CH), 132.7 (C), 129.6 (CH), 128.8 (CH), 128.6 (C), 128.4 (CH), 128.0 (CH), 114.4 (CH), 114.3 (CH), 80.7 (C), 67.9 (CH), 58.0 (CH), 55.5 (CH₃), 55.5 (CH₃), 50.6 (CH₂), 42.6 (CH); MS (ES+) m/z 435 (100); HRMS calcd for C₂₃H₂₄O₅S (M+Na): 435.1242. Found: 435.1239.

Example 11

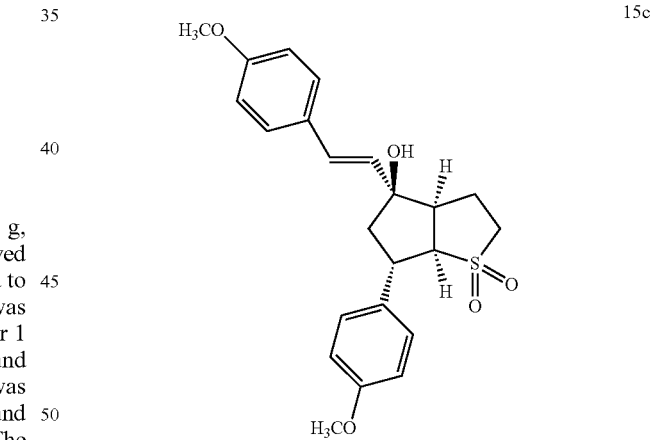

15c

As shown in Scheme 6: Compound 14c (crude, 5.01 g, 12.5 mmol) was dissolved in tetrahydrofuran (200 mL). The solution was cooled to 0° C. and Red-Al (5.7 mL, 65% in toluene, 18.5 mmol) was added in one portion. The solution was stirred at 0° C. for 45 minutes. An aqueous 10% solution of Rochelle's salt was added in small portions over 5 minutes until gas evolution desisted. The reaction mixture was partitioned between EtOAc and water. The organic fraction was dried with Na₂SO₄ and concentrated in vacuo. Flash-column chromatography (dichloromethane-ethyl acetate 25:1) afforded 1.33 g (26% over 3 steps from 10) of sulfone 15c. IR (film) 3477 (br), 1250, 1108 cm⁻¹; ¹H NMR (CDCl₃ 300 MHz) δ 7.22 (d, J=8.8 Hz, 2H), 7.14 (d, J=8.8 Hz, 2H), 6.76 (d, J=8.8 Hz, 2H), 6.74 (d, J=8.8 Hz, 2H), 6.56 (d, J=16 Hz, 1H), 6.01 (d, J=16 Hz, 1H), 4.00-3.89 (m, 1H), 3.70 (s, 3H), 3.66 (s, 3H), 3.44-3.30 (m, 2H), 2.98-2.80 (m, 2H), 2.20-1.87 (m, 4H); $^{13}$C NMR (CDCl$_3$ 75 MHz) δ 159.5 (C), 158.6 (C), 133.4 (C), 129.6 (CH), 129.0 (CH), 128.9 (C), 128.5 (CH), 127.8 (CH), 114.2 (CH), 114.2 (CH), 82.4 (C), 70.0 (CH), 55.4 (CH$_3$), 55.4 (CH$_3$), 51.3 (CH$_2$), 51.0 (CH), 49.0 (CH$_2$), 44.8 (CH), 19.3 (CH$_2$); MS (ES+) m/z 437 (100); HRMS calcd for C$_{23}$H$_{26}$O$_5$S (M+Na): 437.1399. Found: 437.1393.

Example 12

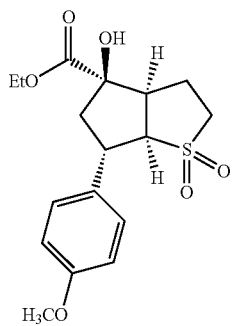

23

As shown in Scheme 6: Compound 15c (1.33 g, 3.21 mmol) was dissolved in dichloromethane (80 mL). The solution was cooled to −78° C., then ozone was bubbled through until a light blue color persisted. The solution was purged with argon for 10 min, then dimethylsulfide (3.21 mL) was added at −78° C. The reaction mixture was warmed to room temperature and stirred for 16 hours. The reaction mixture was concentrated in vacuo, and the crude product was carried on to the next step with no further purification. The crude aldehyde was dissolved in t-butanol (16 mL), tetrahydrofuran (8 mL) and water (8 mL). Potassium phosphate (2.2 g, 16 mmol) was added, followed by 2-methyl-2-butene (1.7 mL, 16 mmol). The reaction mixture was stirred for 5 minutes, then sodium chlorite (725 mg, 8.03 mmol) in water (2 mL) was added drop-wise. The reaction mixture was stirred for a further 60 minutes at room temperature then partitioned between ethyl acetate and 10% aqueous HCl. The aqueous layer was washed with ethyl acetate, and the combined organic fractions were dried with sodium sulfate and concentrated in vacuo. Flash column chromatography (dichloromethane methanol:acetic acid 100:1:1 to dichloromethane methanol:acetic acid 100:5:2) afforded 752 mg (72% over 2 steps) of carboxylic acid intermediate as a white solid. IR (film) 3460 (br), 1732, 1251, 1113 cm$^{-1}$; $^1$H NMR (CD$_3$C(O)CD$_3$ 300 MHz) δ 7.35 (d, J=8.6 Hz, 2H), 6.90 (d, J=8.6 Hz, 2H), 4.02-3.89 (m, 1H), 3.78 (s, 3H), 3.71 (dd, J=10, 9.2 Hz, 1H), 3.55 (dd, J=10, 9.2 Hz, 1H), 3.35 (td, J=13, 7.6 Hz, 1H), 3.00-2.91 (m, 1H), 2.45 (t, J=13 Hz, 1H), 2.34-2.22 (m, 2H), 2.19-2.08 (m, 1H); $^{13}$C NMR (CD$_3$C(O)CD$_3$ 75 MHz) δ 175.4 (C), 159.5 (C), 134.0 (C), 129.6 (CH), 114.8 (CH), 82.9 (C), 69.9 (CH), 55.4 (CH$_3$), 51.6 (CH$_2$), 50.7 (CH), 47.4 (CH$_2$), 46.6 (CH), 20.9 (CH$_2$); MS (ES+) m/z 349 (100); HRMS calcd for C$_{15}$H$_{18}$O$_6$S (M+Na): 349.0722. Found: 349.0717.

The acid (752 mg, 0.576 mmol) was dissolved in benzene (60 mL) and ethanol (5 mL). p-Toylsulfonic acid (4 mg, 0.023 mmol) was added and the solution was heated at 80° C. using a dean-stark apparatus for 16 hours. The reaction mixture was cooled to room temperature, then partitioned between water and EtOAc. The organic fraction was dried with Na$_2$SO$_4$ and concentrated in vacuo to provide 773 mg of ethyl ester 23 as a white solid. The crude product was carried to the next step with no further purification. IR (film) 3465 (br), 1732, 1252, 1113 cm$^{-1}$; $^1$H NMR (CDCl$_3$ 300 MHz) δ 7.28 (d, J=8.6 Hz, 2H), 6.88 (d, J=8.6 Hz, 2H), 4.32 (qd, J=7.2, 1.4 Hz, 2H), 3.99 (ddd, J=13, 10, 7.3 Hz, 1H), 3.80 (s, 3H), 3.67-3.51 (m, 2H), 3.50-3.34 (m, 1H), 3.02-2.92 (m, 1H), 2.36 (t, J=13 Hz, 1H), 2.24 (dd, J=13, 7.2 Hz, 1H), 2.19-2.06 (m, 2H), 1.34 (t, J=7.2 Hz, 3H); $^{13}$C NMR (CDCl$_3$ 75 MHz) δ 174.3 (C), 158.8 (C), 132.3 (C), 128.6 (CH), 114.3 (CH), 82.4 (C), 69.1 (CH), 63.1 (CH$_2$), 55.4 (CH$_3$), 50.6 (CH$_2$), 49.6 (CH), 46.8 (CH$_2$), 46.0 (CH), 20.5 (CH$_2$), 14.3 (CH$_3$); MS (ES+) m/z 377 (100); HRMS calcd for C$_{17}$H$_{22}$O$_6$S (M+Na): 377.1035. Found: 377.1032.

Example 13

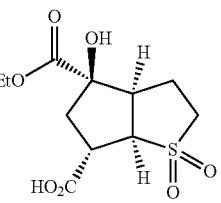

24

As shown in Scheme 6: Ester 23 (crude, 640 mg, 1.81 mmol) was dissolved in CCl$_4$ (5 mL), acetonitrile (5 mL) and water (15 mL). NaHCO$_3$ (152 mg, 1.81 mmol) was added, followed by NaIO$_4$ (5.81 g, 27.2 mmol). RuCl$_3$ (18 mg, 0.091 mmol) was added and the reaction mixture was stirred 16 h. The reaction mixture was partitioned between 10% aqueous HCl and EtOAc. The organic fraction was dried with Na$_2$SO$_4$ then concentrated in vacuo at 30° C. The crude solid was dissolved in chloroform, filtered through cotton, then concentrated in vacuo to provide 373 mg of crude acid 24 as a white solid. The crude product was carried to the next step with no further purification. IR (film) 3470 (br), 1734, 1265, 1114 cm$^{-1}$; $^1$H NMR (CDCl$_3$ 300 MHz) δ 4.29 (qd, J=7.3, 2.0 Hz, 2H), 3.99-3.90 (m, 1H) 3.73 (td, J=10, 8.4 Hz, 1H), 3.50-3.41 (m, 1H), 3.41-3.38 (m, 1H), 3.07-2.96 (m, 1H), 2.42-2.32 (m, 2H), 2.25-2.06 (m, 2H), 1.32 (t, J=7.3 Hz, 3H); $^{13}$C NMR (CDCl$_3$ 75 MHz) δ 177.1 (C), 173.6 (C), 82.4 (C), 63.9 (CH), 63.3 (CH$_2$), 50.8 (CH$_2$), 49.1 (CH), 45.6 (CH), 42.6 (CH$_2$), 20.5 (CH$_2$), 14.3 (CH$_3$); MS (ES+) m/z 315 (100); HRMS calcd for C$_{11}$H$_{16}$O$_7$S (M+Na): 315.0515. Found: 315.0516.

Example 14

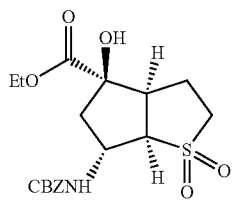

25

As shown in Scheme 6: Compound 24 (crude, 373 mg, 1.28 mmol) was dissolved in benzene (30 mL). Triethylamine (271 µL, 1.92 mmol) was added, followed by DPPA (277 µL, 1.28 mmol). BnOH (200 µL, 1.92 mmol) was added and the reaction mixture was stirred at 80° C. for 16 hours. The reaction mixture was quenched with saturated aqueous NH₄Cl then partitioned between saturated aqueous NH₄Cl and EtOAc. The organic fraction was dried with Na₂SO₄ and then concentrated in vacuo. Flash column chromatography (dichloromethane:EtOAc 20:1 to dichloromethane:EtOAc 2:1) afforded 171 mg (23% over 3 steps) of 25 as a light brown solid. IR (film) 3349 (br), 1722, 1265, 1113 cm⁻¹; ¹H NMR (CD₃C(O)CD₃ 300 MHz) δ 7.43-7.23 (m, 5H), 6.83 (s, 1H), 5.08 (s, 2H), 4.76-4.63 (m, 1H), 4.21 (q, J=7.3 Hz, 2H), 3.69-3.48 (m, 2H) 3.26 (td, J=10, 8.4 Hz, 1H), 2.98-2.88 (m, 1H), 2.80 (d, J=9.2 Hz, 2H), 2.45-2.13 (m, 3H), 1.26 (t, J=13 Hz, 3H); ¹³C NMR (CD₃COD 75 MHz) δ 174.4 (C), 157.8 (C), 138.1 (C), 129.5 (CH), 129.2 (CH), 129.0 (CH), 82.3 (C), 67.6 (CH), 67.5 (CH₂), 67.3 (CH), 62.9 (CH₂), 55.0 (CH), 52.0 (CH₂), 45.3 (CH₂), 21.3 (CH₂), 14.4 (CH₃); MS (ES+) m/z 420 (100); HRMS calcd for C₁₈H₂₃NO₇S (M+Na): 420.1093. Found: 420.1092.

Example 15

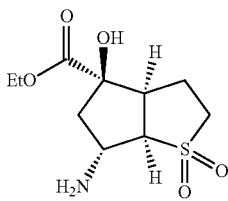

26

As shown in Scheme 6: Compound 25 (151 mg, 0.380 mmol) was dissolved in methanol (8 mL). Acetic acid (~100 μL) was added, followed by Pd/C 10% (~10 mg). The reaction mixture was stirred inside a Parr reactor pressurized to 300 PSI H₂ and was stirred for 16 hours. The reaction mixture was filtered through cotton, diluted with cyclohexane (10 mL) then concentrated in vacuo to provide 111 mg of the acetic acid salt of amine 26 as a white solid. The crude product was carried to the next step with no further purification. IR (film) 3261 (br), 1739, 1262, 1114 cm⁻¹; ¹H NMR (CD₃C(O)CD₃ 300 MHz) δ 4.63 (dt, J=11, 6.8 Hz, 1H), 4.20 (qd, J=7.4, 1.1 Hz, 2H), 3.66-3.47 (m, 2H), 3.31-3.17 (m, 1H), 2.97-2.85 (m, 1H), 2.33-2.07 (m, 4H), 1.26 (t, J=7.4 Hz, 3H); ¹³C NMR (CD₃C(O)CD₃ 75 MHz) δ 173.7 (C), 83.9 (C), 71.0 (CH), 64.1 (CH), 63.4 (CH₂), 52.7 (CH₂), 50.6 (CH), 46.9 (CH₂), 22.3 (CH₂), 15.5 (CH₃); MS (ES+) m/z 264 (100); HRMS calcd for C₁₀H₁₇NO₅S (M+H): 264.0906. Found: 264.0901.

Example 16

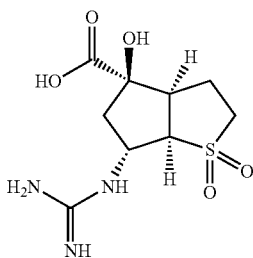

27

As shown in Scheme 6: Compound 26 (crude, 54 mg, 0.167 mmol) was dissolved in DMF (5 mL). Triethylamine (120 μL, 0.836 mmol) was added, followed by HgCl₂ (45 mg, 0.167 mmol). 1,3-bis(benzyloxycarbonyl)-2-methylisothiourea (60 mg, 0.167 mmol) was added and the reaction mixture was stirred 16 hours. The reaction mixture was diluted EtOAc, filtered through celite, then concentrated in vacuo. Flash column chromatography (dichloromethane:EtOAc 25:1 to dichloromethane:EtOAc 10:1) afforded 55 mg (53% over 2 steps) of the N—CBZ, O-Et derivative of 27 as a white solid. IR (film) 3477 (br), 3288 (br), 1771, 1732, 1622, 1271, 1114 cm⁻¹; ¹H NMR (CD₃C(O)CD₃ 300 MHz) δ 11.89 (s, 1H), 8.70 (d, J=8.0 Hz, 1H), 7.49-7.29 (m, 10H), 5.26 (s, 2H), 5.12 (s, 2H), 4.21 (q, J=7.1 Hz, 2H), 3.88 (dd, J=10, 8.9 Hz, 1H), 3.66-3.57 (m, 1H), 3.35-3.22 (m, 1H), 3.01-2.90 (m, 1H), 2.45-2.37 (m, 2H), 2.28-2.06 (m, 3H), 1.24 (t, J=7.1 Hz, 3H); ¹³C NMR (CD₃C(O)CD₃ 75 MHz) δ 173.7 (C), 164.5 (C), 156.5 (C), 154.2 (C), 138.1 (C), 136.3 (C), 129.5 (CH), 129.4 (CH), 129.4 (CH), 129.2 (CH), 129.1 (CH), 128.7 (CH), 82.3 (C), 68.9 (CH₂), 67.8 (CH₂), 67.3 (CH), 62.4 (CH₂), 54.5 (CH), 51.7 (CH₂), 49.1 (CH), 44.9 (CH₂), 21.2 (CH₂), 14.4 (CH₃); MS (ES+) m/z 596 (100); HRMS calcd for C₂₇H₃₁N₃O₉S (M+Na): 596.1678. Found: 596.1674.

The protected guanidine (54 mg, 0.094 mmol) was dissolved in methanol (5 mL). Acetic acid (~100 μL) was added, followed by Pd/C 10% (~10 mg). The reaction mixture was stirred inside a Parr reactor pressurized to 300 PSI H₂ and was stirred for 16 hours. The reaction mixture was filtered through cotton, diluted with cyclohexane (10 mL) then concentrated in vacuo to provide 29 mg (84%) of the acetic acid salt of guanidine 26, ethyl ester. Mp: decomposed at 218° C.; IR (film) 3350 (br), 1732, 1667, 1260, 1108 cm⁻¹; ¹H NMR (CD₃OD 300 MHz) δ 4.61-4.51 (m, 1H), 4.25 (qd, J=7.1, 1.2 Hz, 2H), 3.59-3.51 (m, 2H), 3.38 (td, J=13, 7.6 Hz, 1H), 3.13-3.02 (m, 1H), 2.26-2.07 (m, 4H), 1.30 (t, J=7.1 Hz, 3H); ¹³C NMR (CD₃OD 75 MHz) δ 173.7 (C), 158.3 (C), 82.0 (C), 69.3 (CH), 63.2 (CH₂), 56.0 (CH), 52.1 (CH₂), 50.1 (CH), 45.3 (CH₂), 21.7 (CH₂), 14.4 (CH₃); MS (ES+) m/z 306 (100); HRMS calcd for C₁₁H₁₉N₃O₅S (M+Na): 306.1124. Found: 306.1117.

The ethyl ester salt (22.6 mg, 0.0618 mmol) was dissolved in 750 μL of 10% NaOH in H₂O and 100 μL DMSO. The reaction mixture was stirred for 16 hours, then neutralized with 12 M HCl to provide a standard solution (57.8 mM) of sulfone 27. Hydrolysis of the ester function was confirmed through MS (ES+) m/z 276 (100).

Example 17

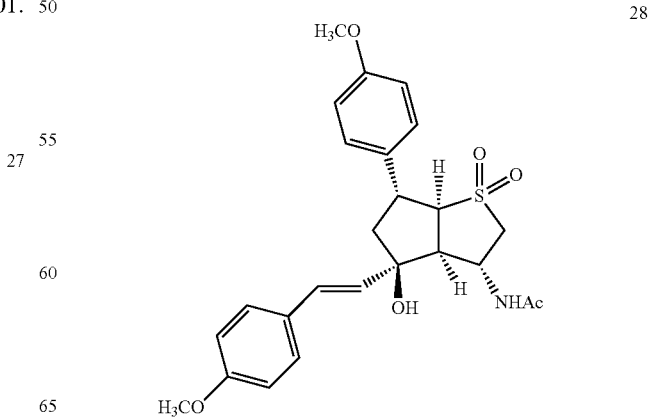

28

As shown in Scheme 7: Compound 14c (crude, 4.50 g, 10.9 mmol) was dissolved in 50 mL acetonitrile and 50 mL of aqueous ammonia (28% w/w). The reaction mixture was heated at 60° C. for 3 days in a sealed vessel. The reaction mixture was partitioned between ethyl acetate and water. The aqueous layer was washed with ethyl acetate, and the combined organic extracts were dried with sodium sulfate and concentrated in vacuo to provide 4.04 g of the conjugate addition product as yellow solid. The crude product was carried to the next step with no further purification. IR (film) 3470 (br), 3348 (br) 1513, 1250, 1112 cm$^{-1}$; $^1$H NMR (CDCl$_3$ 300 MHz) δ 7.34 (d, J=8.6 Hz, 2H), 7.25 (d, J=8.6 Hz, 2H), 6.87 (d, J=8.6 Hz, 2H), 6.87 (d, J=8.7 Hz, 2H), 6.70 (d, J=16 Hz, 1H), 6.21 (d, J=16 Hz), 4.15-4.03 (m, 1H), 3.81 (s, 3H), 3.79 (s, 3H), 3.80-3.68 (m, 3H), 3.04-2.95 (m, 2H), 2.25-2.17 (m, 2H); $^{13}$C NMR (CDCl$_3$ 75 MHz) δ 159.7 (C), 158.7 (C), 133.2 (C), 129.6 (CH), 129.2 (CH), 128.8 (C), 128.5 (C), 128.0 (CH), 114.4 (CH), 114.3 (CH), 81.4 (C), 68.8 (CH), 61.7 (CH), 59.8 (CH$_2$), 55.4 (CH$_3$), 55.4 (CH$_3$), 49.2 (CH$_2$), 46.3 (CH), 44.6 (CH); MS (ES+) m/z 452 (100); HRMS calcd for C$_{23}$H$_{27}$NO$_5$S (M+Na): 452.1502. Found: 452.1496.

The amine (crude, 4.04 g, 9.42 mmol) was dissolved in 120 mL dichloromethane. DMAP (217 mg, 1.78 mmol) was added, followed by acetic anhydride (2.65 mL, 28.0 mmol). The reaction mixture was stirred at room temperature for 16 hours. The reaction mixture was partitioned between 10% aqueous sodium bicarbonate and dichloromethane. The aqueous layer was washed with dichloromethane, and the combined organic extracts were dried with sodium sulfate and concentrated in vacuo. Flash column chromatography (dichloromethane:EtOAc 4:1 to dichloromethane:EtOAc 1:1) afforded 1.61 g (31% over 4 steps from 10) of acetamide 28 as a yellow solid. IR (film) 3360 (br), 1658, 1250, 1113 cm$^{-1}$; $^1$H NMR (CDCl$_3$ 300 MHz) δ 7.36 (d, J=8.6 Hz, 2H), 7.26 (d, J=8.6 Hz, 2H), 6.88 (d, J=8.6 Hz, 2H), 6.86 (d, J=8.6 Hz, 2H), 6.73 (d, J=16 Hz, 1H), 6.44 (d, J=8.7 Hz, 1H), 6.36 (d, J=16 Hz, 1H), 4.91 (dd, J=8.5, 7.0 Hz, 1H), 4.10-3.99 (m, 1H), 3.81 (s, 3H), 3.80 (s, 3H), 3.79-3.74 (m, 1H), 3.67-3.58 (m, 1H), 3.13-3.06 (m, 1H), 2.97-2.89 (m, 1H), 2.30-2.15 (m, 2H) 1.95 (s, 3H); $^{13}$C NMR (CDCl$_3$ 75 MHz) δ 169.9 (C), 159.4 (C), 158.5 (C), 132.7 (C), 129.0 (C), 129.0 (CH), 128.9 (CH), 128.3 (CH), 127.8 (CH), 114.1 (CH), 114.1 (CH), 80.6 (C), 69.5 (CH), 58.9 (CH), 56.1 (CH$_2$), 55.2 (CH$_3$), 55.2 (CH$_3$), 48.1 (CH$_2$), 45.5 (CH), 44.0 (CH), 23.0 (CH$_3$); MS (ES+) m/z 494 (100); HRMS calcd for C$_{25}$H$_{29}$NO$_6$S (M+Na): 494.1608. Found: 494.1598.

Example 18

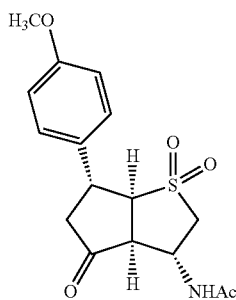

29

As shown in Scheme 7: Compound 28 (1.61 g, 3.42 mmol) was dissolved in 50 mL acetone. N-Methylmorpholine-N-oxide (802 mg, 6.84 mmol) was added, followed by OsO$_4$ (1.08 mL, 4% in water, 0.171 mmol). The reaction mixture was stirred at 0° C. for 30 minutes, then warmed to room temperature and stirred for 1 hour. The reaction mixture was partitioned between 0.5 M aqueous sodium thiosulfate and ethyl acetate. The aqueous layer was washed with ethyl acetate, and the combined organic extracts were dried with sodium sulfate and concentrated in vacuo. The crude triol was dissolved in 50 mL acetone and 10 mL water. Sodium periodate (2.93 g, 13.7 mmol) was added, and the reaction mixture was stirred for 16 hours. The reaction mixture was partitioned between 0.5 M aqueous sodium thiosulfate and ethyl acetate. The aqueous layer was washed with ethyl acetate, and the combined organic extracts were dried with sodium sulfate and concentrated in vacuo. Recrystallization from ethyl acetate and a minimum amount of methanol afforded 589 mg (51% over 2 steps) of 29 as a white solid. IR (film) 3335 (br), 1751, 1652, 1255, 1114 cm$^{-1}$; $^1$H NMR (CD$_3$S(O)CD$_3$ 300 MHz) δ 8.39 (d, J=7.2 Hz, 1H), 7.32 (d, J=8.6 Hz, 2H), 6.93 (d, J=8.6 Hz, 2H), 4.46 (pentet, J=6.3 Hz, 1H), 4.10 (dd, J=9.8, 8.1 Hz, 1H), 3.93-3.81 (m, 1H), 3.74 (s, 3H), 3.60 (dd, J=13, 6.9 Hz, 1H), 3.51 (dd, J=10, 6.0 Hz, 1H), 3.13 (dd, J=13, 7.1 Hz, 1H), 2.79 (dd, J=18, 8.6 Hz, 1H), 2.68 (dd, J=18, 10 Hz, 1H), 1.95 (s, 3H); $^{13}$C NMR (CD$_3$S(O)CD$_3$ 75 MHz) δ 211.3 (C), 169.2 (C), 158.3 (C), 133.6 (C), 128.4 (CH), 114.1 (CH), 67.3 (CH), 55.1 (CH$_2$), 55.1 (CH$_3$), 54.2 (CH), 46.0 (CH$_2$), 45.1 (CH), 33.8 (CH), 22.5 (CH$_3$); MS (ES+) m/z 360 (100); HRMS calcd for C$_{16}$H$_{19}$NO$_5$S (M+Na): 360.0876. Found: 360.0870.

Example 19

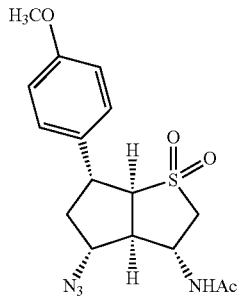

30

As shown in Scheme 7: Compound 29 (508 mg, 1.50 mmol) was dissolved in 20 mL tetrahydrofuran. The solution was cooled to −78° C., then L-Selectride (2.20 mL, 1 M in THF, 2.26 mmol) was added. The solution was stirred at −78° C. for 1 hour. The reaction mixture was quenched with methanol at −78° C., then warmed to room temperature and partitioned between ethyl acetate and 10% sodium bicarbonate. The aqueous layer was washed with ethyl acetate, and the combined organic extracts were dried with sodium sulfate and concentrated in vacuo to provide 513 mg of the desired alcohol as a white solid. The crude product was carried to the next step with no further purification.

The alcohol intermediate (511 mg, 1.51 mmol) was dissolved in 5 mL pyridine. The solution was cooled to 0° C., then methanesulfonyl chloride (176 μL, 2.26 mmol) was added. The solution was stirred at room temperature for 16 hours. The reaction mixture was concentrated in vacuo, then partitioned between dichloromethane and water. The aqueous layer was washed with ethyl acetate, and the combined organic extracts were dried with sodium sulfate and concentrated in vacuo to provide 564 mg of the desired mesylate as an orange solid. The crude intermediate (564 mg, 1.35 mmol) was dissolved in 5 mL dimethylformamide. Sodium azide (351 mg, 5.41 mmol) was added. The reaction mixture was heated at 80° C. for 16 hours. The reaction mixture was partitioned between dichloromethane and water. The aqueous layer was washed with dichloromethane, and the combined organic extracts were dried with sodium sulfate and concentrated in vacuo. Flash column chromatography (dichloromethane:EtOAc 4:1 to dichloromethane:EtOAc 1:1) afforded 171 mg (31% over 3 steps) of 30 as a light brown solid. IR (film) 3354 (br), 2103, 1661, 1252, 1119 cm$^{-1}$; $^1$H NMR (CD$_3$OD 300 MHz) 7.27 (d, J=8.7 Hz, 2H), 6.89 (d, J=8.7 Hz, 2H), 4.53 (dt, J=8.0, 6.3 Hz, 1H), 4.17-4.02 (m, 1H), 3.89 (dd, J=9.8, 8.1 Hz, 1H), 3.78 (s, 3H), 3.79-3.67 (m, 2H), 3.55 (dd, J=13, 6.0 Hz, 1H), 3.24 (dd, J=13, 8.1 Hz, 1H), 3.04-2.94 (m, 1H), 2.59 (dt, J=12, 6.3 Hz, 1H), 2.00 (s, 3H); $^{13}$C NMR (CD$_3$OD 75 MHz) δ173.2 (C), 160.3 (C), 133.8 (C), 129.4 (CH), 115.2 (CH), 70.5 (CH), 66.3 (CH), 56.5 (CH$_2$), 56.1 (CH), 55.7 (CH$_3$), 49.6 (CH), 44.0 (CH), 42.4 (CH$_2$), 22.5 (CH$_3$); MS (ES+) m/z 387 (100); HRMS calcd for C$_{16}$H$_{20}$N$_4$O$_4$S (M+Na): 387.1098. Found: 387.1098.

Example 20

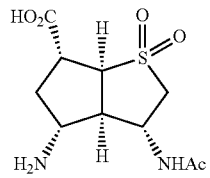

31

As shown in Scheme 7: Compound 29 (121 mg, 0.332 mmol) was dissolved in CCl$_4$ (2 mL), acetonitrile (2 mL) and water (6 mL). NaIO$_4$ (1.07 g, 4.99 mmol) was added, followed by RuCl$_3$ (3.5 mg, 0.017 mmol). The reaction mixture was stirred for 16 hours, and then partitioned EtOAc and water. The aqueous layer was washed with ethyl acetate, and the combined organic fractions were dried with Na$_2$SO$_4$ then concentrated in vacuo at 30° C. The crude solid was dissolved in ethyl acetate, filtered through cotton, then concentrated in vacuo to provide 89 mg of crude carboxylic acid as a white solid. The crude product was carried to the next step with no further purification. IR (film) 3352 (br), 2105, 1731, 1654, 1253, 1121 cm$^{-1}$; $^1$H NMR (CD$_3$S(O)CD$_3$ 300 MHz) δ 8.34 (d, J=7.3 Hz, 1H), 4.20-4.05 (m, 2H), 3.60-3.47 (m, 1H), 3.41-3.25 (m, 2H), 3.15 (dd, J=13, 9.3 Hz, 1H), 2.91-2.80 (m, 1H), 2.39-2.26 (m, 1H), 2.16-2.03 (m, 1H), 1.85 (s, 3H); $^{13}$C NMR (CD$_3$S(O)CD$_3$ 75 MHz) δ 173.0 (C), 170.4 (C), 64.0 (CH), 63.4 (CH), 54.5 (CH$_2$), 53.9 (CH), 47.0 (CH), 42.5 (CH), 34.6 (CH$_2$), 22.6 (CH$_3$); MS (ES+) m/z 325 (100); HRMS calcd for C$_{10}$H$_{14}$N$_4$O$_5$S (M+Na): 325.0577. Found: 325.0579.

The azido acid intermediate (crude, 36 mg, 0.119 mmol) was dissolved in methanol (10 mL). Pd/C 10% (~10 mg) was added, then H$_2$ was bubbled through the solution for 5 minutes. The reaction mixture was stirred under 1 atm H$_2$ for 16 hours. The reaction mixture was filtered through cotton, then concentrated in vacuo to provide 28 mg (73% over 2 steps) of the 30 as a white solid. The crude product was carried to the next step with no further purification. IR (film) 3351 (br), 3248 (br), 1727, 1653, 1299, 1122 cm$^{-1}$; $^1$H NMR (D$_2$O 300 MHz) δ 4.49-4.40 (m, 1H), 4.28 (dd, J=10, 6.1 Hz, 1H), 3.81 (dd, J=13, 6.7 Hz, 1H), 3.67 (dd, J=14, 6.7 Hz, 1H), 3.51-3.40 (m, 2H), 3.23 (dt, J=10, 5.8 Hz, 1H), 2.67-2.54 (m, 1H), 2.18-2.06 (m, 1H), 1.85 (s, 3H); $^{13}$C NMR (D$_2$O 75 MHz) δ 178.0 (C), 174.4 (C), 65.6 (CH), 55.1 (CH), 53.3 (CH$_2$), 53.1 (CH), 52.8 (CH), 47.9 (CH), 34.6 (CH$_2$), 21.9 (CH$_3$); MS (ES+) m/z 299 (100); HRMS calcd for C$_{10}$H$_{16}$N$_2$O$_5$S (M+Na): 299.0672. Found: 299.0678.

Example 21

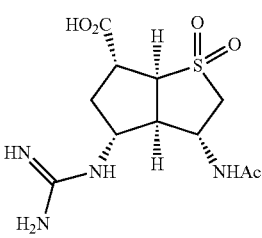

32

As shown in Scheme 7: Compound 31 (crude, 27 mg, 0.0978 mmol) was dissolved in DMF (3 mL). Triethylamine (68 µL, 0.489 mmol) was added, followed by HgCl$_2$ (27 mg, 0.0978 mmol). 1,3-bis(benzyloxycarbonyl)-2-methylisothiourea (35 mg, 0.0978 mmol) was added and the reaction mixture was stirred for 16 hours. The reaction mixture was concentrated in vacuo. Flash column chromatography (100:1 dichloromethane:methanol to 10:1 dichloromethane:methanol) afforded 15 mg of Cbz-protected 32 as a white solid. IR (film) 3313 (br), 1771, 1714, 1651, 1302, 1116 cm$^{-1}$; $^1$H NMR (CD$_3$COD 500 MHz) δ 7.43-7.29 (m, 10H), 5.20 (s, 2H), 5.17 (s, 1H), 4.42 (dd, J=11, 6.0 Hz, 1H), 4.31 (dd, J=10, 6.9 Hz, 1H), 4.23-4.17 (m, 1H), 3.73-3.65 (m, 1H), 3.51 (dd, J=13, 6.5 Hz, 1H), 3.22 (dd, J=13, 6.0 Hz, 1H), 3.04-2.97 (m, 1H), 2.63-2.54 (m, 1H), 1.94 (s, 3H), 1.93-1.89 (m, 1H); $^{13}$C NMR (CD$_3$COD 125 MHz) δ 173.7 (C), 173.3 (C), 155.9 (C), 155.1 (C), 153.1 (C), 137.0 (C), 136.9 (C), 129.6 (CH), 129.6 (CH), 129.5 (CH), 129.4 (CH), 129.4 (CH), 129.3 (CH), 68.6 (CH$_2$), 68.5 (CH$_2$), 64.4 (CH), 55.9 (CH), 55.7 (CH), 55.6 (CH$_2$), 54.8 (CH), 46.5 (CH), 38.0 (CH$_2$), 22.5 (CH$_3$); MS (ES+) m/z 609 (100); HRMS calcd for C$_{27}$H$_{26}$N$_4$O$_7$S (M+Na): 609.1626. Found: 609.1614.

The protected guanidine (15 mg, 0.026 mmol) was dissolved in methanol (8 mL). Acetic acid (~100 µL) was added, followed by Pd/C 10% (~10 mg). The reaction mixture was stirred inside a Parr reactor pressurized to 300 PSI H$_2$ for 16 hours. The reaction mixture was filtered through cotton, diluted with cyclohexane (10 mL) then concentrated in vacuo to provide 8 mg (26% over 2 steps) of guanidine 32 as a white solid. IR (film) 3345 (br), 1726, 1659, 1650, 1310, 1119 cm$^{-1}$; $^1$H NMR (D$_2$O 500 MHz) δ 4.49-4.40 (m, 1H), 4.16-4.08 (m, 1H), 4.07-3.97 (m, 1H), 3.71-3.60 (m, 1H), 3.58-3.50 (m, 1H), 3.44-3.35 (m, 1H), 3.01-2.91 (m, 1H), 2.53-2.40 (m, 1H), 1.99 (s, 3H), 1.89-1.79 (m, 1H); $^{13}$C NMR (D$_2$O 125 MHz) δ 176.5 (C), 174.3 (C), 160.9 (C), 72.4 (CH), 63.7 (CH), 62.7 (CH$_2$), 54.1 (CH$_2$), 54.0 (CH), 47.8 (CH), 44.0 (CH), 21.9 (CH$_3$); MS (ES+) m/z 341 (100); HRMS calcd for C$_{11}$H$_{18}$N$_4$O$_5$S (M+Na): 341.0890. Found: 341.0890.

Example 22

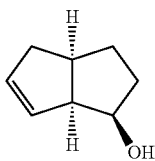

6

As shown in Scheme 9: Peracetic acid (32 wt % in dilute acidic acid; 56.2 mL, 267 mmol, 1.33 equiv) was added via syringe pump (1.5 mL/min) to a stirred solution of 1,3-cyclooctadiene (25 mL, 200 mmol, 1 equiv) and Na$_2$CO$_3$ (85.1 g, 803 mmol, 4 equiv) in DCM (300 mL) at 0° C. The reaction mixture was allowed to warm to room temperature over 2 hours and then filtered and washed with DCM (50 mL). A saturated solution of aq. NaHCO$_3$ was added to the filtrate, the organic phase was separated, and the aqueous phase was extracted with DCM (2×50 mL). The organic extracts were pooled and washed with brine, dried over anhydrous Na$_2$SO$_4$, filtered, and concentrated under reduced pressure. The resulting monoepoxide was used without purification as a yellow oil (21.3 g, 85.3%). $^1$H NMR (CDCl$_3$) 5.81-5.72 (m, 1H), 5.59 (dt, J=11.1, 1.2 Hz, 1H), 3.46 (dt, J=4.1, 1.2 Hz, 1H), 3.11 (dtd, J=9.4, 4.0, 0.9 Hz, 1H), 2.38-2.24 (m, 1H), 2.15-1.95 (m, 2H), 1.84-1.70 (m, 1H), 1.69-1.59 (m, 2H), 1.53-1.33 (m, 2H).

A 2 L 3-neck round bottom flask was equipped with a thermometer, condenser, and rubber septum and was charged with Et$_2$O (300 mL) and Et$_2$NH (39.2 mL, 377 mmol, 2.26 equiv). The solution was cooled to 0° C. and n-BuLi (2.5 M in hexanes; 151 mL, 377 mmol, 2.26 equiv) was added dropwise via cannula. The resulting solution was slowly warmed to 35° C. over 2 hours at which point the heat source was removed and the previously synthesized 3,4-epoxycyclooctene (20.7 g, 167 mmol, 1 equiv) dissolved in Et$_2$O (20 mL) was added at such a rate that the reaction temperature was maintained between 30-35° C. This solution was then gently refluxed for 18 hours, cooled to 0° C., and slowly quenched with the sequential addition of MeOH, H$_2$O, and 10% HCl until an acidic pH was reached. The organic phase was separated and the aqueous phase was extracted with Et$_2$O (2×30 mL). The organic extracts were pooled and washed with saturated aq. NaHCO$_3$, dried over anhydrous Na$_2$SO$_4$, filtered, and concentrated under reduced pressure. The crude reaction product was absorbed onto silica gel, washed with 40:1 hexanes-EtOAc (150 mL), and eluted using 1:1 hexanes-EtOAc (400 mL) to afford 19.5 g (94.5%) of 6 as a clear red oil. $^1$H NMR (CDCl$_3$) 5.81 (dd, J=3.9, 1.7 Hz, 1H), 5.60-5.54 (m, 1H), 4.16 (dd, J=11.2, 5.6 Hz, 1H), 3.26-3.14 (m, 1H), 2.71-2.53 (m, 2H), 2.11-1.95 (m, 1H), 1.85-1.71 (m, 1H), 1.70-1.47 (m, 2H), 1.34 (dtd, J=18.3, 6.3, 5.6 Hz, 1H); $^{13}$C NMR (CDCl$_3$) 134.41 (CH), 127.84 (CH), 74.79 (CH), 55.92 (CH), 41.69 (CH$_2$), 39.58 (CH), 34.88 (CH$_2$), 31.10 (CH$_2$); IR (neat, cm$^{-1}$) 3350 (s), 2942 (s), 2865 (s), 2845 (s), 1447 (m), 1363 (m), 1334 (m), 1172 (w), 1086 (s), 1065 (s), 711 (s).

Example 23

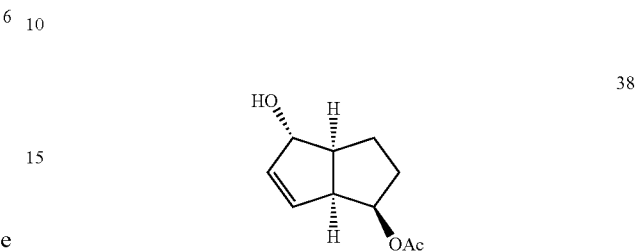

38

As shown in Scheme 9: Alcohol 6 (19.5 g, 158 mmol, 1.00 equiv) was dissolved in benzene (distilled over CaH; 220 mL) and the following reagents were added: acetic anhydride (23.9 mL, 252 mmol, 1.60 equiv), pyridine (20.4 mL, 252 mmol, 1.6 equiv), and DMAP (1.9 g, 15 mmol, 0.1 equiv). The flask was equipped with a small oven-dried condenser and the reaction mixture was heated to 50° C. for 18 hours. The solution was then cooled to room temperature and a saturated solution of aq. NH$_4$Cl was added. The organic phase was separated and the aqueous phase was extracted with Et$_2$O (2×30 mL). The organic extracts were washed with brine, dried over anhydrous Na$_2$SO$_4$, filtered, and concentrated under reduced pressure. Polar contaminants were removed by passing the crude material through a thick silica gel plug and eluting with 2:1 hexanes-EtOAc to afford 21.1 g (80.7%) of acetate-protected 6 as a clear yellow oil. $^1$H NMR (CDCl$_3$) 5.75 (ddd, J=5.9, 2.0, 4.1 Hz, 1H), 5.43 (ddd, J=5.9, 2.3, 4.7 Hz, 1H), 5.09 (ddd, J=7.3, 5.6, 7.6 Hz, 1H), 3.43-3.33 (m, 1H), 2.76-2.60 (m, 2H), 2.09 (ddd, J=13.8, 5.0, 2.3 Hz, 1H), 2.03 (s, 3H), 1.88-1.73 (m, 2H), 1.70-1.55 (m, 1H), 1.46-1.34 (m, 1H).

This intermediate (6.16 g, 37.1 mmol, 1 equiv) was dissolved in 1,4-dioxane and SeO$_2$ (6.17 g, 55.6 mmol, 1.5 equiv) was added. The flask was equipped with a small oven-dried condenser and the heterogeneous mixture was heated to 85° C. for 18 hours. The reaction was cooled and solid particulate was filtered by passing the mixture through a thick bed of Celite 545. To the filtrate was added saturated aq. NH$_4$Cl, and the organic phase was separated. The aqueous phase was extracted with Et$_2$O (2×20 mL) and the organic extracts were further washed with dH$_2$O and brine, dried over anhydrous Na$_2$SO$_4$, filtered, and concentrated under reduced pressure. Crude material contained a mixture of 38 and the corresponding enone product (33), which could be separated by chromatography (1:2 hexanes-EtOAc) to afford 3.83 g (56.7%) of 38 and 0.75 g (11.2%) of enone 33. $^1$H NMR (CDCl$_3$) 5.89 (dt, J=5.6, 2.0 Hz, 1H), 5.76 (ddd, J=5.6, 2.3, 0.9 Hz, 1H), 5.15-5.02 (m, 1H), 4.56-4.49 (m, 1H), 3.56 (dtd, J=12.0, 1.2, 7.3 Hz, 1H), 2.50-2.41 (m, 1H), 2.03 (s, 3H), 1.90-1.76 (m, 2H), 1.63-1.40 (m, 3H); $^{13}$C NMR (CDCl$_3$)

170.81 (C), 135.07 (CH), 134.08 (CH), 85.73 (CH), 76.25 (CH), 52.11 (CH), 50.16 (CH), 29.80 (CH$_2$), 27.18 (CH$_2$), 21.06 (CH$_3$).

Example 24

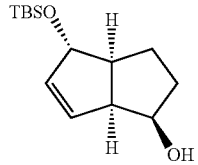

39

As shown in Scheme 9: Compound 38 (1.59 g, 8.73 mmol, 1 equiv) was dissolved in DCM (50 mL), the solution was cooled to 0° C., and the following reagents were added: TBSCl (1.84 g, 12.2 mmol, 1.4 equiv), Et$_3$N (3.65 mL, 26.2 mmol, 3 equiv), and DMAP (107 mg, 0.873 mmol, 0.1 equiv). The resulting solution was then stirred at room temperature for 18 hours, after which Et$_2$O (10 mL) was added and solid particulate was filtered out by passing the mixture through a thick plug of Celite 545. To the filtrate was added saturated aq. NaHCO$_3$ and the organic phase was separated. The aqueous phase was extracted with Et$_2$O (2×20 mL) and the organic extracts were washed with brine, dried over anhydrous Na$_2$SO$_4$, filtered, and concentrated under reduced pressure. The crude product was purified by chromatography to afford 1.95 g (75.3%) of TBS-protected 38 as a light yellow oil. $^1$H NMR (CDCl$_3$) 5.75 (dt, J=5.6, 2.0 Hz, 1H), 5.67 (ddd, J=5.6, 2.3, 0.9 Hz, 1H), 5.05 (dt, J=5.6, 7.6 Hz, 1H), 4.56-4.52 (m, 1H), 3.55 (dtd, J=10.0, 2.3, 7.6 Hz, 1H), 2.49-2.40 (m, 1H), 2.02 (s, 3H), 1.89-1.73 (m, 2H), 1.61-1.46 (m, 2H), 0.90 (s, 9H), 0.09 (s, 3H), 0.08 (s, 3H).

This intermediate (1.68 g, 5.67 mmol, 1 equiv) was dissolved in MeOH (20 mL) and K$_2$CO$_3$ (4.70 g, 34.0 mmol, 6 equiv) was added. After stirring at room temperature for 6 hours, a solution of saturated aq. NaHCO$_3$ was added and the organic phase was separated. The aqueous phase was extracted with Et$_2$O (2×5 mL) and the organic extracts were washed with brine, dried over anhydrous Na$_2$SO$_4$, filtered, and concentrated under reduced pressure. The crude product was purified by chromatography to afford 1.47 g (quantitative yield) of 39 as a light yellow oil. $^1$H NMR (CDCl$_3$) 5.84 (br s, 2H), 4.58-4.54 (m, 1H), 4.25-4.15 (m, 1H), 3.41 (ddd, J=7.3, 2.6, 7.6 Hz, 1H), 2.45 (tdd, J=8.5, 3.8, 2.3 Hz, 1H), 1.90-1.79 (m, 1H), 1.78-1.66 (m, 1H), 1.61-1.49 (m, 2H), 0.90 (s, 9H), 0.09 (s, 6H); $^{13}$C NMR (CDCl$_3$) 137.08 (CH), 131.87 (CH), 86.69 (CH), 73.89 (CH), 55.04 (CH), 51.10 (CH), 31.28 (CH$_2$), 27.55 (CH$_2$), 25.97 (CH$_3$), 18.29 (C), -4.43 (CH$_3$), -4.49 (CH$_3$); IR (neat, cm$^{-1}$) 3368 (m, br), 3058 (w), 1472 (m), 1463 (m), 1370 (m), 1254 (m), 1117 (m), 1060 (s), 868 (m), 836 (m), 774 (m); HRMS (ESI) calcd for C$_{14}$H$_{26}$O$_2$Si+ Na$^+$ 277.15942. found 277.15942.

Example 25

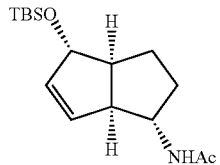

40

As shown in Scheme 9: Compound 39 (9.90 g, 38.9 mmol, 1 equiv) was dissolved in DCM (200 mL) and the solution was cooled to 0° C. To the solution was added Et$_3$N (10.9 mL, 77.8 mmol, 2 equiv) and MsCl (6.05 mL, 77.8 mmol, 2 equiv), after which the reaction was allowed to warm to room temperature over 18 hours. The crude mixture was concentrated under reduced pressure and passed through a silica gel plug using 2:1 hexanes-EtOAc to afford 12.35 g (95.4%) of the desired mesylate as a light yellow oil. $^1$H NMR (CDCl$_3$) 5.77-5.71 (m, 2H), 4.92 (dt, J=5.4, 7.7 Hz, 1H), 4.48-4.44 (m, 1H), 3.56-3.48 (m, 1H), 2.92 (s, 3H), 2.42-2.33 (m, 1H), 1.89-1.79 (m, 1H), 1.79-1.69 (m, 1H), 1.69-1.58 (m, 1H), 1.58-1.46 (m, 1H), 0.81 (s, 9H), 0.0043 (s, 3H), -0.0009 (s, 3H).

To the mesylate (12.34 g, 37.1 mmol, 1 equiv) was added DMF (130 mL) and NaN$_3$ (7.24 g, 111.4 mmol, 3 equiv), and the reaction was heated to 55° C. for 18 hours. A solution of saturated NH$_4$Cl was added and the organics were extracted with Et$_2$O, washed with H$_2$O, and concentrated under reduced pressure. The crude material was passed through a silica gel plug using 9:1 hexanes-EtOAc to provide 8.29 g (80.0%) of the desired azide as a clear colorless oil. $^1$H NMR (CDCl$_3$) 5.68 (ddd, J=5.7, 2.2, 0.6 Hz, 1H), 5.62 (dt, J=5.6, 2.0 Hz, 1H), 4.44-4.40 (m, 1H), 3.65-3.60 (m, 1H), 3.28-3.21 (m, 1H), 2.53-2.44 (m, 1H), 2.03-1.85 (m, 1H), 1.66-1.42 (m, 2H), 0.82 (s, 9H), 0.0081 (s, 3H), -0.0008 (s, 3H).

To this azide (7.54 g, 27.0 mmol, 1 equiv) was added THF (150 mL) and the solution was sparged with argon. Using a syringe pump, PMe$_3$ (1M in THF; 40.5 mL, 40.5 mmol, 1.5 equiv) was added at 0.74 mL/min and the solution was stirred at room temperature for 1 hour. Then AcOH (4.63 mL, 80.9 mmol, 3 equiv) was added via syringe pump at 0.34 mL/min and the reaction was left stirring at room temperature for 18 hours. The reaction mixture was concentrated and transferred to a separatory funnel using DCM. Saturated aqueous NaCl was added and the organic layer was isolated, dried with Na$_2$SO$_4$, filtered, and concentrated under reduced pressure. The crude viscous green oil was placed onto a silica gel plug, rinsed with 4:1 hexanes-EtOAc, and then eluted with pure EtOAc to afford 6.43 g (80.6%) of 40. $^1$H NMR (CDCl$_3$) 5.82 (ddd, J=5.6, 2.3, 0.9 Hz, 1H), 5.56 (dt, J=5.6, 2.0 Hz, 1H), 5.42 (br s, 1H), 4.46-4.41 (m, 1H), 3.92-3.83 (m, 1H), 3.02 (dt, J=7.9, 2.6 Hz, 1H), 2.50-2.40 (m, 1H), 1.89 (s, 3H), 1.88-1.78 (m, 1H), 1.73-1.60 (m, 1H), 1.50-1.38 (m, 2H), 0.82 (s, 9H), 0.0073 (s, 3H), -0.0005 (s, 3H); $^{13}$C NMR (CDCl$_3$) 169.60 (C), 135.95 (CH), 133.66 (CH), 85.67 (CH), 57.64 (CH), 54.74 (CH), 50.70 (CH), 31.95 (CH$_2$), 29.41 (CH$_2$), 25.96 (CH$_3$), 23.48 (CH$_3$), 18.29 (C), -4.46 (CH$_3$); IR (neat, cm$^{-1}$) 3281 (m, br), 3058 (w), 1648 (s), 1551 (s), 1472

(m), 1463 (m), 1445 (w), 1373 (m), 1256 (m), 1114 (m), 1061 (s); HRMS (ESI) calcd for $C_{16}H_{29}NO_2Si+Na^+$ 318.18597. found 318.18581.

Example 26

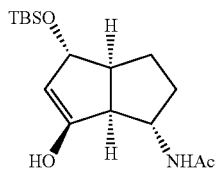

As shown in Scheme 9: To a solution of 40 (4.00 g, 13.5 mmol, 1 equiv) in THF (60 mL) at 0° C. was added $BH_3$THF (1M in THF; 16.2 mL, 16.2 mmol, 1.2 equiv) via syringe pump at 0.49 mL/min. The reaction was then stirred for 1 hour at 0° C. After the dropwise addition of MeOH had quenched excess the borane, $H_2O_2$ (30 wt %; 4.15 mL, 40.6 mmol, 3 equiv) and NaOH (2 N, 10.2 mL, 20.3 mmol, 1.5 equiv) were added and the reaction was left stirring open to air for 30 minutes. A saturated solution of $NH_4Cl$ was added to the reaction at 0° C. and the solution was warmed to room temperature. Ethyl acetate was added and the organic layer was separated, washed with $H_2O$, dried over anhydrous $Na_2SO_4$, filtered, and concentrated. The crude material contained a mixture of regioisomers, which were separated by a combination of column chromatography and re-crystallization, providing 670 mg (15.8%) of 40. $^1$H NMR ($CDCl_3$) 5.75 (br d, J=6.7 Hz, 1H), 4.03-3.95 (m, 1H), 3.95-3.90 (m, 1H), 3.64 (d, J=9.7 Hz, 1H), 3.64-3.44 (m, 1H), 2.56 (q, J=9.5 Hz, 1H), 2.25 (dd, J=9.7, 8.5 Hz, 1H), 2.00-1.90 (m, 1H), 1.89 (s, 3H), 1.88-1.82 (m, 2H), 1.78-1.69 (m, 1H), 1.27-1.11 (m, 1H), 1.02-0.86 (m, 1H), 0.80 (s, 9H), −0.0008 (s, 3H), −0.0067 (s, 3H); $^{13}$C NMR ($CDCl_3$) 170.20 (C), 79.71 (CH), 77.30 (CH), 59.65 (CH), 55.23 (CH), 51.45 (CH), 40.59 ($CH_2$), 34.19 ($CH_2$), 28.41 ($CH_2$), 25.72 ($CH_3$), 23.31 ($CH_3$), 17.90 (C), −4.99 ($CH_3$); IR (neat, $cm^{-1}$) 3288 (s br), 3078 (w), 1652 (s), 1557 (s), 1472 (m), 1463 (m), 1447 (w), 1376 (m), 1257 (m), 1115 (m), 1066 (s); HRMS (ESI) calcd for $C_{16}H_{29}NO_2Si+Na^+$ 336.19653. found 336.19639.

Example 27

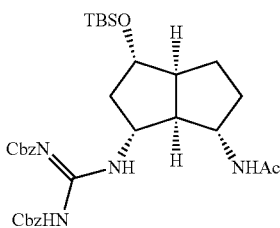

As shown in Scheme 9: To a solution of $PPh_3$ (520 mg, 1.98 mmol, 1.8 equiv) in THF (10 mL) at 0° C. was added DIAD (411 µL, 1.98 mmol, 1.8 equiv). After stirring at 0° C. for 1 hour, a freshly prepared and titrated solution of $HN_3$ (1.69 M in benzene; 1.20 mL, 1.98 mmol, 1.8 equiv) was added slowly, followed immediately by the addition of a solution of 41 (345 mg, 1.10 mmol, 1 equiv) in 5 mL of THF. The resulting solution was stirred at 0° C. for a further 1 hour, then warmed to room temperature over 18 hours. The reaction was concentrated under reduced pressure and purified by column chromatography to provide 183 mg (49.2%) of the intermediate azide. $^1$H NMR ($CDCl_3$) 5.68 (br d, J=6.4 Hz, 1H), 4.29 (dt, J=9.5, 6.8 Hz, 1H), 4.14-4.02 (m, 1H), 3.85-3.79 (m, 1H), 2.53-2.35 (m, 2H), 2.06 (ddt, J=3.1, 12.1, 6.1 Hz, 1H), 1.94 (s, 3H), 1.97-1.87 (m, 1H), 1.88-1.78 (m, 1H), 1.73 (ddd, J=13.0, 9.8, 4.1 Hz, 1H), 1.40-1.23 (m, 1H), 1.10 (dddd, J=13.0, 11.1, 7.9, 6.1 Hz, 1H), 0.83 (s, 9H), −0.0009 (s, 6H).

The azide (292 mg, 0.86 mmol, 1 equiv) was dissolved in MeOH (20 mL) and the atmosphere was purged with $H_2$ gas. Palladium on carbon (10 wt %; 92 mg, 0.09 mmol, 0.1 equiv) was added, the atmosphere was purged again, and the reaction was left stirring at room temperature under an atmosphere of $H_2$ gas until complete reduction was indicated by TLC. The spent catalyst was filtered and the resulting solution was concentrated. The reduced product (42) was dissolved directly in DMF (5 mL) and $Et_3N$ (415 µL, 2.98 mmol, 3.5 equiv), 1,3-bis(benzyloxycarbonyl)-2-methyl-2-thiopseudourea (353 mg, 0.94 mmol, 1.1 equiv), and $HgCl_2$ (254 mg, 0.94 mmol, 1.1 equiv) were added. The resulting solution was stirred at room temperature for 18 hours, then filtered through Celite. To the filtrate was added brine, and the organics were extracted with EtOAc, dried over anhydrous $Na_2SO_4$, filtered, and concentrated. Purification by column chromatography provided 403 mg (76.1%) of 43. $^1$H NMR ($CDCl_3$) 11.55 (br s, 1H), 8.50 (d, J=5.6 Hz, 1H), 7.41-7.25 (m, 10H), 5.33 (d, J=7.0 Hz, 1H), 5.22-5.05 (m, 4H), 4.46 (ddt, J=12.9, 7.0, 6.1 Hz, 1H), 3.79 (d, J=5.6 Hz, 1H), 3.78-3.65 (m, 1H), 2.64 (dt, J=8.5, 9.1 Hz, 1H), 2.41 (dt, J=9.7, 9.4 Hz, 1H), 2.15 (p, J=5.6 Hz, 1H), 1.99-1.83 (m, 2H), 1.66 (td, J=6.3, 4.1 Hz, 1H), 1.61 (s, 3H), 1.20-1.04 (m, 1H), 1.04-0.91 (m, 1H), 0.83 (s, 914), −0.0005 (s, 3H), −0.0078 (s, 3H); $^{13}$C NMR ($CDCl_3$) 169.39 (C), 163.40 (C), 156.26 (C), 153.64 (C), 137.01 (C), 134.59 (C), 128.71 (CH), 128.64 (CH), 128.54 (CH), 128.46 (CH), 128.08 (CH), 128.03 (CH), 75.73 (CH), 68.30 ($CH_2$), 67.25 ($CH_2$), 52.33 (CH), 52.10 (CH), 51.89 (CH), 49.27 (CH), 38.43 (CH), 34.50 ($CH_2$), 29.00 ($CH_2$), 25.83 ($CH_3$), 22.83 ($CH_3$), 18.13 (C), −4.83 ($CH_3$), −4.88 ($CH_3$); IR (neat, $cm^{-1}$) 3326 (s br), 3091 (m), 3066 (m), 3035 (m), 2244 (w), 1732 (s), 1661 (s), 1651 (s), 1634 (s), 1574 (s), 1557 (s), 1498 (m), 1455 (s), 1385 (s), 1126 (s), 1053 (s); HRMS (ESI) calcd for $C_{33}H_{46}N_4O_6Si+H^+$ 609.21999. found 609.21983.

Example 28

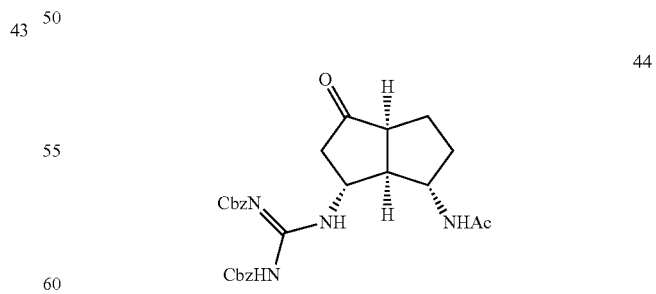

As shown in Scheme 9: A solution of 43 (341 mg, 0.548 mmol, 1 equiv) in THF (6 mL) with activated 4 Å molecular sieves was cooled to 0° C. and TBAF (1M in THF; 2.71 mL, 2.74 mmol, 5 equiv) was added. The solution was warmed to room temperature and monitored by TLC until completion was indicated by consumption of starting material. A saturated solution of NH$_4$Cl was added to the reaction and the organics were extracted with EtOAc, washed with brine, dried over Na$_2$SO$_4$, and concentrated by rotary evaporation. Purification by column chromatography provided 210 mg (75.3%) of the free alcohol. $^1$H NMR (CDCl$_3$) 11.52 (br s, 1H), 8.52 (br d, J=6.4 Hz, 1H), 7.38-7.23 (m, 10H), 5.49 (br d, J=7.3 Hz, 1H), 5.22-5.02 (m, 4H), 4.54 (s, J=6.7 Hz, 1H), 3.85-3.70 (m, 1H), 3.70-3.63 (m, 1H), 3.19 (br s, 1H), 2.66 (dt, J=8.5, 9.1 Hz, 1H), 2.45 (q, J=9.3 Hz, 1H), 2.06 (p, J=5.7 Hz, 1H), 1.96-1.76 (m, 2H), 1.67 (s, 3H), 1.64-1.53 (m, 1H), 1.19-1.04 (m, 1H), 0.94-0.76 (m, 1H).

The product described above (65.0 mg, 0.128 mmol, 1 equiv) was dissolved in DCM (5 mL) with 4 Å crushed molecular sieves and PCC (60.6 mg, 0.281 mmol, 2.2 equiv) was added. The reaction was left stirring at room temperature for 18 hours, and then filtered through Celite. To the filtrate was added a saturated solution of NH$_4$Cl and the organics were extracted with DCM, dried over Na$_2$SO$_4$, filtered, and concentrated. The crude material was purified by column chromatography to afford 57.5 mg (88.7%) of 44 as a white powder. $^1$H NMR (CDCl$_3$) 8.63 (br d, J=6.2 Hz, 1H), 7.40-7.25 (m, 10H), 5.44 (br d, J=7.7 Hz, 1H), 5.17 (s, 2H), 5.12 (s, 2H), 4.78-4.69 (m, 1H), 4.15-4.06 (m, 1H), 2.88 (dt, J=7.5, 9.3 Hz, 1H). 2.80-2.69 (m, 2H), 2.42-2.32 (m, 1H), 2.23-2.15 (m, 1H), 2.11-2.02 (m, 1H), 1.80 (s, 3H), 1.75-1.64 (m, 1H), 1.44-1.34 (m, 1H); $^{13}$C NMR (CDCl$_3$) 216.05 (C), 169.66 (C), 163.40 (C), 156.06 (C), 153.43 (C), 136.64 (C), 134.46 (C), 128.83 (CH), 128.73 (M), 128.69 (CH), 128.53 (CH), 128.47 (CH), 128.09 (CH), 68.42 (CH$_2$), 67.30 (CH$_2$), 51.77 (CH), 51.13 (CH), 48.74 (CH), 48.01 (CH), 41.02 (CH$_2$), 34.20 (CH$_2$), 25.55 (CH$_2$), 23.11 (CH$_3$); IR (neat, cm$^{-1}$) 3319 (br w), 1736 (s), 1640 (s), 1618 (s), 1571 (m), 1431 (m), 1382 (m), 1358 (m), 1327 (m), 1260 (s), 1206 (m), 1136 (w), 1054 (m); HRMS (ESI) calcd for C$_{27}$H$_{30}$N$_4$O$_6$+H$^+$ 507.22381. found 507.22381.

Example 29

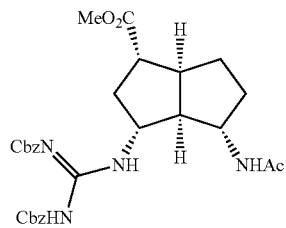

As shown in Scheme 9: A solution of 2-trimethylsilyl-1,3-dithiane (242 μL, 1.30 mmol, 5 equiv) in THF (0.5 mL) was cooled to 0° C. and n-BuLi (2.5 M in hexanes; 519 μL, 1.30 mmol, 5 equiv) was added dropwise. After stirring at 0° C. for 1 hour, the solution was cooled to −42° C. and a solution of 9 (131.4 mg, 0.26 mmol, 1 equiv) in THF (2 mL) was added via syringe. The solution was stirred at −42° C. for 1 hour, and then warmed to room temperature over 18 hours. The reaction was transferred to a separatory funnel with EtOAc and a saturated solution of NH$_4$Cl was added. The organic layer was isolated, dried, concentrated, and chromatographed, providing 36.2 mg (22.9%) of the desired dithiane along with 25.9 mg (19.7%) starting material. $^1$H NMR (CDCl$_3$) 11.55 (br s, 1H), 8.56 (br d, J=6.1 Hz, 1H), 7.40-7.26 (m, 10H), 5.34 (br d, J=7.6 Hz, 1H), 5.17 (s, 2H), 5.12 (s, 2H), 4.36-4.22 (m, 1H), 4.03-3.89 (m, 1H), 3.41-3.27 (m, 1H), 3.12 (dd, J=15.5, 7.0 Hz, 1H), 2.95-2.80 (m, 2H), 2.78-2.68 (m, 2H), 2.68-2.51 (m, 2H), 2.29-2.17 (m, 2H), 2.16-2.07 (m, 3H), 1.71 (s, 3H), 1.66-1.53 (m, 1H).

The dithiane intermediate (36.2 mg, 59.5 μmol, 1 equiv) was stirred in methanolic HCl (1 M; 892 μL, 891 μmol, 15 equiv) at 0° C. for 4 hours. The reaction was then diluted with excess MeOH and concentrated under reduced pressure. The crude material was purified by column chromatography to afford 7.9 mg (24.1%) of the desired Cbz-protected guanidino ester. $^1$H NMR (CDCl$_3$) 11.49 (br s, 1H), 8.47 (br d, J=5.9 Hz, 1H), 7.36-7.21 (m, 10H), 5.28 (br d, J=7.3 Hz, 1H), 5.12 (d, J=4.7 Hz, 2H), 5.07 (s, 2H), 4.36-4.22 (m, 1H), 3.86-3.70 (m, 1H), 3.60 (s, 3H), 2.84-2.74 (m, 1H), 2.61-2.43 (m, 2H), 2.33-2.23 (m, 1H), 2.18-1.99 (m, 2H), 1.84-1.70 (m, 1H), 1.60 (s, 3H), 1.53-1.38 (m, 2H).

The Cbz-protected intermediate (7.9 mg, 14.7 μmol, 1 equiv) was dissolved in MeOH (2 mL) and Pd/C (10 wt %; 15.7 mg, 14.7 μmol, 1 equiv) was added after the atmosphere had been purged with H$_2$ gas. The resulting solution was then stirred under an atmosphere of H$_2$ gas for 48 hrs. Pd/C was subsequently filtered and the resulting solution was concentrated to provide 0.4 mg of 45. HRMS (ESI) calcd for C$_{13}$H$_{22}$N$_4$O$_3$+H$^+$ 283.17646. found 283.17629.

Enzyme Assays:

Virus propagation: Influenza A/Brisbane/59/2007 (H1N1) virus was propagated in Madin-Darby Canine Kidney (MDCK) cells. Seed virus was inoculated into 10 confluent 75 cm$^2$ monolayers which were incubated at 37° C. for 2-3 days and harvested when full cytopathic effect was observed. Virus purification: The pooled cell lysates were frozen and thawed and clarified by centrifugation at 3000 g for 20 mM. The supernatant was subjected to ultracentrifugation at 25,000 rpm for 90 min and the virus containing pellet was resuspended in 2 mL of MegaVir medium (Hyclone). Virus concentration was assessed by hemagglutination (HA) at 40,960 HA units. Virus inactivation: NP40 (Fluka) was added to the purified influenza virus at a final concentration of 0.2% and the mixture was incubated at room temperature for a total of 3 hours and at 4° C. for 6 h. The inactivation of the virus was confirmed by the Tissue Culture Infectious Dose assay. This virus preparation had a titre of 10$^7$ TCID$_{50}$ per 100 μL before inactivation and <10$^2$ TCID$_{50}$ per 100 μL after NP40 treatment.

The following solutions were prepared for the enzyme assays: (1) Assay buffer: 50 mM Tris, 5 mM CaCl$_2$, 200 mM NaCl, pH 7.5; (2) Protein stock solution: recombinant neuraminidase was diluted in assay buffer to 1000 ng/mL, or inactivated virus suspension was diluted to obtain a similar activity; (3) Substrate stock solution: 2'-4(methylumbelliferyl)-α-D-N-acetylneuraminic acid (Aldrich) was dissolved in DMSO to a concentration of 10 mM; (4) Substrate working solution: 40 μL of the substrate stock solution was diluted to 1000 μL with assay buffer, for a final concentration of 400 μM (4% DMSO); (5) Inhibitor solutions: Inhibitors were diluted in assay buffer to provide a range of working concentrations. For IC$_{50}$ measurements with recombinant neuraminidase, sample wells of a black 96-well plate (Nunc, optical bottom) were charged with 40 μL of protein stock solution (1000 ng/mL), followed by 10 μL of inhibitor solution and 50 μL of substrate working solution (400 μM substrate, 4% DMSO). The samples (each containing 100 μL total volume, 400 ng/mL enzyme, 200 μM substrate, and 1.5% total DMSO, in 100 μL total sample volume) were mixed briefly by pipetting. Fluorescence was monitored over 5 min ($\lambda_{exc}$=365 nm; $\lambda_{em}$=445 nm). Experiments with inactivated virus were conducted similarly, except that the inhibitor solutions were added to wells containing inactivated virus, and these mixtures were allowed to incubate for either 10 mM or 2 h at room temperature prior to the addition of working solution. For kinetic data, the working solution was subjected to serial dilution in assay buffer containing 4% DMSO. Progress of the reaction was measured over 10 min at various concentrations of substrate and inhibitor. Control experiments (substrate buffer only) showed no significant background reaction. Data was plotted using XLfit (IDBS software).

Figure 5:
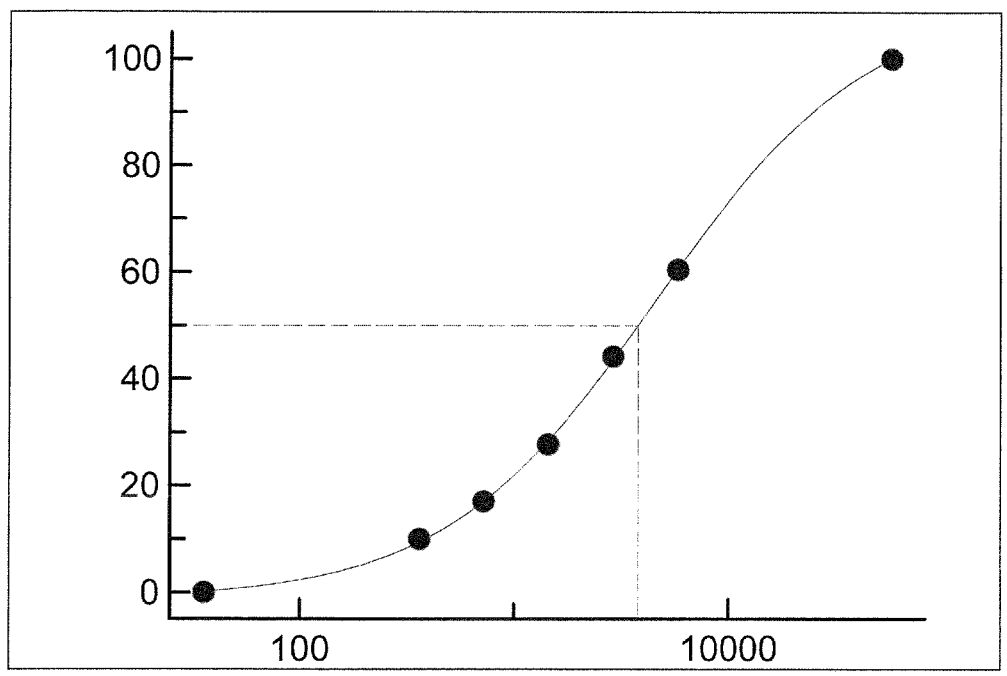
FIG. 5 is a graph illustrating the $IC_{50}$ value (3.7 mM) for compound 27 of Example 16.
Figure 6:
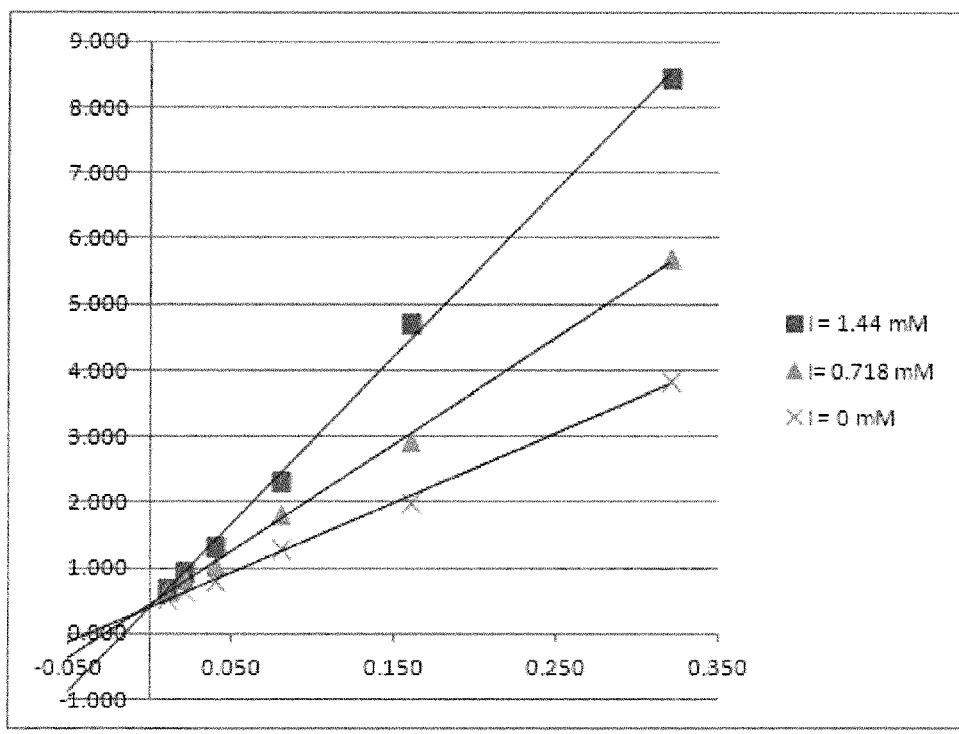
FIG. 6 is a Lineweaver-Burk plot obtained from analysis of compound 27 of Example 16.
Figure 7:
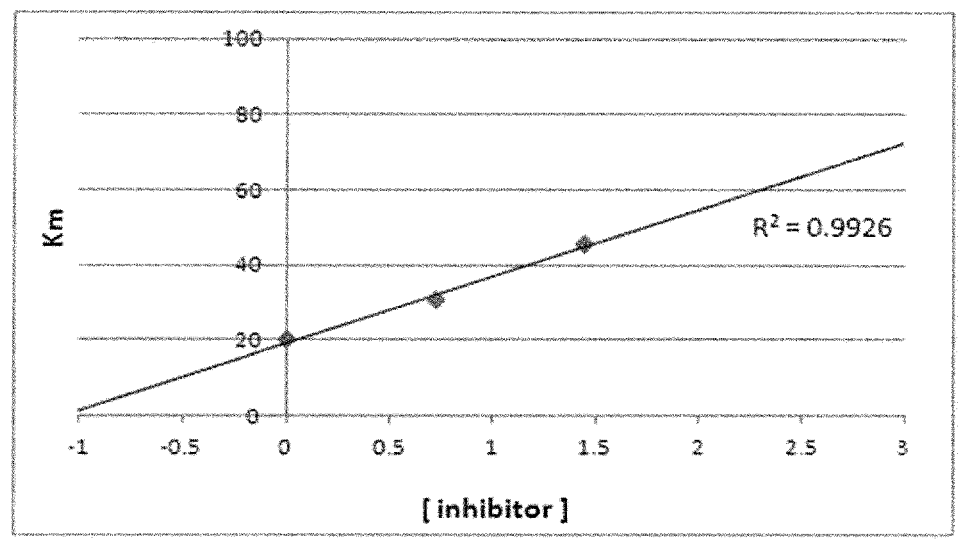
FIG. 7 is a graph ($K_m$ versus inhibitor concentration in mM) illustrating the estimated K, for compound 27 of Example 16.
Figure 8:
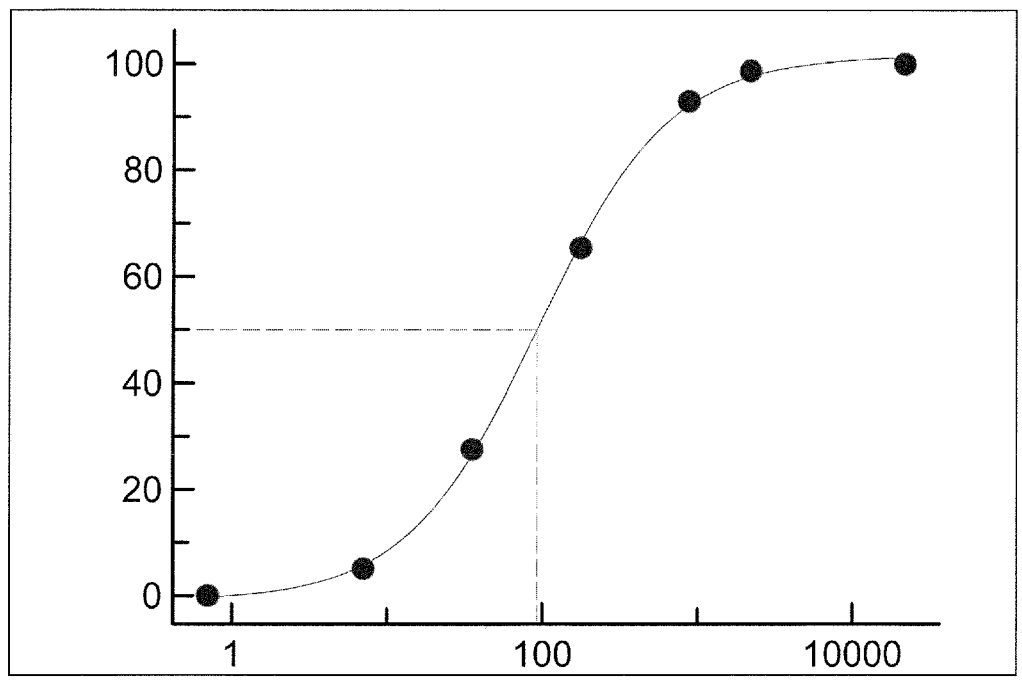
FIG. 8 is a graph illustrating the $IC_{50}$ value (92 µM) for amino acid 31 of Example 20.
Figure 9:
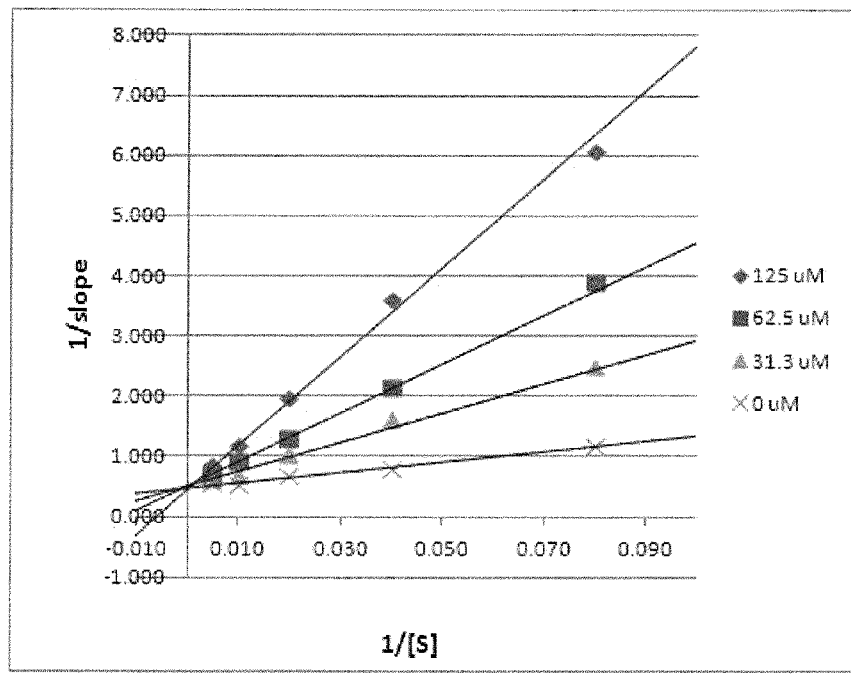
FIG. 9 is a Lineweaver-Burk plot obtained from analysis of amino acid 31 of Example 20.
Figure 10:
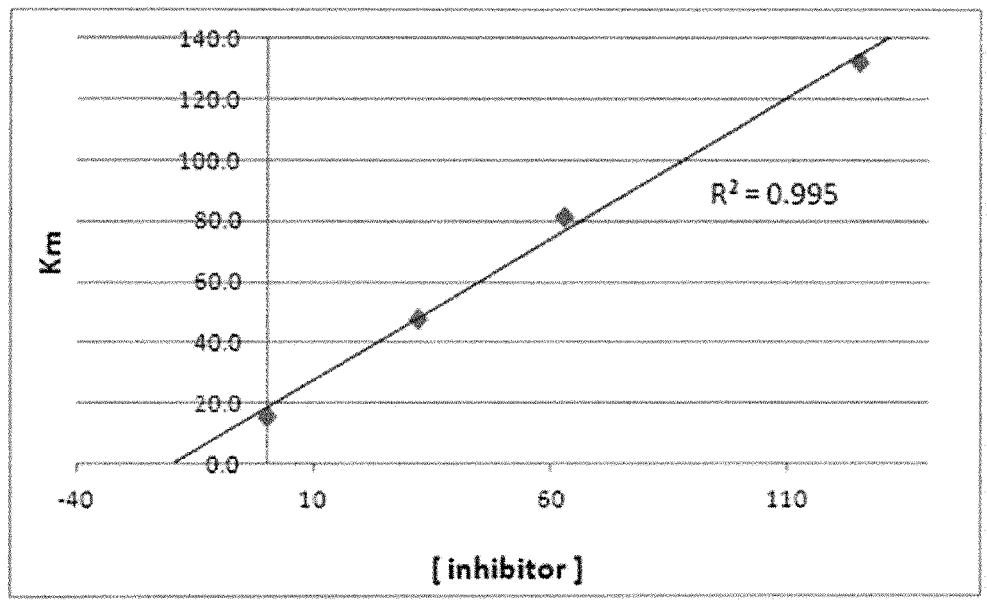
FIG. 10 is a graph ($K_m$ versus inhibitor concentration in µM) illustrating the estimated K, for amino acid 31 of Example 20.
Figure 11:
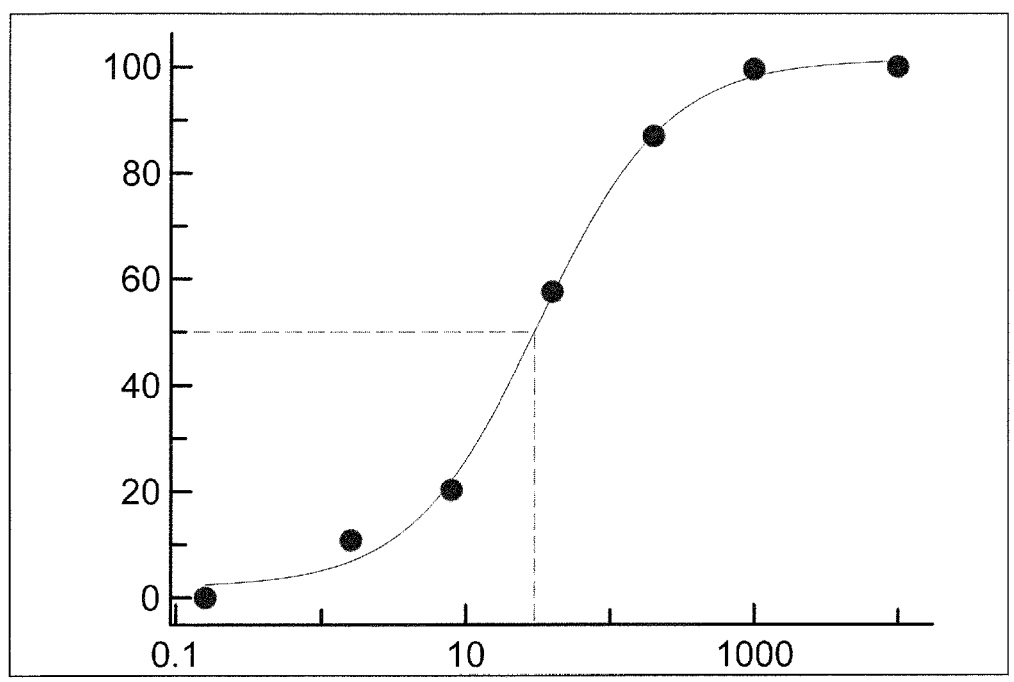
FIG. 11 is a graph illustrating the $IC_{50}$ value (30 µM) for guanidino acid 32 of Example 21.
Figure 12:
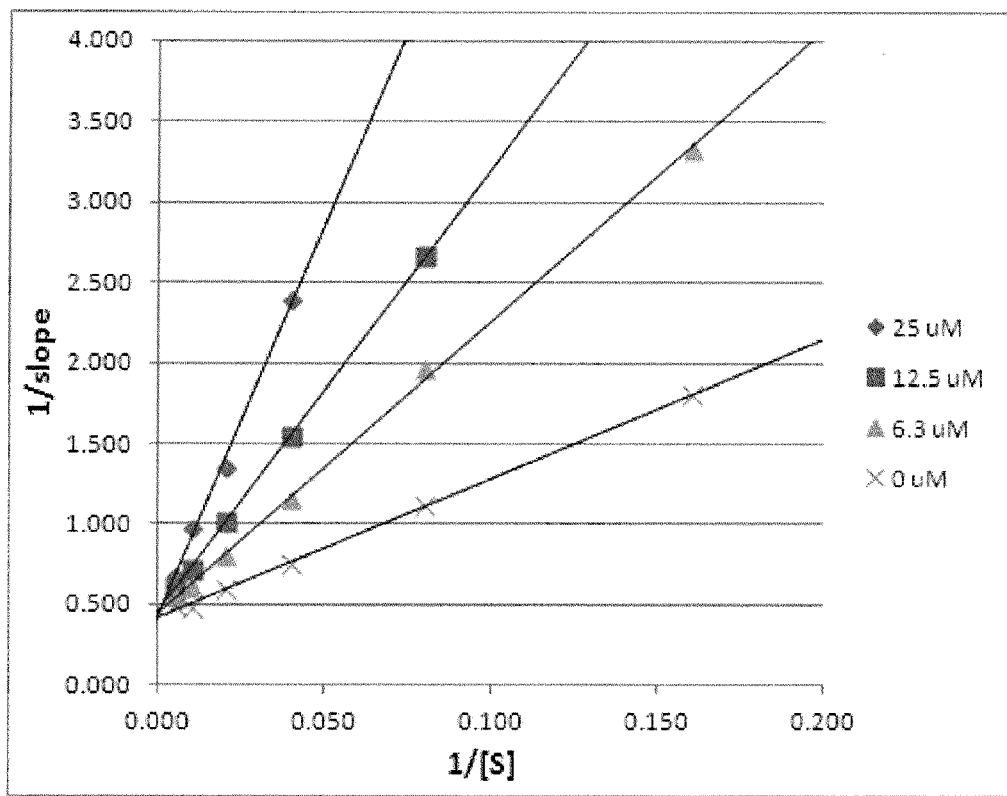
FIG. 12 is a Lineweaver-Burk plot obtained from analysis of guanidino acid 32 of Example 21.
Figure 13:
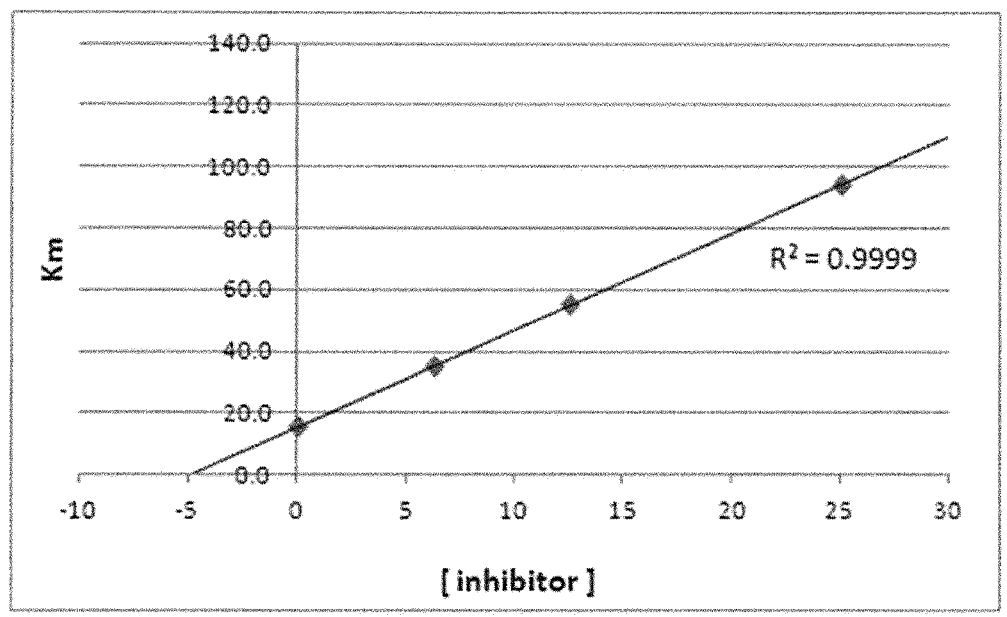
FIG. 13 is a graph ($K_m$ versus inhibitor concentration in µM) illustrating the estimated $K_i$ for guanidino acid 32 of Example 21.

The disclosed compounds are effective inhibitors of influenza neuraminidase. TABLE 1 summarizes enzyme inhibition data for representative compounds against influenza neuraminidase. FIGS. 5-7 illustrate the results obtained from analyzing Compound 27. In particular, FIG. 5 provides graphical analysis of the $IC_{50}$ data obtained for Compound 27. FIGS. 6 and 7 illustrate the Lineweaver-Burk plot and Michaelis-Menton analysis for Compound 27. FIGS. 8-10 illustrate the results obtained from Compound 31 ($IC_{50}$ graph (FIG. 8), Lineweaver-Burk plot (FIG. 9), and Michaelis-Menton analysis (FIG. 10)). FIGS. 11-13 illustrate the results obtained from Compound 32 ($IC_{50}$ graph (FIG. 11), Lineweaver-Burk plot (FIG. 12), and Michaelis-Menton analysis (FIG. 13)).

TABLE 1

Inhibition of Influenza Neuraminidase

| Inhibitor | $IC_{50}$ | $K_i$ | Inhibition Mode |
|---|---|---|---|
| Compound 20 | 4.0 mM[a] | n.d. | mixed |
| Compound 21 | >10 mM[a] | n.d. | n.d. |
| Compound 27 | 3.8 mM[b] | 1 mM | competitive |
| Compound 31 | 92 μM[b] | 20 μM | competitive |
| Compound 32 | 30 μM[b] | 5 μM | competitive |

[a] In vitro assay vs. recombinant H1N1 neuraminidase protein purchased from R&D systems;
[b] In vitro neuraminidase assay vs. NP40-inactivated influenza A/Brisbane/59/2007(H1N1).

In one embodiment, the compound has a formula

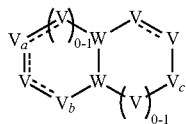

where V, $V_a$, $V_b$, and $V_c$ are selected from $CR^{11}R^{12}$, $C(R^{11})_2$, $CR^{12}R^{13}$, $C(R^{13})_2$, $SO_2$, SO, S, O, $NR^{11}$, CO, and Se;

W is nitrogen, $CR^{10}$, or $CR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof;

if $V_a$ comprises $CR^{11}R^{12}$, $C(R^{11})_2$, $CR^{12}R^{13}$, or $C(R^{13})_2$, then $V_a$ and $V_b$ together) can comprise a lactone or a lactam;

if $V_c$ comprises $CR^{11}R^{12}$, $C(R^{11})_2$, $CR^{12}R^{13}$, or $C(R^{13})_2$ and has at least two substituents selected from $R^{11}$, $R^{12}$, or $R^{13}$, or any combination thereof, then the two substituents together can form a cyclic alkyl group;

n=0, 1 or 2; and m=0, 1 or 2.

In one embodiment, the heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfonyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidine.

In one embodiment, the compound is selected from any one of

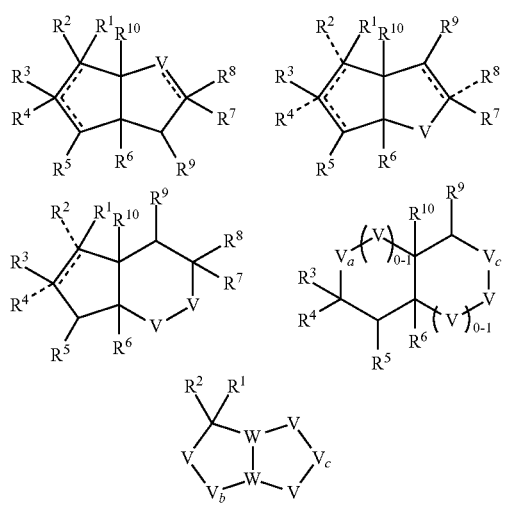

where V, $V_a$, $V_b$, and $V_c$ are selected from $CR^{11}R^{12}$, $C(R^{11})_2$, $C(R^{13})_2$, $SO_2$, SO, S, O, $NR^{11}$, CO, and Se;

W is selected from $CR^{10}$, $CR^{11}$, nitrogen, and any combination thereof;

$R^1$ is selected from $CO_2H$, $(CH_2)CO_2H$, $(CH_2)OH$, tetrazolyl, $SO_2H$, $SO_3H$, $PO_3H_2$, esters, amides, anhydrides and other protected forms thereof;

$R^2$ is selected from H, OH, $(CH_2)_nZH$, where Z is selected from O, S, Se, $NR^{11}$, or $R^1$ and $R^2$ together represent =O;

$R^3$ and $R^4$ independently are selected from hydrogen, alkyl, branched alkyl, aryl, heteroaryl, or $R^3$ and $R^4$ together may represent a cyclic alkyl group or =O;

$R^5$ is selected from $NH_2$, $(CH_2)N(R^{11})_m(H)_{(2-m)}$, $(CH_2)NHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is selected from O, S, Se, and $NR^{11}$; guanidino, substituted guanidino, alkyl, branched alkyl, cyclic alkyl, alkenyl, alkynyl, aryl, heteroaryl, or $R^5$ and $R^1$ together form a lactam or lactone;

$R^6$ is H, alkyl and $(CH_2)_nOH$;

$R^7$ and $R^8$ independently are selected from H, alkyl, branched alkyl, cyclic alkyl, aryl, heteroaryl, $(CH_2)_nY$, $(CH_2)_n$ ZY, $(CH_2)_nCR^{11}Z$, $(CH_2)_2ZH$, $[CH_2]_n[CH(ZH)]_m CH_2ZH$, $[CH_2][CH(ZH)]_mCH_2Y$, where Y is selected from aryl, heteroaryl, alkyl, cyclic alkyl, heterocyclic, amino and guanidino, and Z is selected from O, S, Se, or $NR^{11}$, or $R^7$ and $R^8$ together represent a cyclic alkyl group; and $R^9$ is selected from H, alkyl, branched alkyl, cyclic alkyl, alkenyl, alkynyl, aryl, heteroaryl, $O(R^{11})_m$, $S(R^{11})_m$, $N(R^{11})_m (H)_{(2-m)}$, $(CH_2)_nZH$, $(CH_2)ZR^{11}$, $(CH_2)Z(CO)R^{11}$, $(CH_2)_nZ(SO_2)R^{11}$, $(CH_2)_nZ(CO)NH_2$, $(CH_2)_nZ(CO)OR^{11}$, or $(CH_2)_n Z(CNH)NH_2$, and Z=O, S, Se, or $NR^{11}$.

In one embodiment, $V_a$ is $CR^{11}R^{12}$, $C(R^{11})_2$, or $C(R^{13})_2$, and any one of $R^{11}$, $R^{12}$, or $R^{13}$ together with $R^5$ form a lactam or lactone.

In one embodiment, $V_c$ is $CR^{11}R^{12}$, $C(R^{11})_2$, $C(R^{13})_2$, and any one of $R^{11}$, $R^{12}$, or $R^{13}$ together form a cyclic alkyl.

In one embodiment, $V_b$ is $CR^{11}R^{12}$, $C(R^{11})_2$, or $C(R^{13})_2$, and any one of $R^{11}$, $R^{12}$, or $R^{13}$ together with $R^1$ form a lactam or lactone.

In one embodiment, the compound is formulated as a pharmaceutically acceptable salt, prodrug, solvate, or hydrate.

In one embodiment, the compound is selected from any one of

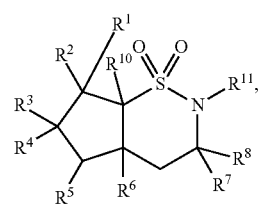 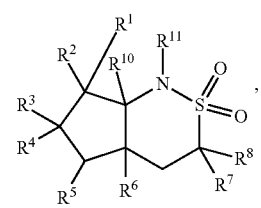

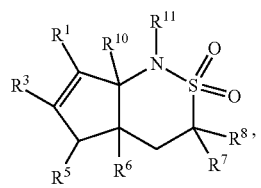 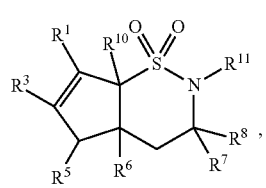

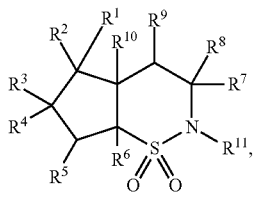 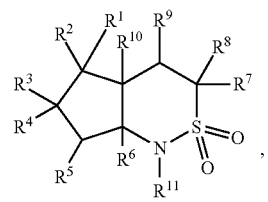

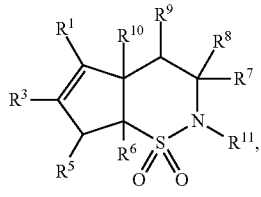 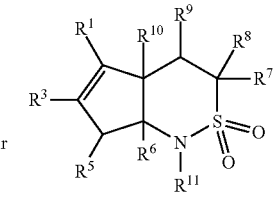

In one embodiment, the compound has any one of the following formulas

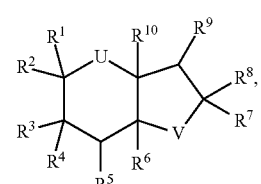 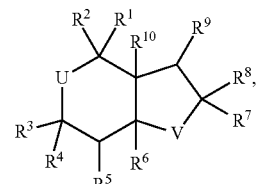

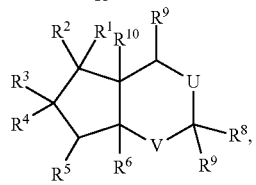 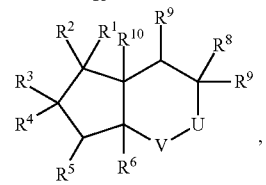

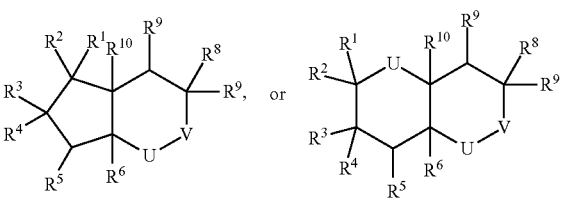

where U is selected from O, $NR^{11}$, $CHR^{11}$, or S.

In one embodiment, the compound has any one of the following

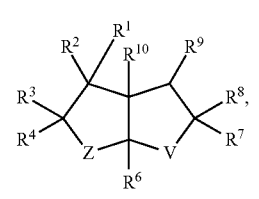 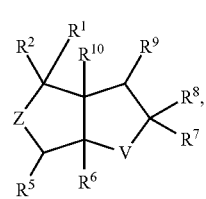

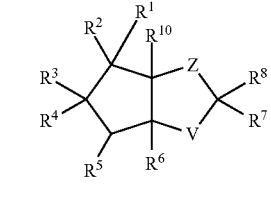 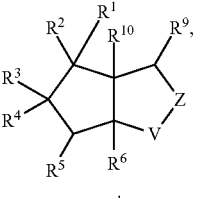

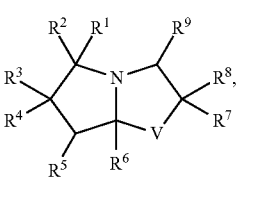 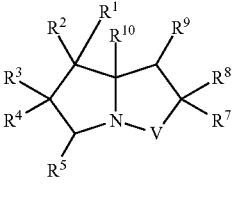

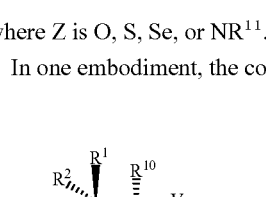 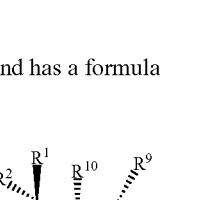

where Z is O, S, Se, or $NR^{11}$.

In one embodiment, the compound has a formula

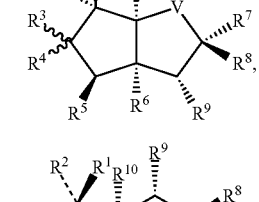 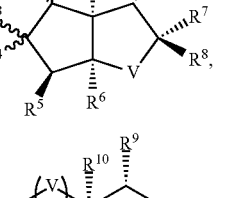

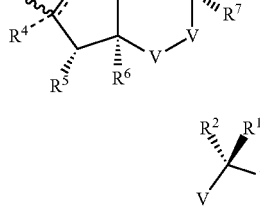 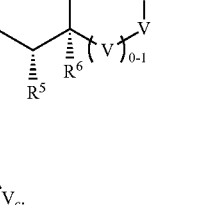

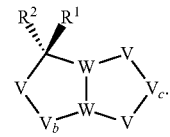

In one embodiment, the compound is
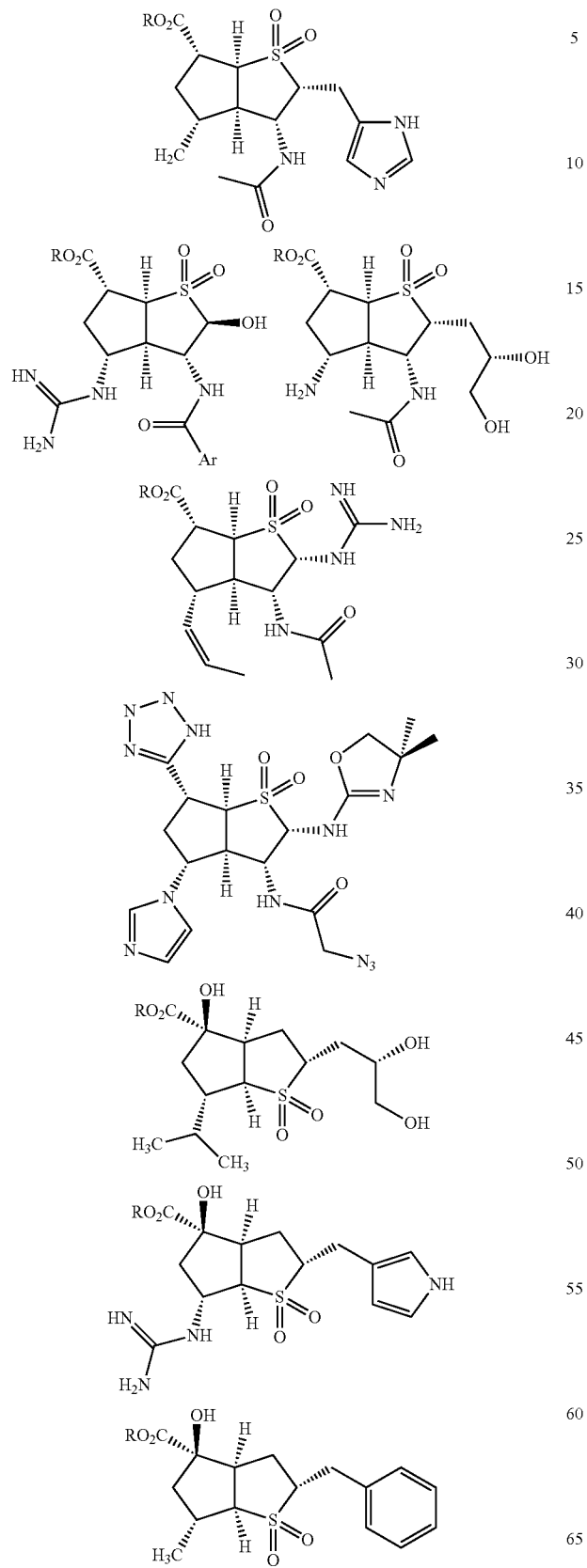
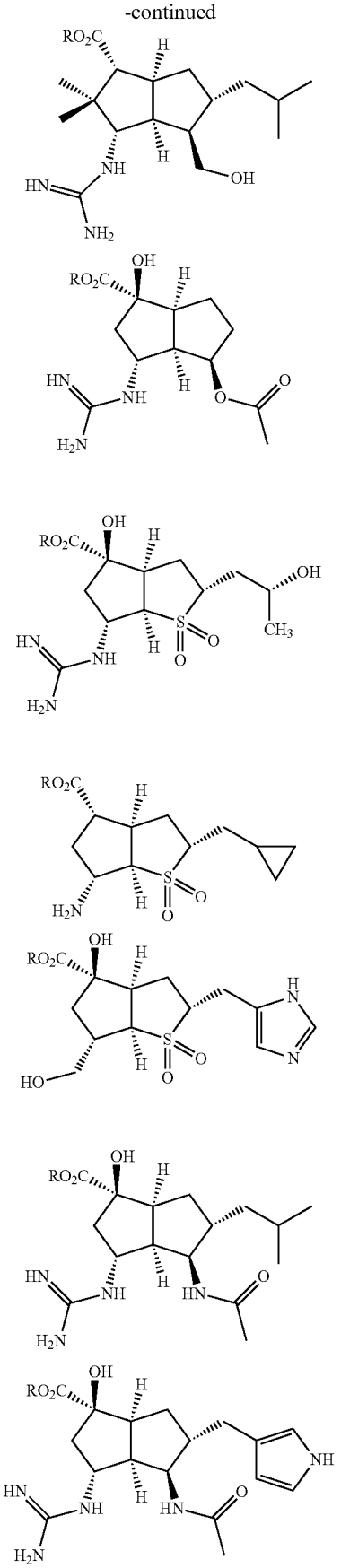

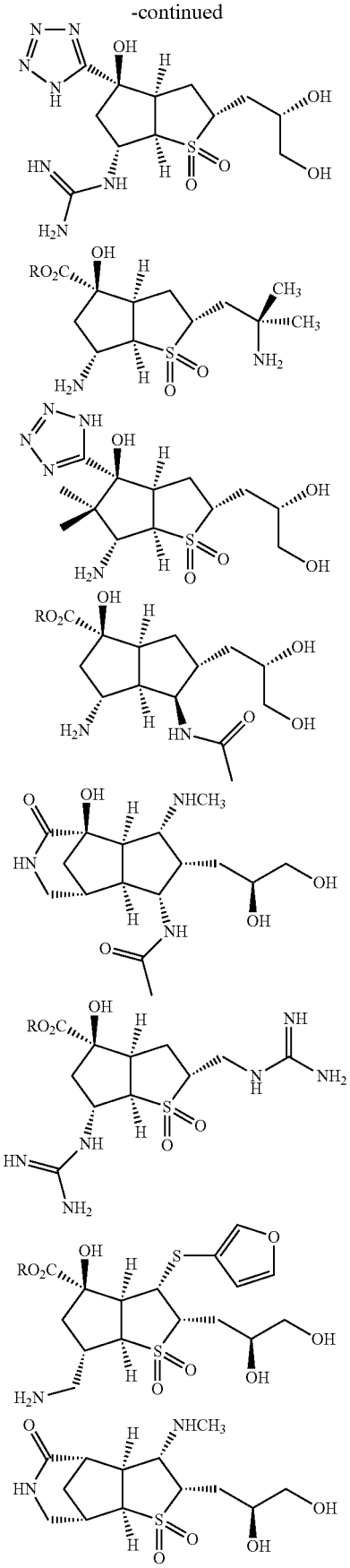
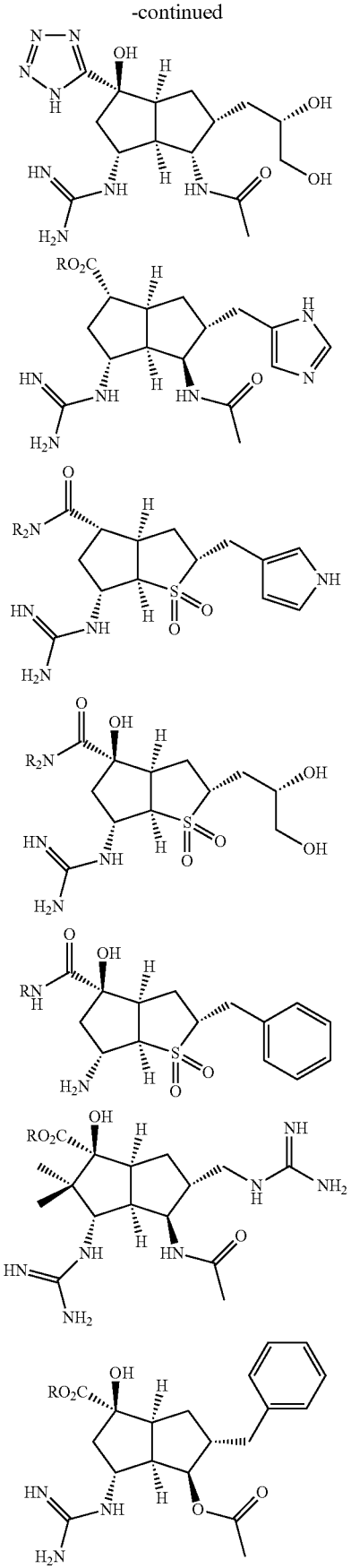

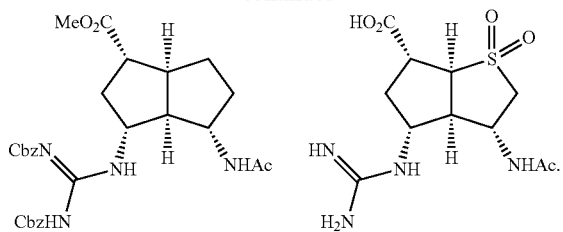

where R is selected from H, alkyl, aryl, heteroaryl, or acyl; and Ar is aryl or heteroaryl.

Particular embodiments concern a composition, comprising one or more compounds having a formula

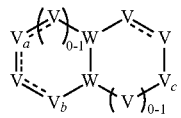

where V, $V_a$, $V_b$, and $V_c$ are selected from $CR^{11}R^{12}$, $C(R^{11})_2$, $CR^{12}R^{13}$, $C(R^{13})_2$, $SO_2$, SO, S, O, $NR^{11}$, CO, and Se;

W is nitrogen, $CR^{10}$, or $CR^{11}$;

$R^{10}$ is H, alkyl or $(CH_2)OH$;

$R^{11}$ is H, alkyl, branched alkyl, cyclic alkyl, aryl, heteroaryl, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof;

if $V_a$ comprises $CR^{11}R^{12}$, $C(R^{11})_2$, $CR^{12}R^{13}$, or $C(R^{13})_2$, then $V_a$ and $V_b$ together can comprise a lactone or a lactam;

if $V_e$ comprises $CR^{11}R^{12}$, $C(R^{11})_2$, $CR^{12}R^{13}$, or $C(R^{13})_2$ and has at least two substituents selected from $R^{11}$, $R^{12}$, or $R^{13}$, or any combination thereof, then the two substituents together can form a cyclic alkyl group;

n=0, 1 or 2;

m=0, 1 or 2; and at least one biologically acceptable material.

In one embodiment, compound has a formula

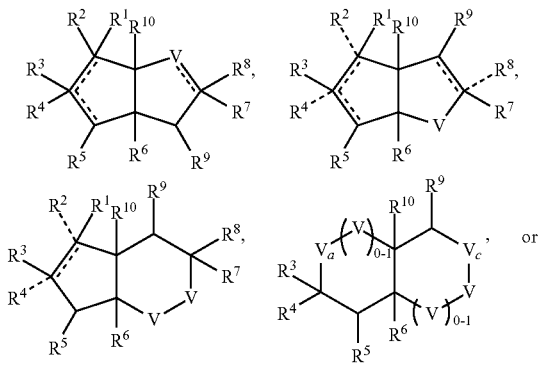

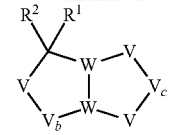

where V, $V_a$, $V_b$, and $V_c$ are selected from $CR^{11}R^{12}$, $C(R^{11})_2$, $C(R^{13})_2$, $SO_2$, SO, S, O, $NR^{11}$, CO, and Se;

W is selected from $CR^{19}$, $CR^{11}$, nitrogen, and any combination thereof;

$R^1$ is selected from $CO_2H$, $(CH_2)_nCO_2H$, $(CH_2)_nOH$, tetrazolyl, $SO_2H$, $SO_3H$, $PO_3H_2$, esters, amides, anhydrides and other protected forms thereof;

$R^2$ is selected from H, OH, $(CH_2)_nZH$, where Z is selected from O, S, Se, $NR^{11}$, or $R^1$ and $R^2$ together represent =O;

$R^3$ and $R^4$ independently are selected from hydrogen, alkyl, branched alkyl, aryl, heteroaryl, or $R^3$ and $R^4$ together may represent a cyclic alkyl group or =O;

$R^5$ is selected from $NH_2$, $(CH_2)N(R^{11})_m(H)_{(2-m)}$, $(CH_2)_n NHC(O)(R^{11})$, $(CH_2)_nNC(=NR^{11})N(R^{11})_m(H)_{(2-m)}$, $(CH_2)_n NHC(O)Z(R^{11})$, $(CH_2)_nZH$, where Z is selected from O, S, Se, and $NR^{11}$; guanidino, substituted guanidino, alkyl, branched alkyl, cyclic alkyl, alkenyl, alkynyl, aryl, heteroaryl, or $R^5$ and $R^1$ together form a lactam or lactone;

$R^6$ is H, alkyl and $(CH_2)_nOH$;

$R^7$ and $R^8$ independently are selected from H, alkyl, branched alkyl, cyclic alkyl, aryl, heteroaryl, $(CH_2)_nY$, $(CH_2)_n$ ZY, $(CH_2)_nCR^{11}Z$, $(CH_2)_2ZH$, $[CH_2]_n[CH(ZH)]_n CH_2ZH$, $[CH_2]_n[CH(ZH)]_mCH_2Y$, where Y is selected from aryl, heteroaryl, alkyl, cyclic alkyl, heterocyclic, amino and guanidino, and Z is selected from O, S, Se, or $NR^{11}$, or $R^7$ and $R^8$ together represent a cyclic alkyl group; and $R^9$ is selected from H, alkyl, branched alkyl, cyclic alkyl, alkenyl, alkynyl, aryl, heteroaryl, $O(R^{11})_m$, $S(R^{11})_m$, $N(R^{11})_m (H)_{(2-m)}$, $(CH_2)_nZH$, $(CH_2)_nZR^{11}$, $(CH_2)_nZ(CO)R^{11}$, $(CH_2)_n Z(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$.

In one embodiment, the compound has a formula

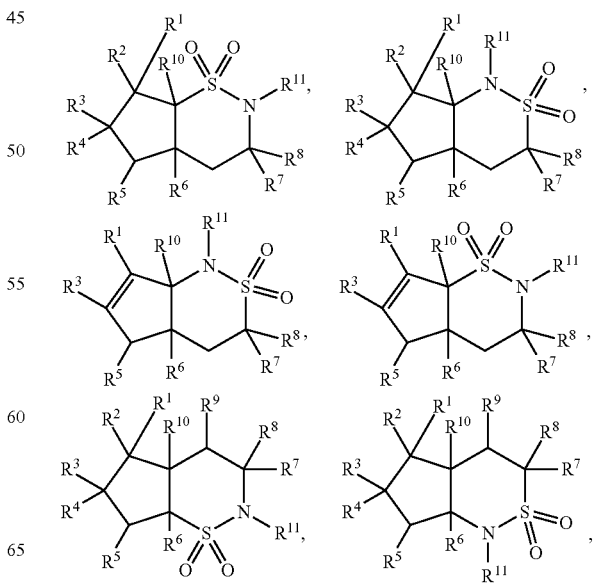

-continued
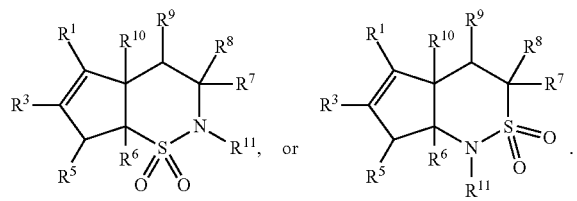
In one embodiment, the compound has a formula
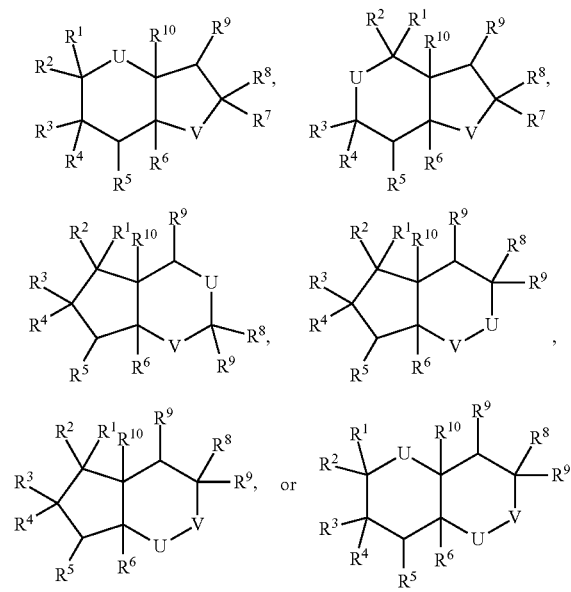
where U is selected from O, NR$^{11}$, CHR$^{11}$, or S.
In one embodiment, the compound has a formula
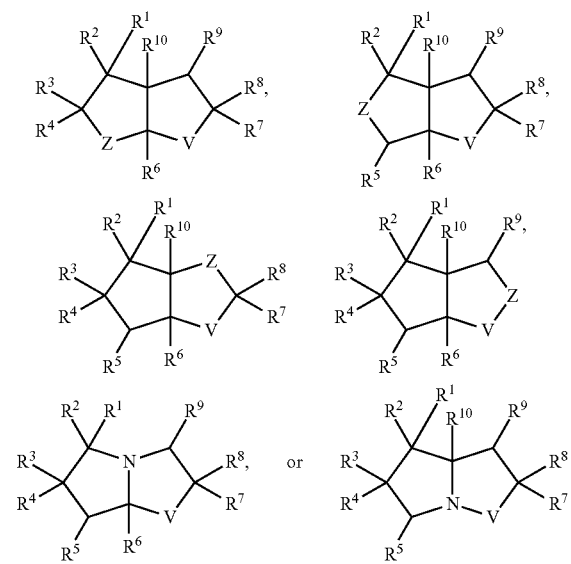
where Z is O, S, Se, or NR$^{11}$.
In one embodiment, the compound has a formula
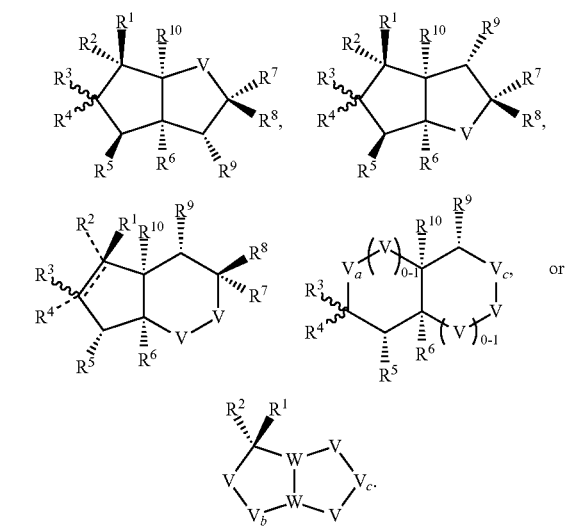
In one embodiment, the compound is
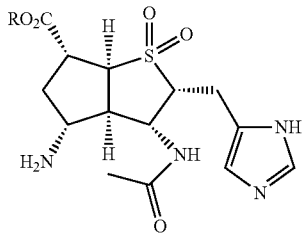
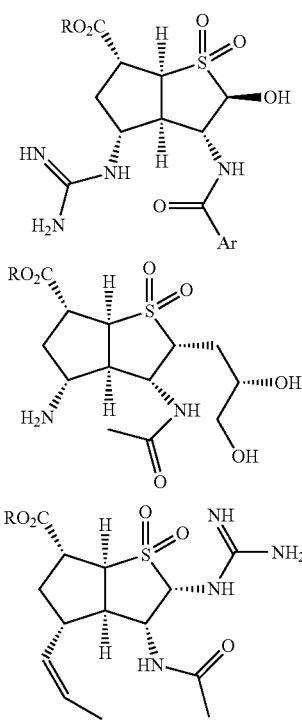

75
-continued
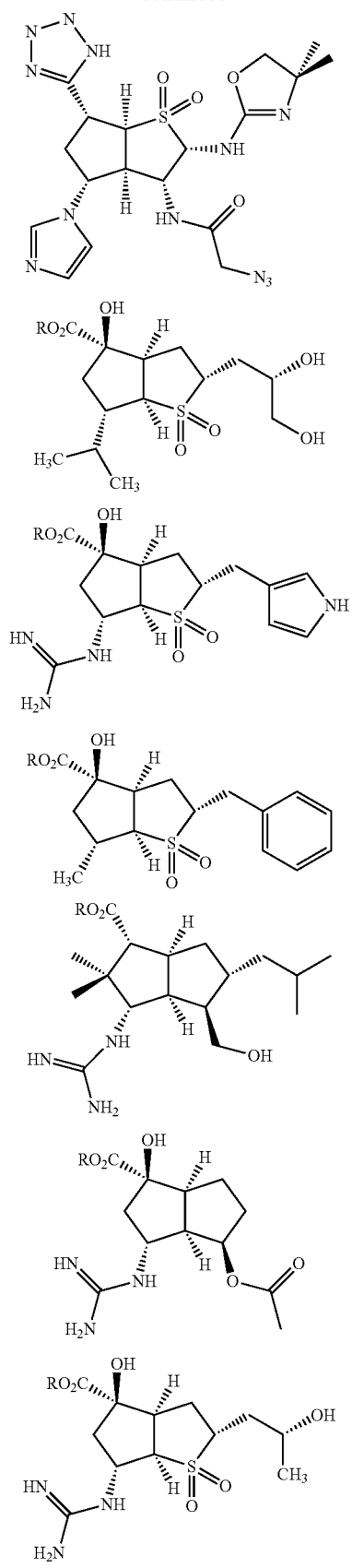
76
-continued
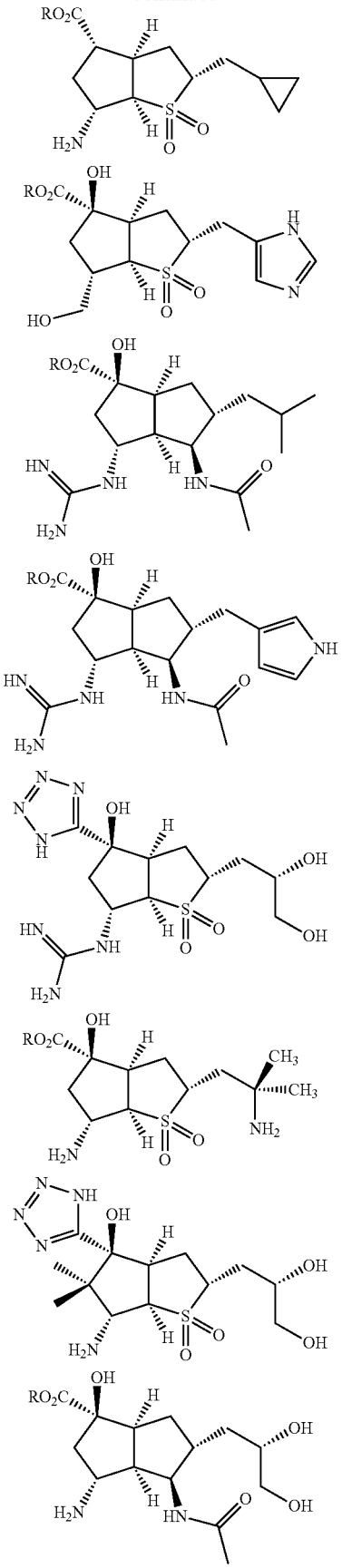

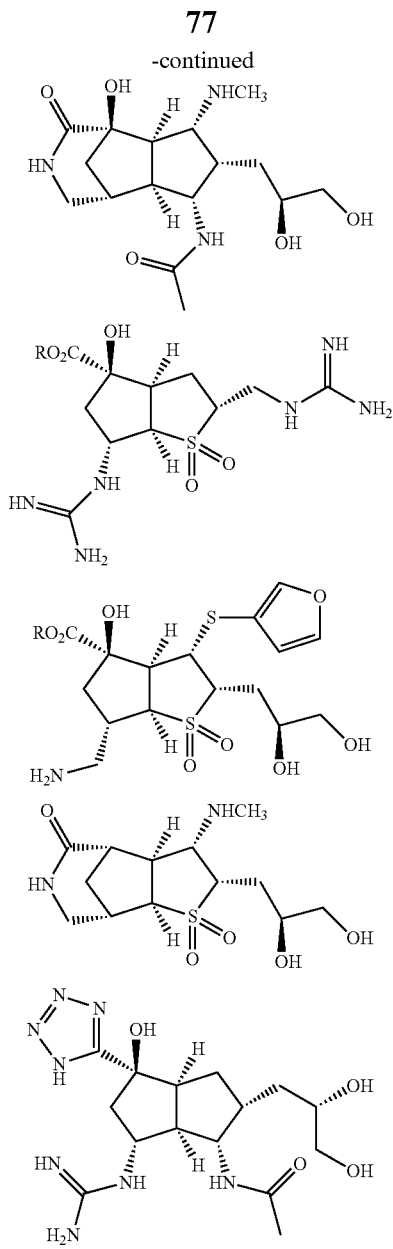
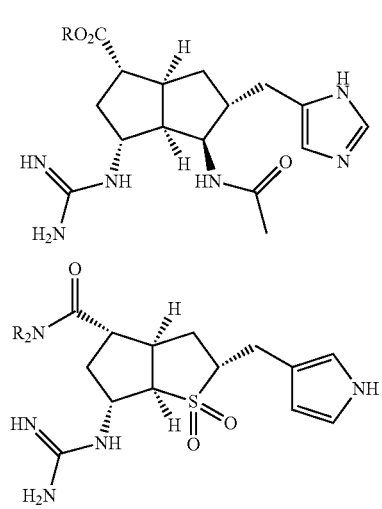
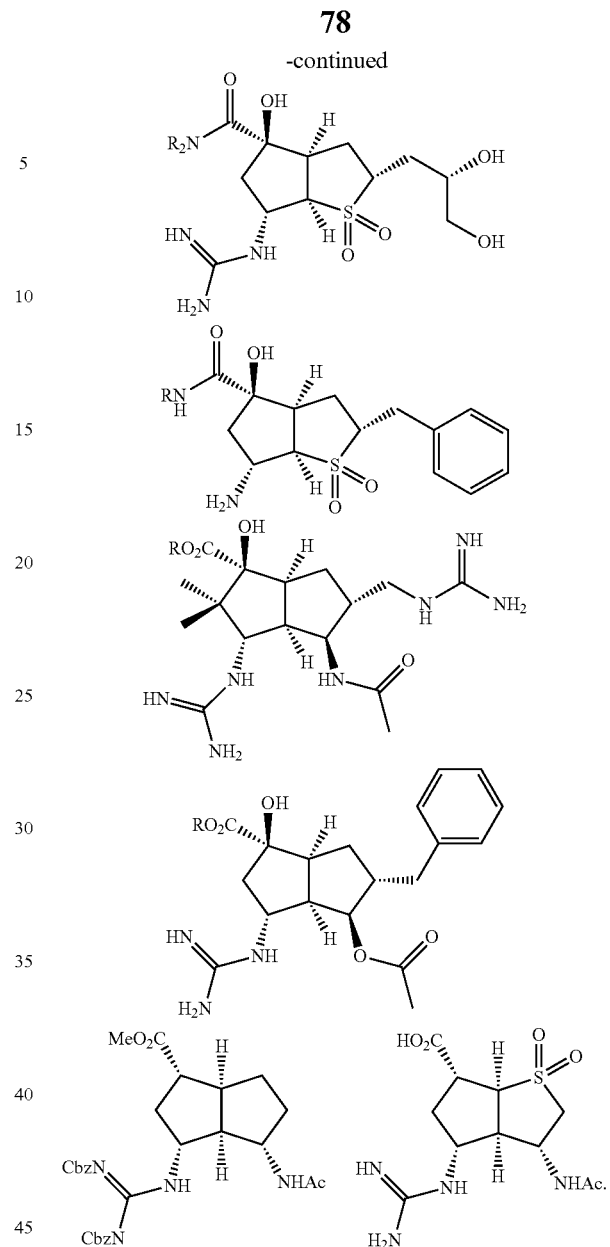

where R is selected from H, alkyl, aryl, heteroaryl, or acyl; and Ar is aryl or heteroaryl.

In one embodiment, the least one biologically acceptable material is selected from carriers, diluents, adjuvants, excipients, binders, fillers, lubricants, osmotic agents, flavoring agents, other active ingredients, and combinations thereof.

In one embodiment, the at least one biologically acceptable material is selected from solvents; saline; buffered saline; dextrose; water; glycerol; ethanol; propylene glycol; polysorbate 80 (Tween-80™); poly(ethylene)glycol 300 and 400 (PEG 300 and 400); PEGylated castor oil (e.g. Cremophor EL); poloxamer 407 and 188; hydrophobic carriers; fat emulsions; lipids; PEGylated phopholids; polymer matrices; biocompatible polymers; lipospheres; vesicles; particles; liposomes; stabilizing agents; solubilizing agents; surfactants; buffers; antioxidants; preservatives; tonicity agents; bulking agents; emulsifiers; suspending agents; viscosity agents; inert diluents; fillers; disintegrating agents; binding agents; wetting agents; lubricating agents; antibacterials; chelating agents; sweetners; perfuming agents; flavouring agents; coloring agents; administration aids; sodium carbonate; calcium carbonate; sodium phosphate; calcium phosphate; lactose; sodium chloride; glycerol; sorbitol; xylitol; glucose; acacia gum; starch; gelatin; sucrose; polyvinylpyrrolidone (Providone); sorbitol; tragacanth methylcellulose; sodium carboxymethylcellulose; hydroxypropyl methylcellulose; ethylcellulose; calcium phosphate; glycine; lactose; maize-starch; sorbitol; sucrose; magnesium stearate or other metallic stearates; stearic acid; polyethylene glycol; waxes; oils; silica and colloical silica; silicon fluid; talc; peppermint; oil of wintergreen; fruit flavoring; or combinations thereof.

Other embodiments concern a method for treating a subject, comprising, administering to a subject an effective amount of one or more compounds disclosed herein, or a composition comprising the compound; and In one embodiment, the subject is a human.

In one embodiment, the compound or composition is administered prophylactically.

In one embodiment, the effective amount is from greater than 0 to about 1000 mg/kg body weight per day.

In one embodiment, the effective amount is from greater than 0 to about 10 mg/kg body weight per day.

In one embodiment, the effective amount is from greater than 0 to about 5 mg/kg body weight per day.

In one embodiment, the effective amount is from greater than 0 to about 0.5 mg/kg body weight per day.

In one embodiment, the compound or composition is administered in single or multiple doses.

In one embodiment, administering comprises oral, rectal, nasal, topical (including buccal and sublingual), vaginal, parenteral (including subcutaneous, intramuscular, intravenous, intradermal, intrathecal and epidural) administration, or combinations thereof.

Other embodiments concern a conjugate, comprising a compound having a formula

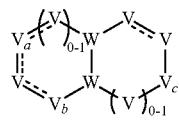

where V, $V_a$, $V_b$, and $V_c$ are $CR^{11}R^{12}$, $C(R^{11})_2$, $CR^{12}R^{13}$, $C(R^{13})_2$, $SO_2$, SO, S, O, $NR^{11}$, CO, and Se;

W is nitrogen, $CR^{10}$, or $CR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof;

if $V_a$ comprises $CR^{11}R^{12}$, $C(R^{11})_2$, $CR^{12}R^{13}$, or $C(R^{13})_2$, then $V_a$ and $V_b$ together can comprise a lactone or a lactam;

if $V_c$ comprises $CR^{11}R^{12}$, $C(R^{11})_2$, $CR^{12}R^{13}$, or $C(R^{13})_2$ and has at least two substituents selected from $R^{11}$, $R^{12}$, or $R^{13}$, or any combination thereof, then the two substituents together can form a cyclic alkyl group;

n=0, 1 or 2;

m=0, 1 or 2; and a specific binding moiety, a signal generating moiety, and combinations thereof.

In one embodiment, the heteroatom-containing moiety is selected from aldehyde, acyl halide, carbonate, carboxyl, carboxylate, ether, ester, hydroxyl, ketone, silyl ether, peroxy, hydroperoxy, phosphate, phosphonate, phosphoryl, phosphodiester, phosphine, pyrrole, thiol, thioether/sulfide, disulfide, sulfonyl, sulfonyl, carbonothioyl, sulfino, sulfo, thiocyanate, isothiocyanate, oxazole, oxadiazole, imidazole, triazole, tetrazole, amine, amide, azide, azo, cyano, isocyanate, imide, nitrile, isonitrile, nitro, nitroso, nitromethyl, selenol, guanidino, and substituted guanidino.

In one embodiment, the compound has a formula

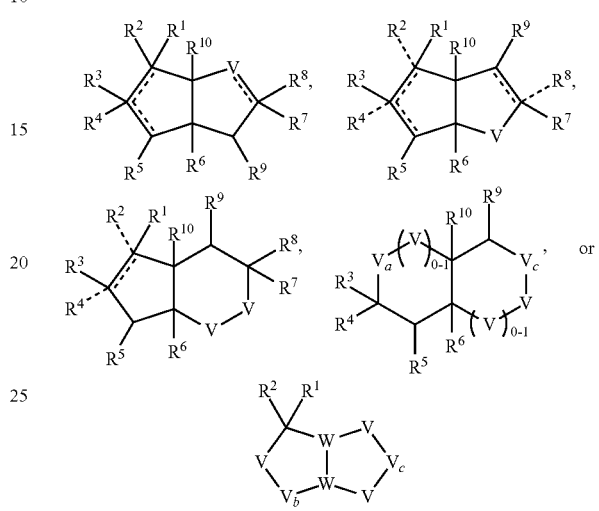

where V, $V_a$, $V_b$, and $V_c$ are selected from $CR^{11}R^{12}$, $C(R^{11})_2$, $C(R^{13})_2$, $SO_2$, SO, S, O, $NR^{11}$, CO, and Se;

W is selected from $CR^{10}$, $CR^{11}$, nitrogen, and any combination thereof;

$R^1$ is selected from $CO_2H$, $(CH_2)CO_2H$, $(CH_2)_nOH$, tetrazolyl, $SO_2H$, $SO_3H$, $PO_3H_2$, esters, amides, anhydrides and other protected forms thereof;

$R^2$ is selected from H, OH, $(CH_2)_nZH$, where Z is selected from O, S, Se, $NR^{11}$, or $R^1$ and $R^2$ together represent =O;

$R^3$ and $R^4$ independently are selected from hydrogen, alkyl, branched alkyl, aryl, heteroaryl, or $R^3$ and $R^4$ together may represent a cyclic alkyl group or =O;

$R^5$ is selected from $NH_2$, $(CH_2)_nN(R^{11})_m(H)_{(2-m)}$, $(CH_2)NHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is selected from O, S, Se, and $NR^{11}$; guanidino, substituted guanidino, alkyl, branched alkyl, cyclic alkyl, alkenyl, alkynyl, aryl, heteroaryl, or $R^5$ and $R^1$ together form a lactam or lactone;

$R^6$ is H, alkyl and $(CH_2)_nOH$;

$R^7$ and $R^8$ independently are selected from H, alkyl, branched alkyl, cyclic alkyl, aryl, heteroaryl, (CHAN, $(CH_2)_nZY$, $(CH_2)_nCR^{11}Z$, $(CH_2)_2ZH$, $[CH_2]_n[CH(ZH)]_mCH_2ZH$, $[CH_2]_n[CH(ZH)]_mCH_2Y$, where Y is selected from aryl, heteroaryl, alkyl, cyclic alkyl, heterocyclic, amino and guanidino, and Z is selected from O, S, Se, or $NR^{11}$, or $R^7$ and $R^8$ together represent a cyclic alkyl group; and $R^9$ is selected from H, alkyl, branched alkyl, cyclic alkyl, alkenyl, alkynyl, aryl, heteroaryl, $O(R^{11})$ $S(R^{11})_m$, $(K)_m$ $(H)_{(2-m)}$, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$.

In one embodiment, $V_a$ is $CR^{11}R^{12}$, $C(R^{11})_2$, or $C(R^{13})_2$, and any one of $R^{11}$, $R^{12}$, or $R^{13}$ together with $R^5$ form a lactam or lactone.

In one embodiment, $V_c$ is $CR^{11}R^{12}$, $C(R^{11})_2$, $C(R^{13})_2$, and any one of $R^{11}$, $R^{12}$, or $R^{13}$ together form a cyclic alkyl.

In one embodiment, $V_b$ is $CR^{11}R^{12}$, $C(R^{11})_2$, or $C(R^{13})_2$, and any one of $R^{11}$, $R^{12}$, or $R^{13}$ together with $R^1$ form a lactam or lactone.

In one embodiment, the compound is formulated as a pharmaceutically acceptable salt, prodrug, hydrate, or solvate.

In one embodiment, the compound has a formula

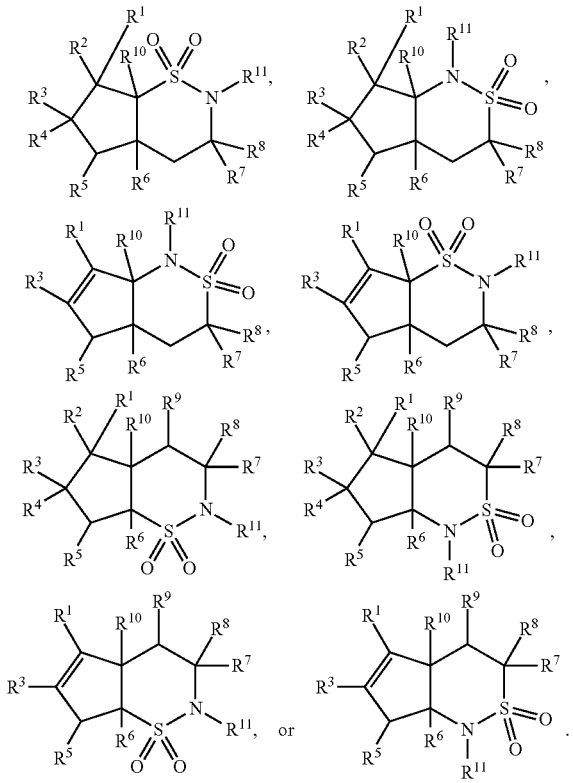

In one embodiment, the compound has a formula

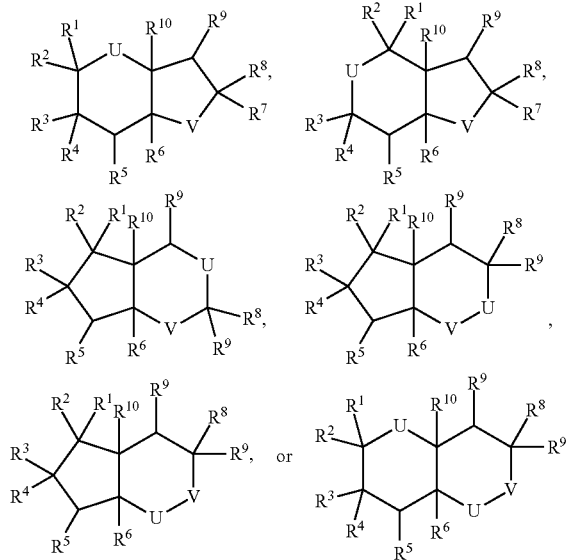

where U is selected from O, $NR^{11}$, $CHR^{11}$, or S.

In one embodiment, the compound has a formula

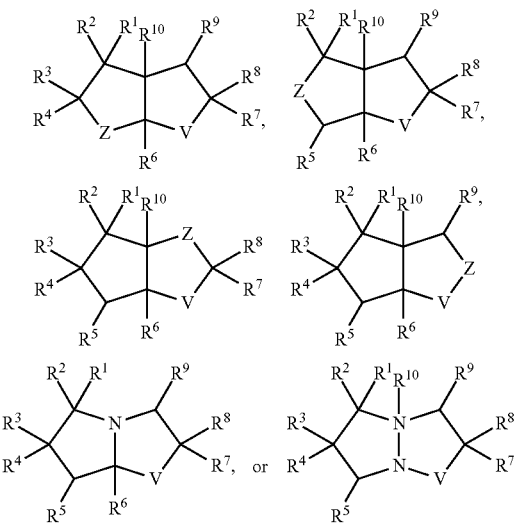

where Z is O, S, Se, or $NR^{11}$.

In one embodiment, the compound has a formula

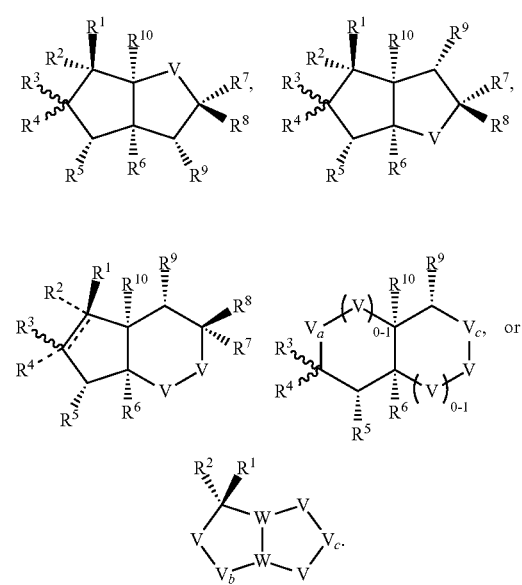

In one embodiment, the compound is

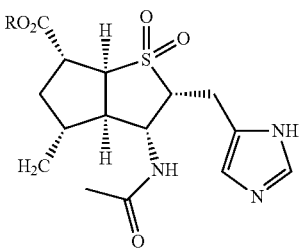

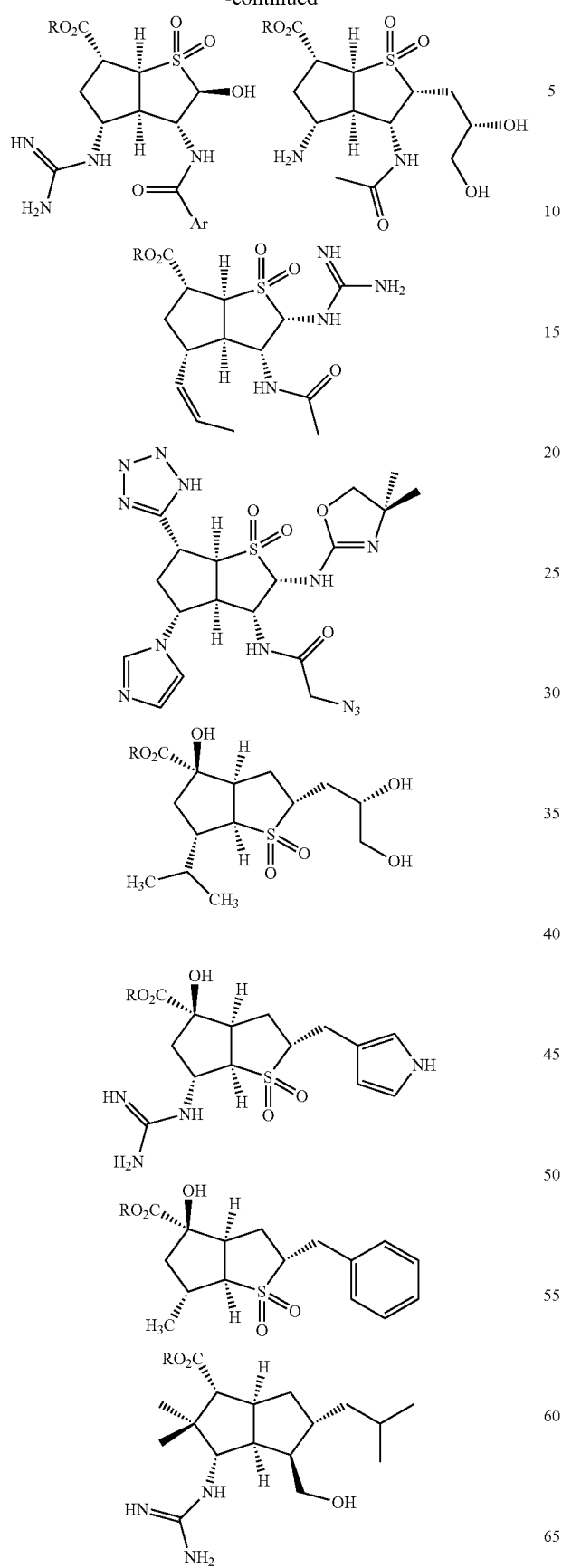
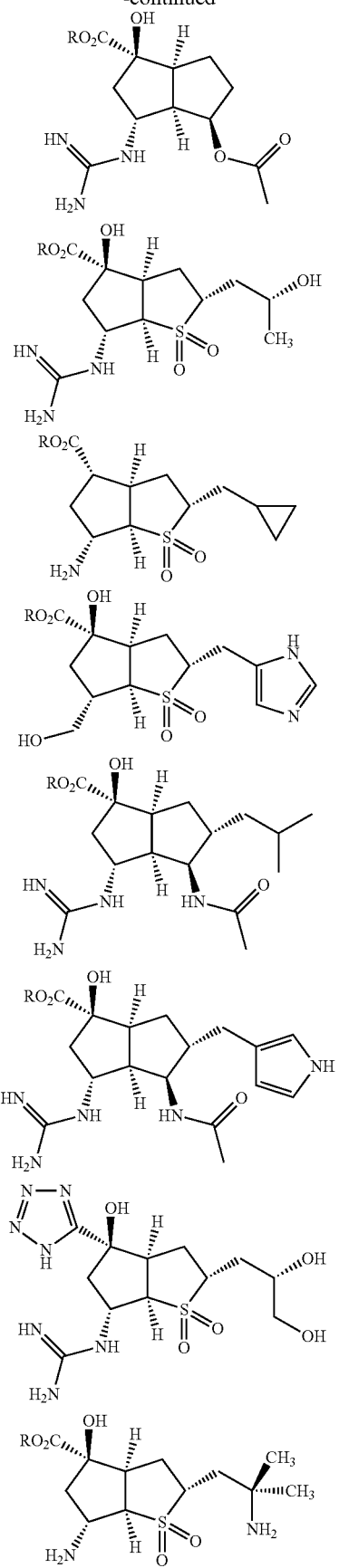

-continued
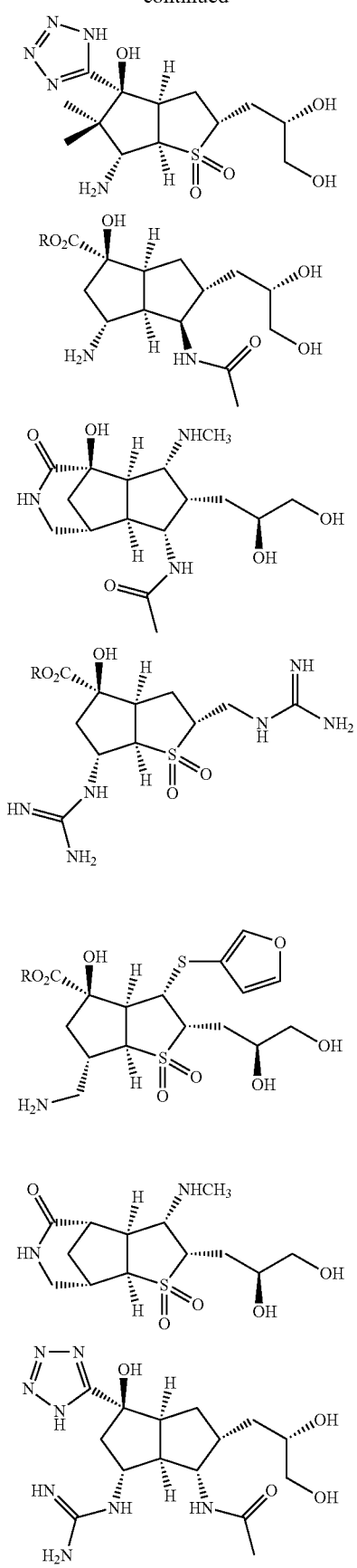
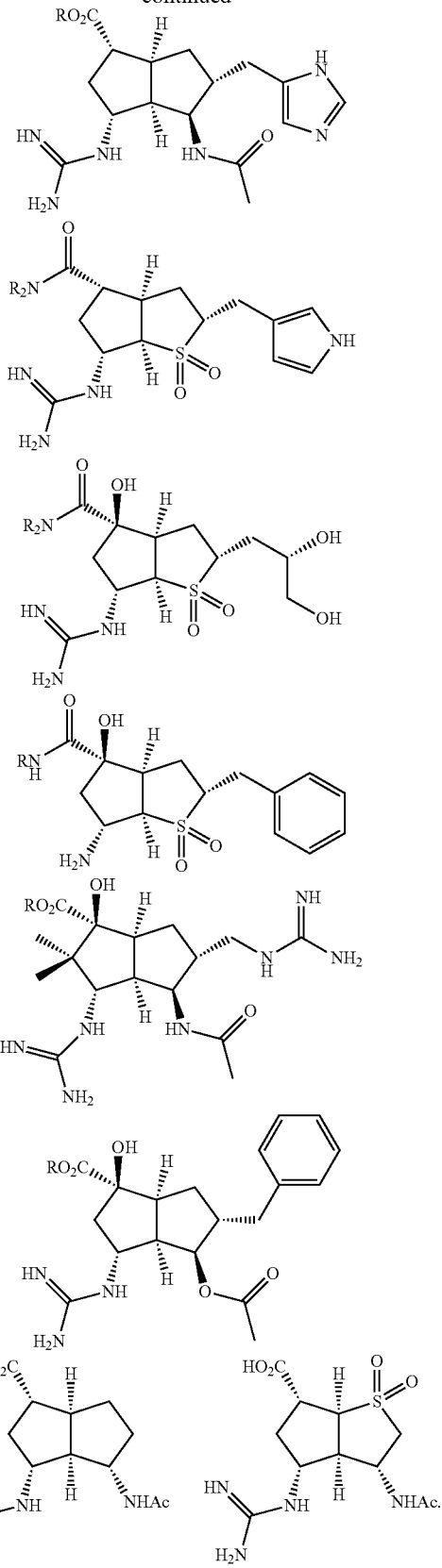
where R is selected from H, alkyl, aryl, heteroaryl, or acyl; and Ar is aryl or heteroaryl.

In one embodiment, the specific binding moiety is selected from an antibody, protein, or nucleic acid.

In one embodiment, the signal generating moiety is selected from an enzyme, a chromogenic compound, a fluorogenic compound, or lumogenic compound.

In one embodiment, the signal generating moiety is a nanoparticle

In one embodiment, the compound and the specific binding moiety are coupled to each other directly.

In one embodiment, the compound and the specific binding moiety are coupled covalently or non-covalently.

In one embodiment, the compound and the specific binding moiety are coupled to each other through a linker.

In one embodiment, the linker is aliphatic or heteroaliphatic.

In one embodiment, the linker is homobifunctional or heterobifunctional.

Other embodiments concern a method of making a bicyclic compound, comprising converting a starting material to a product having a formula

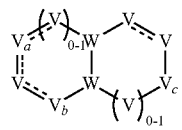

where V, $V_a$, $V_b$, and $V_c$ are $CR^{11}R^{12}$, $C(R^{11})_2$, $CR^{12}R^{13}$, $C(R^{13})_2$, $SO_2$, SO, S, O, $NR^{11}$, CO, and Se;

W is nitrogen, $CR^{10}$, or $CR^{11}$;

$R^{10}$ is H, alkyl or $(CH_2)_nOH$;

$R^{11}$ is H, alkyl, branched alkyl, cyclic alkyl, aryl, a heteroatom-containing moiety, and any combination thereof;

$R^{12}$ is H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z=O, S, Se, or $NR^{11}$;

$R^{13}$ is H, alkyl, branched alkyl, cyclic alkyl, alkenyl, alkynyl, aryl, a heteroatom-containing moiety, and any combination thereof;

if $V_a$ comprises $CR^{11}R^{12}$, $C(R^{11})_2$, $C^{12}R^{13}$, or $C(R^{13})_2$, then $V_a$ and $V_b$ together can comprise a lactone or a lactam;

if $V_c$ comprises $CR^{11}R^{12}$, $C(R^{11})^2$, $CR^{12}R^{13}$, or $C(R^{13})_2$ and has at least two substituents selected from $R^{11}$, $R^{12}$, or $R^{13}$, or any combination thereof, then the two substituents together can form a cyclic alkyl group;

n=0, 1 or 2; and m=0, 1 or 2.

In one embodiment, converting comprises oxidizing a cyclic diene with a first oxidant to produce a first intermediate; exposing the first intermediate to a base to make the bicyclic intermediate having a formula

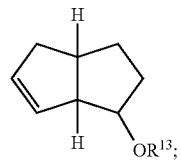

and oxidizing the bicyclic intermediate with a second oxidant.

In one embodiment, converting comprises exposing an acidic cyclic compound comprising an olefin and a sulfone, and a cyclic or acyclic, dialkylidene ketone or a dialkylidene sulfoxide to a base to make the bicyclic intermediate.

In one embodiment, the acidic cyclic compound is a sulfone, and further comprising alkylating the bicyclic intermediate at a position alpha to a sulfone moiety; performing an ozonolysis reaction; and oxidizing the aldehyde to the carboxylic acid.

In one embodiment, the acidic cyclic compound is a sulfone, and further comprising oxidatively cleaving an exocyclic olefin to form an aldehyde; and oxidizing the aldehyde to a carboxylic acid.

In one embodiment, the bicyclic compound is

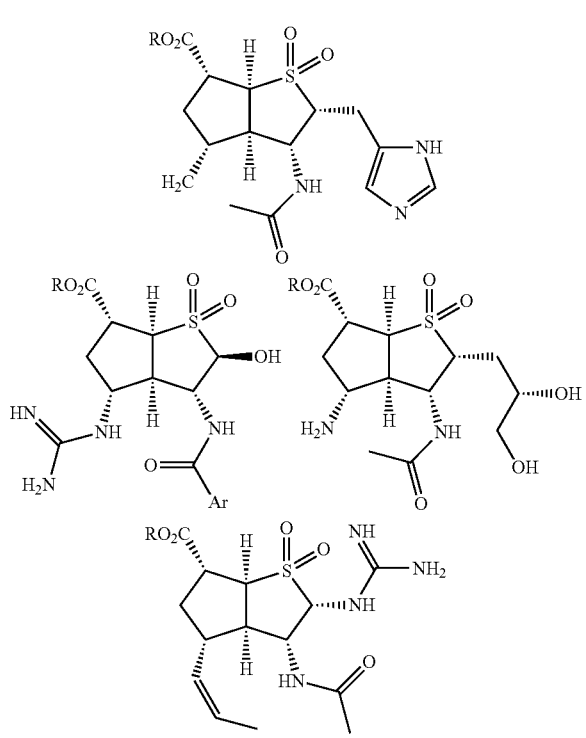

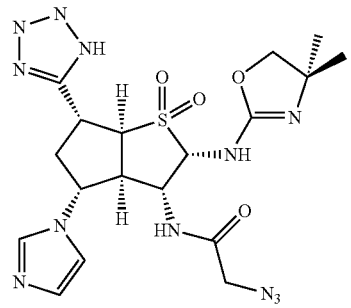

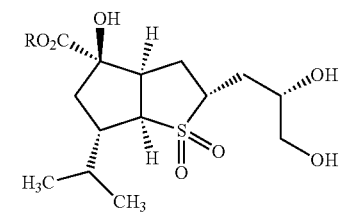

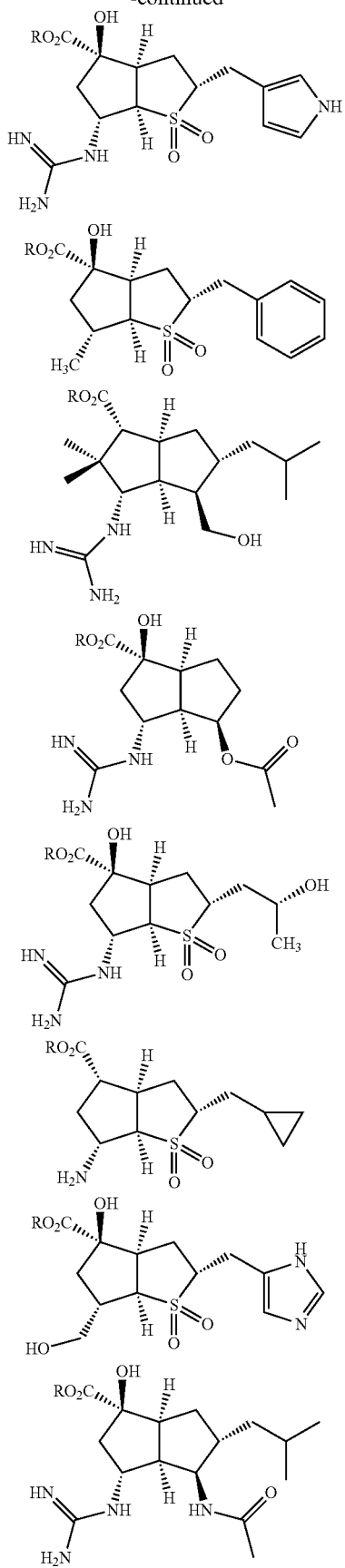
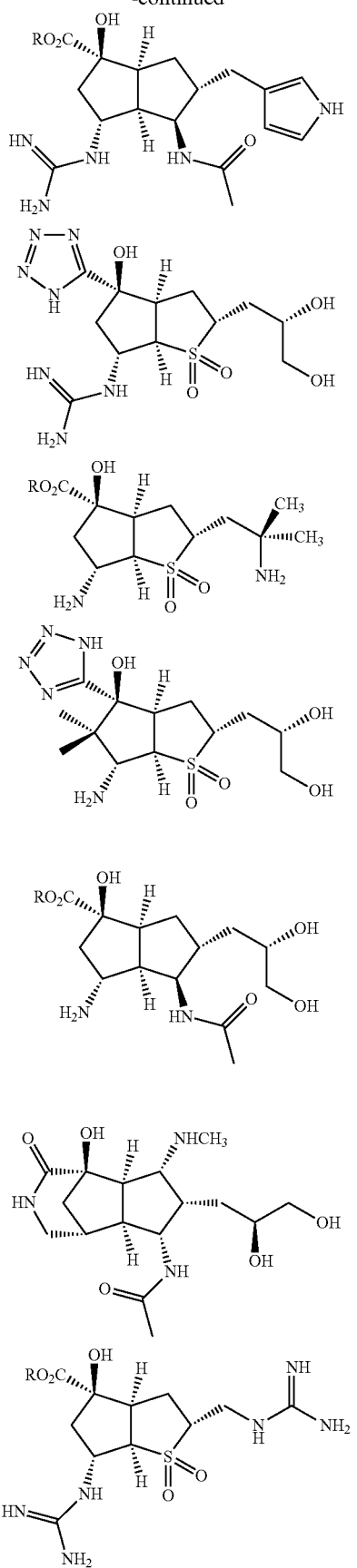

where R is selected from H, alkyl, aryl, heteroaryl, or acyl; and Ar is aryl or heteroaryl.

Another embodiment concerns a method for making a bicyclic compound, comprising oxidizing cyclooctadiene with peracetic acid to make an oxidized cyclooctadiene; treating the oxidized cyclooctadiene with a base to form a bicyclic intermediate having a structure and oxidizing the bicyclic intermediate with selenium dioxide or CO$_3$-pyridine.

Yet another embodiment concerns a method for making a bicyclic compound, comprising exposing butadiene sulfone and a dialkylidene ketone to a base to form a bicyclic intermediate having a structure In another embodiments, a method for inhibiting H1N1 neuraminidase is described wherein the method comprises administering an effective amount of the one or more compounds disclosed herein to a subject expressing the H1N1 neuraminidase.

The invention has been described in detail sufficient to allow a person of ordinary skill in the art to make and use claimed invention. A person of ordinary skill in the art also will appreciate that certain modifications of the methods and compositions of the claims can be made and still be within the scope of the claimed invention.

We claim:

1. A compound, having a formula

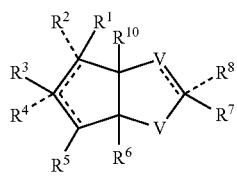

where each V independently is selected from $CR^{11}R^{12}$, $C(R^{11})CR^{12}R^{13}$, $C(R^{13})_2$, $SO_2$, $SO$, $S$, $O$, $NR^{11}$, $CO$, or $Se$;

$R^1$ is selected from $CO_2H$, $SO_2H$, $SO_3H$, $PO_3H_2$, aliphatic esters, or aliphatic amides;

$R^2$ is selected from H, OH, SH or aliphatic amine;

$R^3$ and $R^4$ independently are selected from hydrogen, or alkyl;

$R^5$ is selected from $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is selected from O, S, Se, or $NR^{11}$, guanidino, substituted guanidino, alkyl, cyclic alkyl, alkenyl, alkynyl, aryl, or heteroaryl;

$R^6$ is selected from H, alkyl or $(CH_2)_nOH$;

$R^7$ and $R^8$ independently are selected from H, alkyl, cyclic alkyl, aryl, heteroaryl, $(CH_2)_nY$, $(CH_2)_nZY$, $(CH_2)_nCR^{11}Z$, $(CH_2)_2ZH$, $[CH_2]_n[CH(ZH)]_mCH_2ZH$, $[CH_2]_n[CH(ZH)]_mCH_2Y$, where Y is selected from aryl, heteroaryl, alkyl, cyclic alkyl, heterocyclic, amino or guanidino, and Z is selected from O, S, Se, or $NR^{11}$, or $R^7$ and $R^8$ together represent a cyclic alkyl group;

$R^{10}$ is selected from H, alkyl or $(CH_2)_nOH$;

$R^{11}$ is selected from H, alkyl, cyclic alkyl, or aryl;

$R^{12}$ is selected from H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_n Z(CO)OR^{11}$, or $(CH_2)_nZ(CNH)NH_2$, where Z [H] is selected from O, S, Se, or $NR^{11}$;

$R^{13}$ is selected from H, alkyl, cyclic alkyl, alkenyl, alkynyl, aryl, or any combination thereof;

n=0, 1 or 2; and m=0, 1 or 2.

2. The compound of claim 1 where the compound is selected from

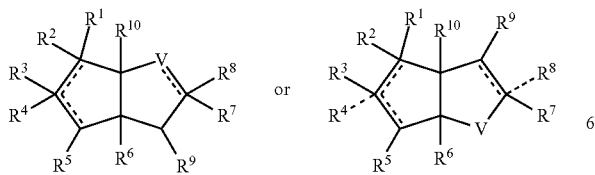

where V independently is selected from $CR^{11}R^{12}$, $C(R^{11})^2$, $C(R^{13})_2$, $SO_2$, $SO$, $S$, $O$, $NR^{11}$, $CO$, or $Se$;

$R^1$ is selected from $CO_2H$, $SO_2H$, $SO_3H$, $PO_3H_2$, aliphatic esters, or aliphatic amides;

$R^2$ is selected from H, OH, SH or aliphatic amine;

$R^3$ and $R^4$ independently are selected from hydrogen or alkyl;

$R^5$ is selected from $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is selected from O, S, Se, or $NR^{11}$, guanidino, substituted guanidino, alkyl, cyclic alkyl, alkenyl, alkynyl, aryl, or heteroaryl;

$R^6$ is selected from H, alkyl or $(CH_2)_nOH$;

$R^7$ and $R^8$ independently are selected from H, alkyl, cyclic alkyl, aryl, heteroaryl, $(CH_2)_nY$, $(CH_2)_nZY$, $(CH_2)_nCR^{11}Z$, $(CH_2)_2ZH$, $[CH_2]_n[CH(ZH)]_mCH_2ZH$, $[CH_2]_n[CH(ZH)]_mCH_2Y$, where Y is selected from aryl, heteroaryl, alkyl, cyclic alkyl, heterocyclic, amino or guanidino, and Z is selected from O, S, Se, or $NR^{11}$, or $R^7$ and $R^8$ together represent a cyclic alkyl group; and $R^9$ is selected from H, alkyl, cyclic alkyl, alkenyl, alkynyl, aryl, heteroaryl, $O(R^{11})_m$, $S(R^{11})_m$, $N(R^{11})_m(H)_{(2-m)}$, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, where Z is selected from O, S, Se, or $NR^{11}$.

3. The compound according claim 1 where the compound is a pharmaceutically acceptable salt.

4. The compound according to claim 1 having a formula

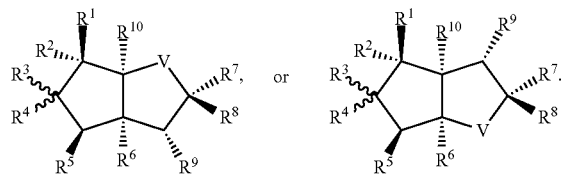

5. A compound selected from

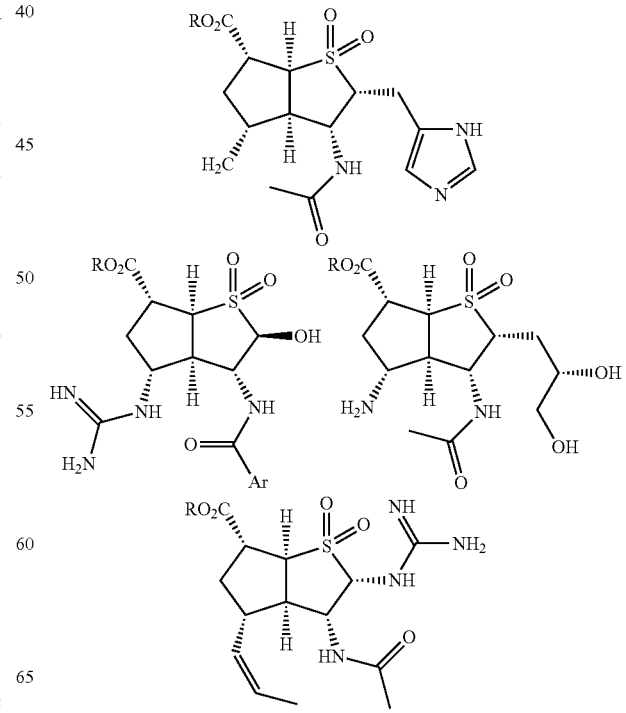

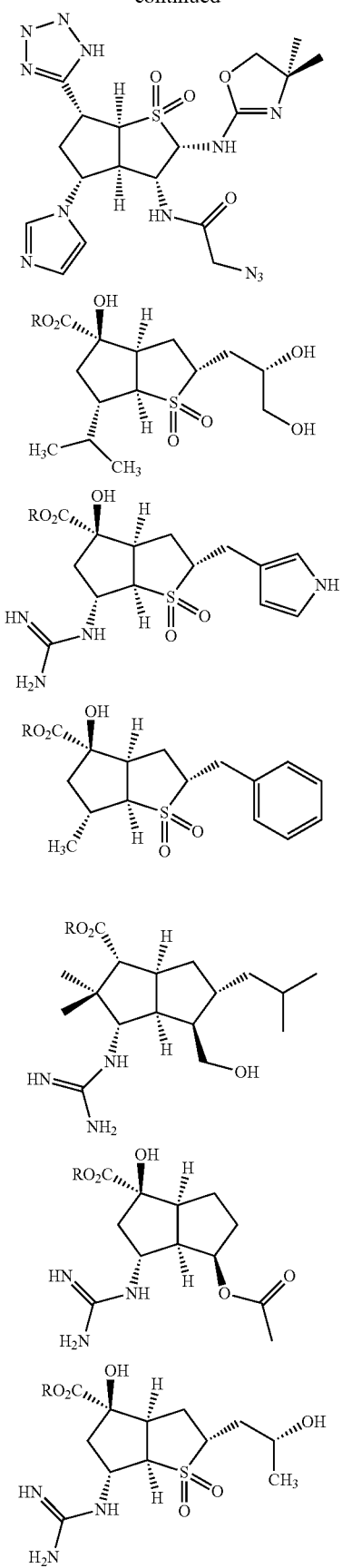
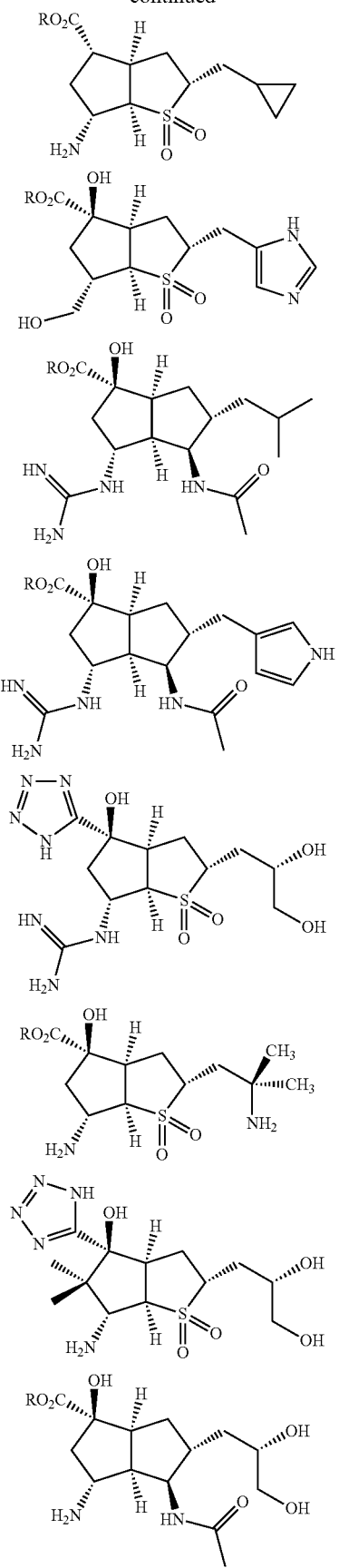

97
-continued
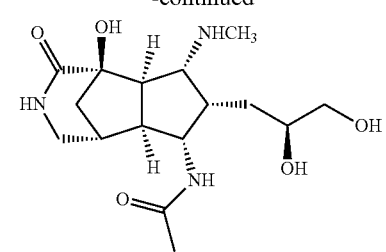
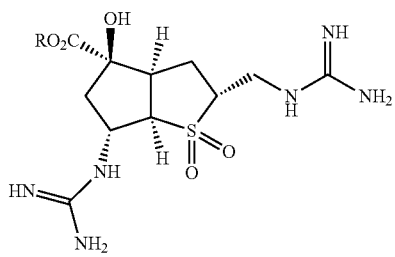
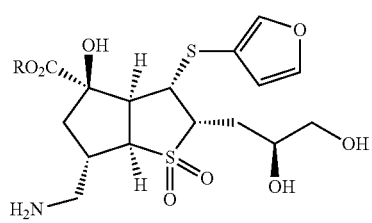
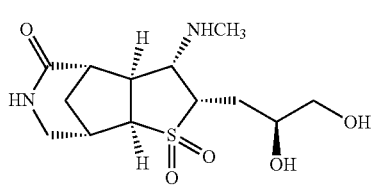
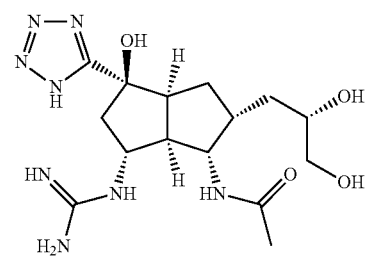
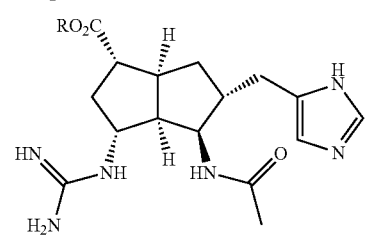
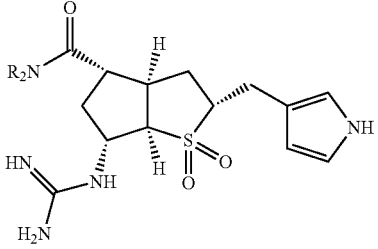
98
-continued
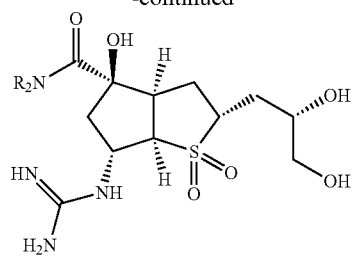
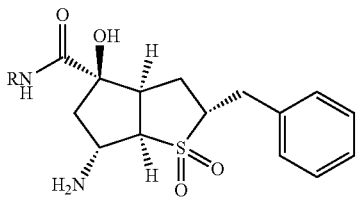
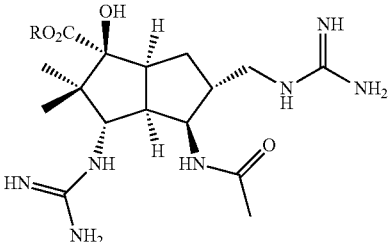
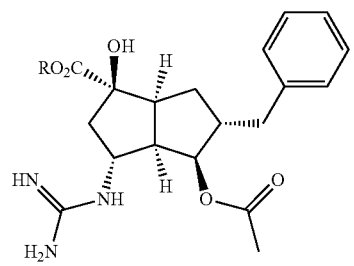
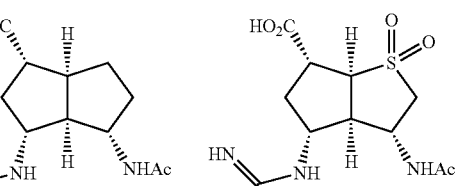
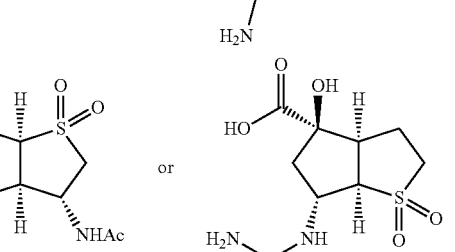
or
where R is selected from H aliphatic.

6. A composition, comprising:
at least one compound having a formula where V, independently is selected from $CR^{11}R^{12}$, $C(R^{11})_2$, $CR^{12}R^{13}$, $C(R^{13})_2$, $SO_2$, $SO$, $S$, $O$, $NR^{11}$, $CO$, or $Se$;

$R^1$ is selected from $CO_2H$, $SO_2H$, $SO_3H$, $PO_3H_2$, aliphatic esters, or aliphatic amides;

$R^2$ is selected from H, OH, SH or aliphatic amine;

$R^3$ and $R^4$ independently are selected from hydrogen or alkyl;

$R^5$ is selected from $NH_2$, $(CH_2)_nN(R^{11})_m(H)_{(2-m)}$, $(CH_2)_nNHC(O)(R^{11})$, $(CH_2)_nNC(=NR^{11})N(R^{11})_m(H)_{(2-m)}$, $(CH_2)_nNHC(O)Z(R^{11})$, $(CH_2)_nZH$, where Z is selected from O, S, Se, or $NR^{11}$, guanidino, substituted guanidino, alkyl, alkyl, alkenyl, alkynyl, aryl, or heteroaryl;

$R^6$ is selected from H, alkyl or $(CH_2)_nOH$;

$R^7$ and $R^8$ independently are selected from H, alkyl, cyclic alkyl, aryl, heteroaryl, $(CH_2)_nY$, $(CH_2)_nZY$, $(CH_2)_nCR^{11}Z$, $(CH)_2ZH$, $[CH_2]_n[CH(ZH)]_mCH_2ZH$, $[CH_2]_n[CH(ZH)]_mCH_2Y$, where Y is selected from aryl, heteroaryl, alkyl, cyclic alkyl, heterocyclic, amino or guanidino, and Z is selected from O, S, Se, or $NR^{11}$, or $R^7$ and $R^8$ together represent a cyclic alkyl group;

$R^{10}$ is selected from H, alkyl or $(CH_2)_nOH$;

$R^{11}$ is selected from H, alkyl, cyclic alkyl, or aryl;

$R^{12}$ is selected from H, $(CH_2)_nZH$, $(CH_2)_nZR^{11}$, $(CH_2)_nZ(CO)R^{11}$, $(CH_2)_nZ(SO_2)R^{11}$, $(CH_2)_nZ(CO)NH_2$, $(CH_2)_nZ(CO)OR^{11}$, or $(CH_2)_nZ(CNH)NH_2$, and Z is selected from O, S, Se, or $NR^{11}$;

$R^{13}$ is selected from H, alkyl, cyclic alkyl, alkenyl, alkynyl, aryl, or any combination thereof;

n=0, 1 or 2;

m=0, 1 or 2; and at least one biologically acceptable material selected from a carrier, diluent, adjuvant, excipient, binder, filler, lubricant, osmotic agent, flavoring agent, solvent, fat emulsion, lipid, PEGylated phopholids polymer matrix, biocompatible polymer, liposphere, vesicle, particle, liposome, stabilizing agent, solubilizing agent, surfactant, buffer, antioxidant, preservative, tonicity agent, bulking agent, emulsifier, suspending agent, viscosity agent, disintegrating agent, binding agent, wetting agent, lubricating agent, antibacterial agent, chelating agent, sweetening went, perfuming agent, flavoring agent, coloring agent, administration aid, metallic stearate, wax, oil, other active ingredient, or combinations thereof.

7. The composition according to claim 6 where the compound is a pharmaceutically acceptable salt.

8. The composition according to claim 6 where the at least one biologically acceptable material is selected from saline; buffered saline; dextrose; water; glycerol; ethanol; propylene glycol; polysorbate 80 (Tween-80TH); poly(ethylene)glycol 300 and 400 (PEG 300 and 400); PEGylated castor oil (e.g. Cremophor EL); poloxamer 407 and 188; sodium carbonate; calcium carbonate; sodium phosphate; calcium phosphate; lactose; sodium chloride; glycerol; sorbitol; xylitol; glucose; *acacia* gum; starch; gelatin; sucrose; polyvinylpyrrolidone (Providone); sorbitol; tragacanth methylcellulose; sodium carboxymethylcellulose; hydroxypropyl methylcellulose; ethylcellulose; calcium phosphate; glycine; lactose; maizestarch; sorbitol; sucrose; magnesium stearate; stearic acid; polyethylene glycol; silica; colloidal silica; silicon fluid; talc; peppermint; oil of wintergreen; or combinations thereof.

9. A method for treating influenza infection in a subject, comprising administering to a subject an effective amount of at least one compound according to claim 1.

10. The method according to claim 9 where the compound is a pharmaceutically acceptable salt.

11. The method according to claim 9 where the subject is a human.

12. The method according to claim 9 where the compound is administered prophylactically.

13. The method according to claim 9 where the effective amount is from greater than 0 to about 1000 mg/kg body weight per day.

14. The method according to claim 9 where the effective amount is from greater than 0 to about 0.5 mg/kg body weight per day.

15. The method according to claim 9 where the compound is administered in single or multiple doses.

16. The method according to claim 9 where administering comprises oral, rectal, nasal, topical, (buccal, sublingual, vaginal, parenteral, (subcutaneous, intramuscular, intravenous, intradermal, intrathecal, or epidural administering, or combinations thereof.

17. A method for making a bicyclic compound, comprising:
oxidizing cyclooctadiene with peracetic acid to make an oxidized cyclooctadiene;
treating the oxidized cyclooctadiene with a base to form a bicyclic intermediate having a structure and
oxidizing the bicyclic intermediate with selenium dioxide or $CO_3$-pyridine.

18. A method for inhibiting H1N1 neuraminidase in vitro, comprising contacting a neuraminidase with an effective amount of the compound of claim 1.

* * * * *